United States Patent
Bai et al.

(10) Patent No.: US 12,180,307 B2
(45) Date of Patent: Dec. 31, 2024

(54) INTERLEUKIN-13 BINDING CYCLIC OLIGOPEPTIDES AND METHODS OF USE THEREOF

(71) Applicant: B.A.I. LABORATORIES, LLC, Cambridge, MA (US)

(72) Inventors: Xuefei Bai, Cambridge, MA (US); Sheng Lin, Beijing (CN); Le Li, Beijing (CN)

(73) Assignee: B.A.I. Laboratories, LLC, Cambridge, MA (US)

( * ) Notice: Subject to any disclaimer, the term of this patent is extended or adjusted under 35 U.S.C. 154(b) by 0 days.

(21) Appl. No.: 18/334,309

(22) Filed: Jun. 13, 2023

(65) Prior Publication Data

US 2023/0399362 A1   Dec. 14, 2023

Related U.S. Application Data

(60) Provisional application No. 63/418,715, filed on Oct. 24, 2022, provisional application No. 63/351,712, filed on Jun. 13, 2022.

(51) Int. Cl.
| | | |
|---|---|---|
| *C07K 7/64* | (2006.01) | |
| *A61K 38/00* | (2006.01) | |
| *A61P 17/00* | (2006.01) | |

(52) U.S. Cl.
CPC ............... *C07K 7/64* (2013.01); *A61P 17/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 5,874,105 A | 2/1999 | Watkins et al. | |
| 6,071,535 A | 6/2000 | Watkins et al. | |
| 6,551,576 B1 | 4/2003 | Unger et al. | |
| 6,808,720 B2 | 10/2004 | Unger | |
| 7,083,572 B2 | 8/2006 | Unger et al. | |
| 7,090,868 B2 | 8/2006 | Gower et al. | |
| 7,195,780 B2 | 3/2007 | Dennis et al. | |
| 7,316,818 B2 | 1/2008 | Yatvin | |
| 8,377,863 B2 | 2/2013 | Stern et al. | |
| 8,936,786 B2 | 1/2015 | Vol et al. | |
| 2004/0146549 A1 | 7/2004 | Ben-Sasson et al. | |
| 2007/0184076 A1 | 8/2007 | Unger et al. | |
| 2021/0301010 A1 | 9/2021 | Colice et al. | |

FOREIGN PATENT DOCUMENTS

| | | |
|---|---|---|
| JP | 2018-172296 A | 11/2018 |
| WO | 2005/014646 A1 | 2/2005 |
| WO | 2005/094785 A2 | 10/2005 |
| WO | 2006/062544 A1 | 6/2006 |
| WO | 2006/097793 A2 | 9/2006 |
| WO | 2010/057275 A1 | 5/2010 |
| WO | 2014/138241 A1 | 9/2014 |
| WO | 2016/115082 A1 | 7/2016 |

OTHER PUBLICATIONS

American Cancer Society (Can melanoma skin cancer be prevented?, downloaded from URL:<https://www.cancer.org/cancer/types/melanoma-skin-cancer/causes-risks-prevention/prevention.html#:~: text=There%20is%20no%20sure%20way,melanoma%20and%20other%20skin%20cancers>, 2023) (Year: 2023).*

Dong, Na., et al., "Simplified Head-to-Tail Cyclic Polypeptides as Biomaterial-Associated Antimicrobials with Endotoxin Neutralizing and Anti-Inflammatory Capabilities", Int. J. Mol. Sci., 20(23):5904 (2019).

* cited by examiner

*Primary Examiner* — Sergio Coffa
(74) *Attorney, Agent, or Firm* — Haley Guiliano LLP

(57) ABSTRACT

The present disclosure relates to cyclic oligopeptides that bind to interleukin-13 (IL-13) which are useful therapeutically in methods of treating or preventing IL-13-associated skin disorders or conditions. The present disclosure also provides methods to treat or prevent IL-13-associated skin disorders or conditions with the IL-13-binding cyclic oligopeptides. The present disclosure further provides methods to produce the IL-13-binding cyclic oligopeptides.

10 Claims, 66 Drawing Sheets

Specification includes a Sequence Listing.

| Time (h) | Permeation 1 (%) | Permeation 2 (%) | Permeation 3 (%) | Permeation Avg. (%) | Range of Permeation (%) |
|---|---|---|---|---|---|
| 1 | 18.70 | 17.35 | 19.57 | 18.54 | 2.23 |
| 2 | 25.26 | 23.51 | 22.64 | 23.80 | 2.62 |
| 4 | 29.45 | 30.77 | 30.93 | 30.38 | 1.48 |
| 8 | 34.99 | 34.38 | 34.23 | 34.53 | 0.75 |
| 12 | 39.05 | 39.23 | 39.55 | 39.28 | 0.49 |
| 24 | 42.13 | 42.07 | 41.98 | 42.06 | 0.14 |

| Time (h) | Permeation 1 (%) | Permeation 2 (%) | Permeation 3 (%) | Permeation Avg. (%) | Range of Permeation (%) |
|---|---|---|---|---|---|
| 1 | 14.08 | 14.93 | 14.86 | 14.62 | 0.85 |
| 2 | 19.52 | 18.57 | 17.63 | 18.57 | 1.89 |
| 4 | 22.88 | 23.20 | 23.55 | 23.21 | 0.67 |
| 8 | 25.40 | 25.37 | 25.33 | 25.36 | 0.07 |
| 12 | 28.27 | 28.55 | 28.67 | 28.50 | 0.40 |
| 24 | 30.30 | 30.71 | 30.51 | 30.51 | 0.41 |

| Time/hr | 1 | 2 | 4 | 8 | 12 | 24 |
|---|---|---|---|---|---|---|
| Kp value | 3.13E-02 | 6.45E-03 | 3.76E-03 | 4.27E-04 | 9.26E-04 | 8.74E-05 |

| Time (h) | Permeation 1 (%) | Permeation 2 (%) | Permeation 3 (%) | Permeation Avg. (%) | Range of Permeation (%) |
|---|---|---|---|---|---|
| 1 | 18.81 | 19.47 | 20.56 | 19.61 | 1.75 |
| 2 | 24.73 | 24.00 | 23.74 | 24.16 | 0.99 |
| 4 | 28.37 | 28.64 | 28.95 | 28.65 | 0.58 |
| 8 | 31.48 | 31.21 | 31.23 | 31.31 | 0.27 |
| 12 | 34.64 | 34.70 | 34.50 | 34.61 | 0.20 |
| 24 | 36.61 | 36.64 | 36.52 | 36.59 | 0.12 |

Compound 3

| Time (h) | Permeation 1 (%) | Permeation 2 (%) | Permeation 3 (%) | Permeation Avg. (%) | Range of Permeation (%) |
|---|---|---|---|---|---|
| 1 | 16.79 | 17.16 | 17.89 | 17.28 | 1.11 |
| 2 | 22.53 | 21.78 | 21.11 | 21.81 | 1.42 |
| 4 | 25.95 | 27.39 | 27.95 | 27.10 | 1.99 |
| 8 | 30.44 | 30.17 | 29.80 | 30.14 | 0.64 |
| 12 | 33.02 | 33.19 | 33.46 | 33.22 | 0.44 |
| 24 | 35.65 | 35.50 | 35.63 | 35.59 | 0.14 |

| Time (h) | Permeation 1 (%) | Permeation 2 (%) | Permeation 3 (%) | Permeation Avg. (%) | Range of Permeation (%) |
|---|---|---|---|---|---|
| 1 | 20.42 | 22.09 | 24.88 | 22.46 | 4.46 |
| 2 | 31.21 | 29.91 | 27.51 | 29.54 | 3.70 |
| 4 | 37.40 | 36.26 | 38.00 | 37.22 | 1.74 |
| 8 | 41.04 | 40.59 | 41.18 | 40.94 | 0.59 |
| 12 | 45.84 | 46.03 | 45.84 | 45.90 | 0.19 |
| 24 | 48.57 | 48.57 | 49.05 | 48.73 | 0.47 |

| Time (h) | Permeation 1 (%) | Permeation 2 (%) | Permeation 3 (%) | Permeation Avg. (%) | Range of Permeation (%) |
|---|---|---|---|---|---|
| 1 | 14.65 | 15.34 | 16.02 | 15.34 | 1.38 |
| 2 | 22.71 | 20.32 | 23.01 | 22.01 | 2.69 |
| 4 | 26.34 | 26.04 | 26.12 | 26.17 | 0.31 |
| 8 | 29.80 | 29.20 | 28.73 | 29.25 | 1.07 |
| 12 | 32.22 | 31.49 | 31.60 | 31.77 | 0.73 |
| 24 | 34.44 | 33.52 | 33.62 | 33.86 | 0.92 |

| Time (h) | Permeation 1 (%) | Permeation 2 (%) | Permeation 3 (%) | Permeation Avg. (%) | Range of Permeation (%) |
|---|---|---|---|---|---|
| 1 | 25.38 | 25.40 | 25.48 | 25.42 | 0.11 |
| 2 | 28.84 | 28.63 | 27.47 | 28.31 | 1.37 |
| 4 | 31.51 | 31.52 | 31.07 | 31.36 | 0.44 |
| 8 | 34.19 | 33.61 | 33.17 | 33.66 | 1.02 |
| 12 | 37.27 | 36.59 | 36.35 | 36.74 | 0.93 |
| 24 | 39.01 | 38.71 | 38.80 | 38.84 | 0.21 |

| Time (h) | Permeation 1 (%) | Permeation 2 (%) | Permeation 3 (%) | Permeation Avg. (%) | Range of Permeation (%) |
|---|---|---|---|---|---|
| 1 | 11.61 | 12.21 | 13.50 | 12.44 | 1.89 |
| 2 | 19.16 | 17.24 | 16.32 | 17.57 | 2.85 |
| 4 | 22.25 | 23.08 | 24.40 | 23.24 | 2.16 |
| 8 | 28.66 | 27.50 | 27.13 | 27.76 | 1.53 |
| 12 | 32.37 | 32.19 | 32.43 | 32.33 | 0.25 |
| 24 | 35.19 | 35.34 | 35.08 | 35.20 | 0.26 |

| Time (h) | Permeation 1 (%) | Permeation 2 (%) | Permeation 3 (%) | Permeation Avg. (%) | Range of Permeation (%) |
|---|---|---|---|---|---|
| 1 | 19.48 | 23.56 | 27.15 | 23.40 | 7.67 |
| 2 | 32.36 | 30.41 | 30.64 | 31.10 | 1.85 |
| 4 | 40.08 | 42.19 | 43.51 | 41.93 | 3.42 |
| 8 | 48.30 | 48.33 | 48.07 | 48.23 | 0.27 |
| 12 | 54.61 | 54.74 | 55.93 | 55.09 | 1.32 |
| 24 | 60.26 | 59.33 | 62.31 | 60.63 | 2.98 |

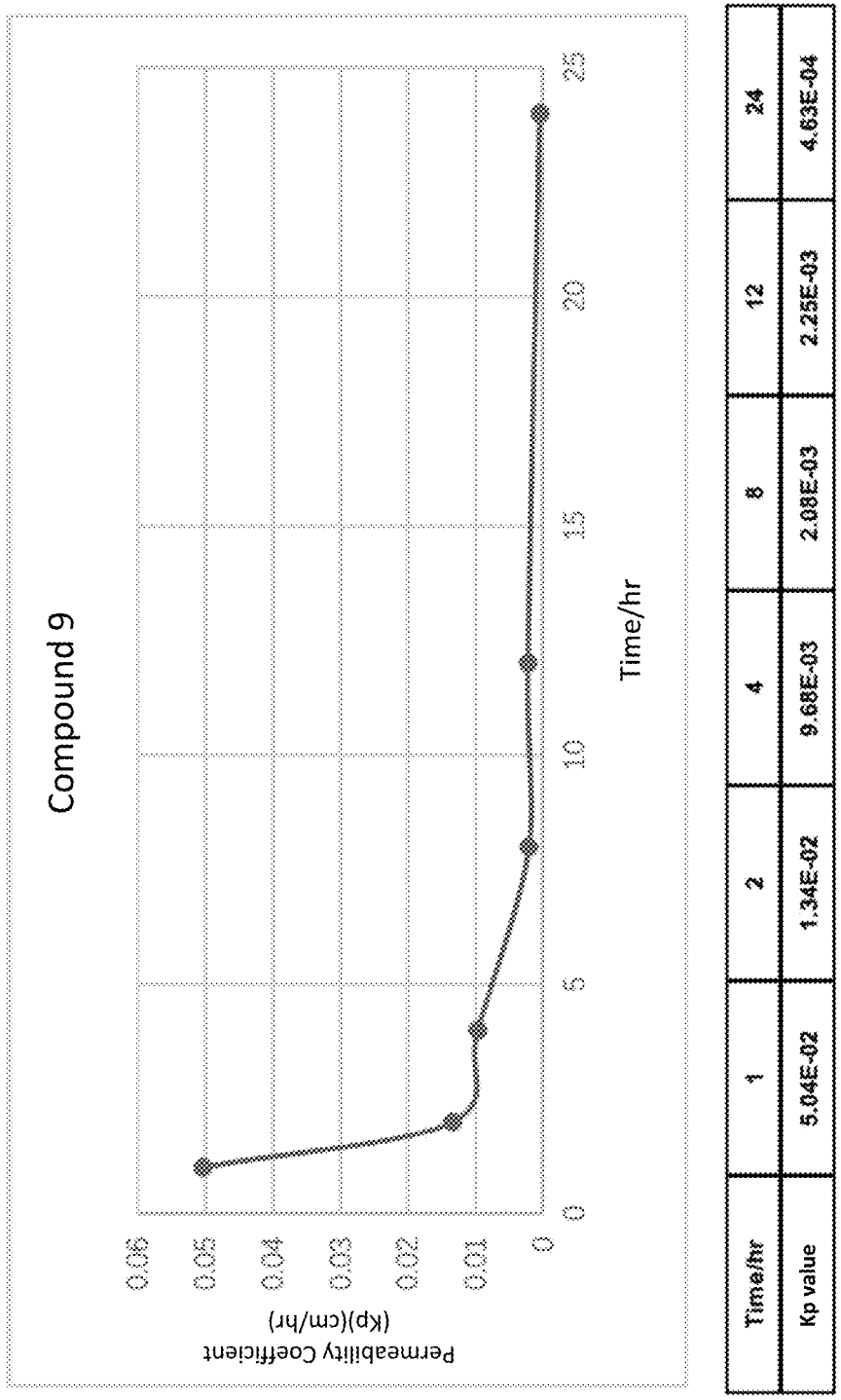

| Time (h) | Permeation 1 (%) | Permeation 2 (%) | Permeation 3 (%) | Permeation Avg. (%) | Range of Permeation (%) |
|---|---|---|---|---|---|
| 1 | 16.20 | 18.27 | 22.40 | 18.96 | 6.20 |
| 2 | 31.75 | 27.75 | 28.03 | 29.18 | 4.00 |
| 4 | 37.93 | 39.85 | 42.20 | 39.99 | 4.27 |
| 8 | 48.51 | 48.51 | 46.86 | 47.96 | 1.65 |
| 12 | 58.01 | 55.52 | 55.79 | 56.44 | 2.49 |
| 24 | 61.94 | 59.95 | 60.74 | 60.88 | 1.99 |

| Time (h) | Permeation 1 (%) | Permeation 2 (%) | Permeation 3 (%) | Permeation Avg. (%) | Range of Permeation (%) |
|---|---|---|---|---|---|
| 1 | 10.25 | 11.80 | 13.25 | 11.77 | 3.00 |
| 2 | 15.94 | 15.40 | 15.49 | 15.61 | 0.54 |
| 4 | 18.75 | 18.81 | 19.99 | 19.18 | 1.24 |
| 8 | 20.97 | 21.03 | 23.23 | 21.74 | 2.27 |
| 12 | 23.44 | 23.64 | 24.64 | 23.90 | 1.20 |
| 24 | 25.20 | 25.63 | 26.43 | 25.75 | 1.23 |

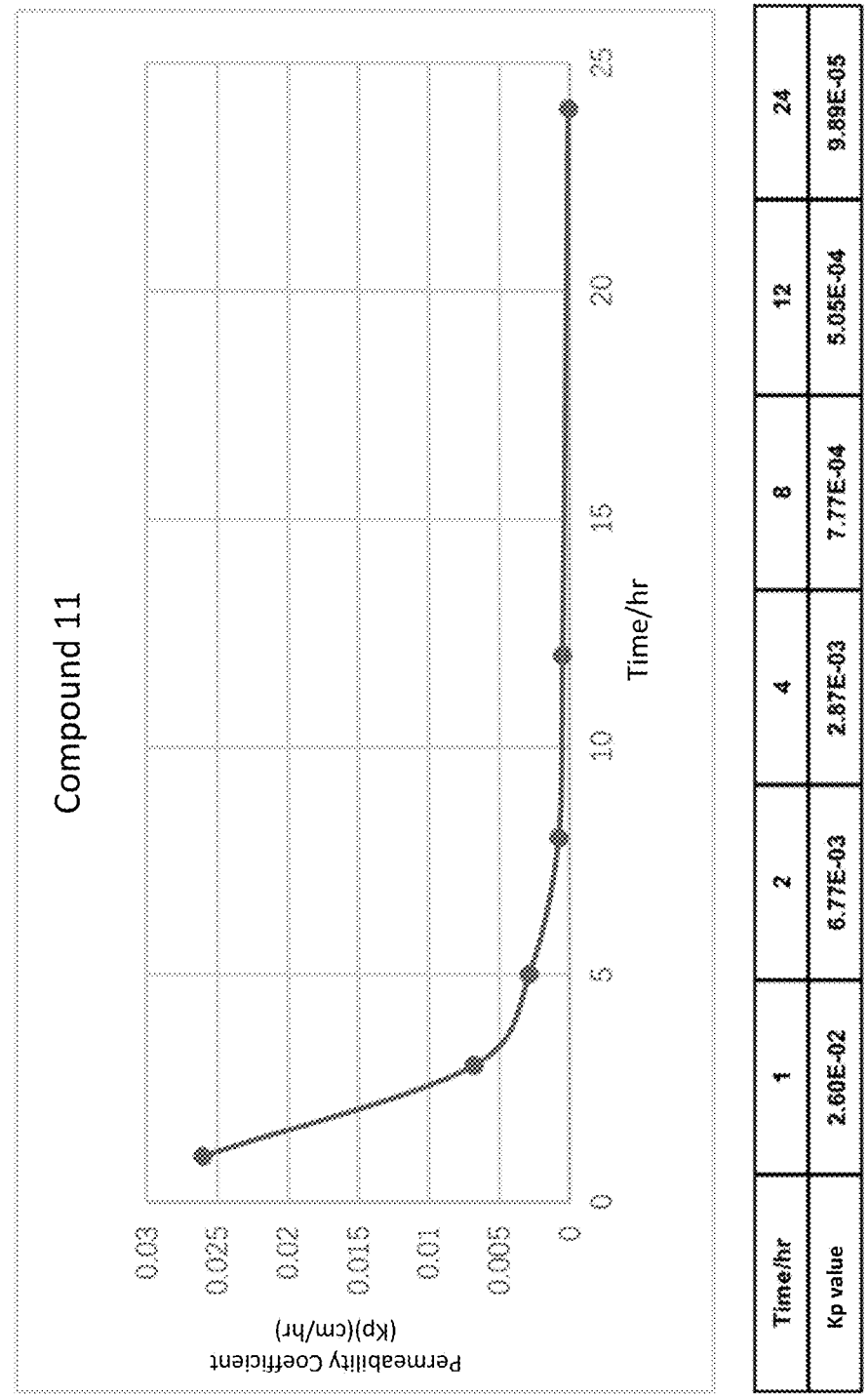

INTERLEUKIN-13 BINDING CYCLIC OLIGOPEPTIDES AND METHODS OF USE THEREOF

CROSS-REFERENCE TO RELATED APPLICATIONS

This application is a United States Nonprovisional Application claiming the benefit of priority from U.S. Provisional Application No. 63/351,712, filed on Jun. 13, 2022, and U.S. Provisional Application No. 63/418,715, filed on Oct. 24, 2022. The contents and disclosure of each of the foregoing applications are incorporated by reference herein in their entireties.

SEQUENCE LISTING

The instant disclosure contains a Sequence Listing, which has been submitted electronically in XML format and is hereby incorporated by references in its entirety. Said XML copy, created Jun. 13, 2023, is named "000388-0004-101.xml" and is 25,927 bytes in size.

BACKGROUND OF THE DISCLOSURE

Interleukin-13 (IL-13) is one of the key cytokines involved in the type 2 (T2) immune response. A recent study has shown that it plays an important role driving inflammation in the periphery. IL-13 is secreted by T lymphocytes and mast cells and has been identified as the primary cytokine involved in atopic dermatitis (AD) inflammation, as evidenced by local overexpression of IL-13. IL-13 impacts skin biology through the recruitment of inflammatory cells, the alteration of the skin microbiome and the decrease in the epidermal barrier function. Alopecia Areata (AA) is an autoimmune disorder that shares phenotypic similarities with AD, such as pruritus, elevated IgE levels, and filaggrin mutations. A genomic study in patients with AA identified IL-13 gene susceptibility. In addition, lesional scalps from AA patients demonstrated increased IL-13 mRNA as compared to nonlesional scalps. Moreover, AA patients demonstrated significantly elevated IL-13 levels in serum as compared with healthy control group.

IL-13's significant impact on the skin immune response and barrier function is partially through its ability to activate of STAT6, resulting in decreased expression of key structural proteins, such as filaggrin, filaggrin 2, loricrin, involucrin, keratin 1, keratin 10, hornerin, desmoglein, and desmocollin1, as well as the lipid compositions of skin. These changes contribute to the increased transepidermal water loss (TEWL), which is a hallmark of AD. IL-13 is also reported to decrease the production of AMP by keratinocytes and thereby play a role in the dysbiosis of the skin, characterized by a strong colonization with *Staphylococcus aureus*, which has been shown to precede the appearance of AD lesions.

In view of IL-13's role in the generation and maintenance of the inflammatory reaction and its significant impact on epidermal barrier function, pharmacological approaches targeting IL-13-induced pathways are in development. Such approaches include small molecules interfering with interactions between IL-13 and its receptor; small molecules interfering with intracellular signaling pathways, such as kinase inhibitors; and biologics, such as monoclonal antibodies, blocking the binding of IL-13 to its receptor sites. For example, tralokinumab is a fully human IgG4 antibody that binds to IL-13 at an epitope that overlaps with the binding site of the IL-13Rα receptors, preventing IL-13 from binding to both IL-13Rα1 and IL-13Rα2.

However, each of these approaches has significant limitations in their application to treat skin inflammatory conditions and diseases, such as AD and AA. For example, current treatment of atopic dermatitis with topical corticosteroid may result in undesired side effects such as atrophy or thinning of skin, stria or stretch marks, easy bruising, and telangiectasia. Continuous treatment with topical steroid may also result in withdrawal or rebound effects once the treatment ceases, symptoms include, for example, skin burning, itching, and peeling. In addition, existing antibody treatment for AD, such as tralokinumab, is administered by injection. Accordingly, there remains a need for therapeutics targeting IL-13 for treating skin diseases and conditions, especially those that are suitable for topical application.

SUMMARY OF THE DISCLOSURE

The present disclosure provides cyclic oligopeptides that bind IL-13 and methods of using such cyclic oligopeptides to treat IL-13-associated skin disorders or conditions.

A first aspect of the present disclosure provides a cyclic oligopeptide that binds to IL-13. In some embodiments, the cyclic oligopeptide comprises between two and twenty-two amino acid residues. In some embodiments, the cyclic oligopeptide comprises between six and eight amino acid residues. In some embodiments, the cyclic oligopeptide comprises a L-proline residue or a D-proline residue.

In some embodiments, the cyclic oligopeptide comprises an amino acid sequence selected from the group consisting of SEQ ID NOs:1-11. In some embodiments, the cyclic oligopeptide comprises the amino acid sequence of D-ARG D-PHE D-VAL TYR GLU PRO (SEQ ID NO:1). Optionally, the cyclic oligopeptide comprises the amino acid sequence of ARG THR D-VAL GLU D-PHE D-PRO (SEQ ID NO:2). The cyclic oligopeptide may comprise the amino acid sequence of GLU D-THR D-VAL TRP D-PRO D-PRO (SEQ ID NO:3). In some embodiments, the cyclic oligopeptide comprises the amino acid sequence of ARG GLU D-VAL TRP D-PRO D-PRO (SEQ ID NO:4). Optionally, the cyclic oligopeptide comprises the amino acid sequence of TRP VAL ARG GLU D-PRO D-PRO (SEQ ID NO:5). The cyclic oligopeptide may comprise the amino acid sequence of TYR ARG GLU D-THR D-VAL D-PRO (SEQ ID NO:6). In some embodiments, the cyclic oligopeptide comprises the amino acid sequence of THR ARG D-PHE PRO D-LEU D-PRO (SEQ ID NO:7). Optionally, the cyclic oligopeptide comprises the amino acid sequence of D-LEU ARG GLU PRO TRP MET PRO (SEQ ID NO:8). The cyclic oligopeptide may comprise the amino acid sequence of D-ARG LEU D-TRP TRP D-THR GLU PRO (SEQ ID NO:9). In some embodiments, the cyclic oligopeptide comprises the amino acid sequence of ARG ASP TYR CYS D-PRO D-TRP D-PRO (SEQ ID NO:10). Optionally, the cyclic oligopeptide comprises the amino acid sequence of VAL PRO D-LEU D-TRP D-VAL LEU ARG PRO (SEQ ID NO:11).

In some embodiments, the cyclic oligopeptide has the structure of any one of Compounds 1-11, as defined herein. In some embodiments, the cyclic oligopeptide has the structure of Compound 1, as defined herein. Optionally, the cyclic oligopeptide has the structure of Compound 2, as defined herein. The cyclic oligopeptide may have the structure of Compound 3, as defined herein. In some embodiments, the cyclic oligopeptide has the structure of Compound 4, as defined herein. Optionally, the cyclic oligopeptide has the structure of Compound 5, as defined herein. The cyclic oligopeptide may have the structure of Compound 6, as defined herein. In some embodiments, the cyclic oligopeptide has the structure of Compound 7, as defined herein. Optionally, the cyclic oligopeptide has the structure of Compound 8, as defined herein. The cyclic oligopeptide may have the structure of Compound 9, as defined herein. In some embodiments, the cyclic oligopeptide has the structure of Compound 10, as defined herein. Optionally, the cyclic oligopeptide has the structure of Compound 11, as defined herein.

In some embodiments, the cyclic oligopeptide is lipidated. In some embodiments, the cyclic oligopeptide is PEGylated.

A second aspect of the present disclosure provides a pharmaceutical formulation comprising a cyclic oligopeptide disclosed herein and a pharmaceutically acceptable carrier.

A third aspect of the present disclosure provides a method of treating or preventing an IL-13-associated skin disorder or condition in a subject in need thereof. In some embodiments, the method comprises administering to the subject a therapeutically effective amount of any one of the cyclic oligopeptides disclosed herein or a combination thereof. In some embodiments, the subject is a human.

In some embodiments, the IL 13 associated skin disorder or condition is an inflammatory, an allergic, or an autoimmune disorder or condition. In some embodiments, the IL 13 associated skin disorder or condition is selected from the group consisting of: atopic dermatitis, allergic contact dermatitis, urticaria, eczema, chronic hand eczema, bullous diseases (bullous pemphigoid), alopecia areata, prurigo and molluscum contagiosum. Optionally, the IL-13-associated skin disorder or condition is atopic dermatitis. The IL-13-associated skin disorder or condition may be allergic contact dermatitis. In some embodiments, the IL-13-associated skin disorder or condition is urticaria. Optionally, the IL-13-associated skin disorder or condition is eczema. The IL-13-associated skin disorder or condition may be chronic hand eczema. In some embodiments, the IL-13-associated skin disorder or condition is bullous diseases (bullous pemphigoid). Optionally, the IL-13-associated skin disorder or condition is alopecia areata. The IL-13-associated skin disorder or condition may be prurigo. In some embodiments, the IL-13-associated skin disorder or condition is molluscum contagiosum.

In some embodiments, the cyclic oligopeptide or combination thereof binds to IL-13 and reduces biological activities of IL-13 and/or an IL-13 receptor (IL-13R). In some embodiments, the cyclic oligopeptide or combination thereof binds to IL-13. In some embodiments, the cyclic oligopeptide or combination thereof reduces biological activities of IL-13 and/or an IL-13 receptor (IL-13R). In some embodiments, the cyclic oligopeptide or combination thereof reduces biological activities of IL-13. In some embodiments, the cyclic oligopeptide or combination thereof reduces biological activities of an IL-13 receptor (IL-13R). In some embodiments, the cyclic oligopeptide or combination thereof reduces biological activities of IL-13 and an IL-13 receptor (IL-13R).

In some embodiments, the cyclic oligopeptide or the combination thereof is administered topically. Optionally, the cyclic oligopeptide or the combination thereof is administered transdermally. In some embodiments, the cyclic oligopeptide or the combination thereof is administered subcutaneously. Optionally, the cyclic oligopeptide or the combination thereof is administered intravenously. In some embodiments, the cyclic oligopeptide or the combination thereof is administered orally.

A fourth aspect of the present disclosure provides a method of producing a cyclic oligopeptide binds to IL-13. In some embodiments, the method comprises the steps of: (1) contacting FMOC (9-fluorenylmethyloxycarbonyl)-D-Pro-2cl-resin or FMOC-Pro-2cl-resin with a first amino acid residue under conditions suitable to form a peptide bond between the first amino acid residue and the resin-bound D-Pro or Pro to form a resin-bound oligopeptide; (2) washing the resin-bound oligopeptide to remove any unbound amino acid residue; (3) contacting the resin-bound oligopeptide with an additional amino acid residue under conditions suitable to form a peptide bond between the additional amino acid residue and the resin-bound oligopeptide; (4) washing the resin-bound oligopeptide to remove any unbound amino acid residue; (5) removing the resin from the oligopeptide; and (6) cyclizing the oligopeptide.

In some embodiments, the conditions suitable to form a peptide bond in steps (1) and (3) include the addition of O-(Benzotriazol-1-yl)-N, N, N', N'-tetramethyluronium tetrafluoroborate (TBTU). Optionally, the conditions suitable to form a peptide bond in steps (1) and (3) further include the addition of N,N-Dimethylformamide (DMF) and N,N-Diisopropylethylamine (DIEA).

In some embodiments, steps (3) and (4) are repeated between 1 and 20 times before the resin is removed from the oligopeptide.

In some embodiments, the cyclizing step comprises the carboxyl group of the D-Pro or Pro residue forming a covalent bond with one or more amino groups of the linear oligopeptide. In some embodiments, the cyclizing step comprises the addition of DMF, PyBOP (Benzotriazol-1-yl-oxytripyrrolidinophosphonium hexafluorophosphate), HOBT (1-Hydroxybenzotriazole), and DIEA to the linear oligopeptide and incubation of the mixture thereof at room temperature.

In some embodiments, the cyclic oligopeptide that binds to IL-13 is a cyclic oligopeptide disclosed herein.

Particular embodiments of the disclosure are set forth in the following numbered paragraphs:
1. A cyclic oligopeptide that binds to IL-13.
2. The cyclic oligopeptide of embodiment 1, wherein the cyclic oligopeptide comprises between two and twenty-two amino acid residues.
3. The cyclic oligopeptide of embodiment 2, wherein the cyclic oligopeptide comprises between six and eight amino acid residues.
4. The cyclic oligopeptide of any one of embodiments 1-3, wherein the cyclic oligopeptide comprises a L-proline residue or a D-proline residue.
5. The cyclic oligopeptide of any one of embodiments 1-4, wherein the cyclic oligopeptide comprises an amino acid sequence selected from the group consisting of SEQ ID NOs: 1-11.
6. The cyclic oligopeptide of embodiment 5, wherein the cyclic oligopeptide comprises the amino acid sequence of D-ARG D-PHE D-VAL TYR GLU PRO (SEQ ID NO:1).
7. The cyclic oligopeptide of embodiment 5, wherein the cyclic oligopeptide comprises the amino acid sequence of ARG THR D-VAL GLU D-PHE D-PRO (SEQ ID NO:2).
8. The cyclic oligopeptide of embodiment 5, wherein the cyclic oligopeptide comprises the amino acid sequence of GLU D-THR D-VAL TRP D-PRO D-PRO (SEQ ID NO:3).

9. The cyclic oligopeptide of embodiment 5, wherein the cyclic oligopeptide comprises the amino acid sequence of ARG GLU D-VAL TRP D-PRO D-PRO (SEQ ID NO:4).
10. The cyclic oligopeptide of embodiment 5, wherein the cyclic oligopeptide comprises the amino acid sequence of TRP VAL ARG GLU D-PRO D-PRO (SEQ ID NO:5).
11. The cyclic oligopeptide of embodiment 5, wherein the cyclic oligopeptide comprises the amino acid sequence of TYR ARG GLU D-THR D-VAL D-PRO (SEQ ID NO:6).
12. The cyclic oligopeptide of embodiment 5, wherein the cyclic oligopeptide comprises the amino acid sequence of THR ARG D-PHE PRO D-LEU D-PRO (SEQ ID NO:7).
13. The cyclic oligopeptide of embodiment 5, wherein the cyclic oligopeptide comprises the amino acid sequence of D-LEU ARG GLU PRO TRP MET PRO (SEQ ID NO:8).
14. The cyclic oligopeptide of embodiment 5, wherein the cyclic oligopeptide comprises the amino acid sequence of D-ARG LEU D-TRP TRP D-THR GLU PRO (SEQ ID NO:9).
15. The cyclic oligopeptide of embodiment 5, wherein the cyclic oligopeptide comprises the amino acid sequence of ARG ASP TYR CYS D-PRO D-TRP D-PRO (SEQ ID NO:10).
16. The cyclic oligopeptide of embodiment 5, wherein the cyclic oligopeptide comprises the amino acid sequence of VAL PRO D-LEU D-TRP D-VAL LEU ARG PRO (SEQ ID NO:11).
17. The cyclic oligopeptide of embodiment 1, wherein the cyclic oligopeptide has the structure of any one of Compounds 1-11, as defined herein.
18. The cyclic oligopeptide of embodiment 17, wherein the cyclic oligopeptide has the structure of Compound 1, as defined herein.
19. The cyclic oligopeptide of embodiment 17, wherein the cyclic oligopeptide has the structure of Compound 2, as defined herein.
20. The cyclic oligopeptide of embodiment 17, wherein the cyclic oligopeptide has the structure of Compound 3, as defined herein.
21. The cyclic oligopeptide of embodiment 17, wherein the cyclic oligopeptide has the structure of Compound 4, as defined herein.
22. The cyclic oligopeptide of embodiment 17, wherein the cyclic oligopeptide has the structure of Compound 5, as defined herein.
23. The cyclic oligopeptide of embodiment 17, wherein the cyclic oligopeptide has the structure of Compound 6, as defined herein.
24. The cyclic oligopeptide of embodiment 17, wherein the cyclic oligopeptide has the structure of Compound 7, as defined herein.
25. The cyclic oligopeptide of embodiment 17, wherein the cyclic oligopeptide has the structure of Compound 8, as defined herein.
26. The cyclic oligopeptide of embodiment 17, wherein the cyclic oligopeptide has the structure of Compound 9, as defined herein.
27. The cyclic oligopeptide of embodiment 17, wherein the cyclic oligopeptide has the structure of Compound 10, as defined herein.
28. The cyclic oligopeptide of embodiment 17, wherein the cyclic oligopeptide has the structure of Compound 11, as defined herein.
29. The cyclic oligopeptide of any one of embodiments 1-28, wherein the cyclic oligopeptide is lipidated.
30. The cyclic oligopeptide of any one of embodiments 1-28, wherein the cyclic oligopeptide is PEGylated.
31. A pharmaceutical formulation comprising a cyclic oligopeptide of any one of embodiments 1-30 and a pharmaceutically acceptable carrier.
32. A method of treating or preventing an IL-13-associated skin disorder or condition in a subject in need thereof, comprising administering to the subject a therapeutically effective amount of any one of the cyclic oligopeptides of embodiments 1-30 or a combination thereof.
33. The method of embodiment 32, wherein the subject is a human.
34. The method of embodiment 32 or 33, wherein the cyclic oligopeptide comprises an amino acid sequence selected from the group consisting of SEQ ID NO:1-11.
35. The method of embodiment 32-34, wherein the cyclic oligopeptide has the structure of any one of Compounds 1-11.
36. The method of any one of embodiments 32-35, wherein the IL-13-associated skin disorder or condition is an inflammatory, an allergic, or an autoimmune disorder or condition.
37. The method of any one of embodiments 32-35, wherein the IL-13-associated skin disorder or condition is selected from the group consisting of: atopic dermatitis, allergic contact dermatitis, urticaria, eczema, chronic hand eczema, bullous diseases (bullous pemphigoid), alopecia areata, prurigo and molluscum contagiosum.
38. The method of any one of embodiments 32-35, wherein the IL-13-associated skin disorder or condition is atopic dermatitis.
39. The method of any one of embodiments 32-35, wherein the IL-13-associated skin disorder or condition is allergic contact dermatitis.
40. The method of any one of embodiments 32-35, wherein the IL-13-associated skin disorder or condition is urticaria.
41. The method of any one of embodiments 32-35, wherein the IL-13-associated skin disorder or condition is eczema.
42. The method of any one of embodiments 32-35, wherein the IL-13-associated skin disorder or condition is chronic hand eczema.
43. The method of any one of embodiments 32-35, wherein the IL-13-associated skin disorder or condition is bullous diseases (bullous pemphigoid).
44. The method of any one of embodiments 32-35, wherein the IL-13-associated skin disorder or condition is alopecia areata.
45. The method of any one of embodiments 32-35, wherein the IL-13-associated skin disorder or condition is prurigo.
46. The method of any one of embodiments 32-35, wherein the IL-13-associated skin disorder or condition is molluscum contagiosum.
47. The method of any one of embodiments 32-46, wherein the cyclic oligopeptide or combination thereof binds to IL-13 and reduces biological activities of IL-13 and/or an IL-13 receptor (IL-13R).

48. The method of any one of embodiments 32-47, wherein the cyclic oligopeptide or the combination thereof is administered topically.
49. The method of any one of embodiments 32-47, wherein the cyclic oligopeptide or the combination thereof is administered transdermally.
50. The method of any one of embodiments 32-47, wherein the cyclic oligopeptide or the combination thereof is administered subcutaneously.
51. The method of any one of embodiments 32-47, wherein the cyclic oligopeptide or the combination thereof is administered intravenously.
52. A method of producing a cyclic oligopeptide binds to IL-13 comprising the steps of:
    (1) contacting FMOC (9-fluorenylmethyloxycarbonyl)-D-Pro-2cl-resin or FMOC-Pro-2cl-resin with a first amino acid residue under conditions suitable to form a peptide bond between the first amino acid residue and the resin-bound D-Pro or Pro to form a resin-bound oligopeptide;
    (2) washing the resin-bound oligopeptide to remove any unbound amino acid residue;
    (3) contacting the resin-bound oligopeptide with an additional amino acid residue under conditions suitable to form a peptide bond between the additional amino acid residue and the resin-bound oligopeptide;
    (4) washing the resin-bound oligopeptide to remove any unbound amino acid residue;
    (5) removing the resin from the oligopeptide; and
    (6) cyclizing the oligopeptide.
53. The method of embodiment 52, wherein the conditions suitable to form a peptide bond in steps (1) and (3) include the addition of O-(Benzotriazol-1-yl)-N, N, N', N'-tetramethyluronium tetrafluoroborate (TBTU).
54. The method of embodiment 53, wherein the conditions suitable to form a peptide bond in steps (1) and (3) further include the addition of N,N-Dimethylformamide (DMF) and N,N-Diisopropylethylamine (DIEA).
55. The method of any one of embodiments 52-54, wherein steps (3) and (4) are repeated between 1 and 20 times before the resin is removed from the oligopeptide.
56. The method of any one of embodiments 52-55, wherein the cyclizing step comprises the carboxyl group of the D-Pro or Pro residue forming a covalent bond with one or more amino groups of the linear oligopeptide.
57. The method of embodiment 52, wherein the cyclizing step comprises the addition of DMF, PyBOP (Benzotriazol-1-yl-oxytripyrrolidinophosphonium hexafluorophosphate), HOBT (1-Hydroxybenzotriazole), and DIEA to the linear oligopeptide and incubation of the mixture thereof at room temperature.
58. The method of any one of embodiments 52-57, wherein the cyclic oligopeptide binds to IL-13 is a cyclic oligopeptide according to any one of embodiments 1-30.
59. The cyclic oligopeptide of any one of embodiments 1-30, wherein the cyclic oligopeptide has a skin permeation rate of at least 25% after 24 hours.
60. The cyclic oligopeptide of any one of embodiments 1-30, wherein the cyclic oligopeptide has a skin permeation rate of at least 30% after 24 hours.
61. The cyclic oligopeptide of any one of embodiments 1-30, wherein the cyclic oligopeptide has a skin permeation rate of at least 35% after 24 hours.
62. The cyclic oligopeptide of any one of embodiments 1-30, wherein the cyclic oligopeptide has a skin permeation rate of at least 40% after 24 hours.
63. The cyclic oligopeptide of any one of embodiments 1-30, wherein the cyclic oligopeptide has a skin permeation rate of at least 45% after 24 hours.
64. The cyclic oligopeptide of any one of embodiments 1-30, wherein the cyclic oligopeptide has a skin permeation rate of at least 50% after 24 hours.
65. The cyclic oligopeptide of any one of embodiments 1-30, wherein the cyclic oligopeptide has a skin permeation rate of at least 55% after 24 hours.
66. The cyclic oligopeptide of any one of embodiments 1-30, wherein the cyclic oligopeptide has a skin permeation rate of at least 60% after 24 hours.
67. The cyclic oligopeptide of any one of embodiments 1-30, wherein the cyclic oligopeptide has a skin permeation rate of at least 10% after 1 hour.
68. The cyclic oligopeptide of any one of embodiments 1-30, wherein the cyclic oligopeptide has a skin permeation rate of at least 15% after 1 hour.
69. The cyclic oligopeptide of any one of embodiments 1-30, wherein the cyclic oligopeptide has a skin permeation rate of at least 20% after 1 hour.
70. The cyclic oligopeptide of any one of embodiments 1-30, wherein the cyclic oligopeptide has a skin permeation rate of at least 25% after 1 hour.
71. The cyclic oligopeptide of any one of embodiments 1-30, wherein the cyclic oligopeptide has an average skin permeability coefficient of at least $1.0\times10^{-5}$ cm/hr after 24 hours.
72. The cyclic oligopeptide of any one of embodiments 1-30, wherein the cyclic oligopeptide has an average skin permeability coefficient of at least $2.0\times10^{-5}$ cm/hr after 24 hours.
73. The cyclic oligopeptide of any one of embodiments 1-30, wherein the cyclic oligopeptide has an average skin permeability coefficient of at least $5.0\times10^{-5}$ cm/hr after 24 hours.
74. The cyclic oligopeptide of any one of embodiments 1-30, wherein the cyclic oligopeptide has an average skin permeability coefficient of at least $1.0\times10^{-4}$ cm/hr after 24 hours.
75. The cyclic oligopeptide of any one of embodiments 1-30, wherein the cyclic oligopeptide has an average skin permeability coefficient of at least $1.0\times10^{-2}$ cm/hr after 1 hour.
76. The cyclic oligopeptide of any one of embodiments 1-30, wherein the cyclic oligopeptide has an average skin permeability coefficient of at least $2.0\times10^{-2}$ cm/hr after 1 hour.
77. The cyclic oligopeptide of any one of embodiments 1-30, wherein the cyclic oligopeptide has an average skin permeability coefficient of at least $3.0\times10^{-2}$ cm/hr after 1 hour.
78. The cyclic oligopeptide of any one of embodiments 1-30, wherein the cyclic oligopeptide has an average skin permeability coefficient of at least $4.0\times10^{-2}$ cm/hr after 1 hour.
79. The cyclic oligopeptide of any one of embodiments 1-30 and 59-78, wherein the cyclic oligopeptide is fast-acting after topical application.
80. The cyclic oligopeptide of any one of embodiments 1-30 and 59-78, wherein the cyclic oligopeptide is suitable for long-term delivery after topical application.

BRIEF DESCRIPTION OF THE DRAWINGS

FIG. A-1K depict chemical structures of exemplary cyclic oligopeptides of this disclosure, Compounds 1-11, respectively.

FIG. 10E illustrates average permeability coefficient (Kp) of Compound 9 for 1, 2, 4, 8, 12 and 24 hours.

FIG. 12E illustrates average permeability coefficient (Kp) of Compound 11 for 1, 2, 4, 8, 12 and 24 hours.

DETAILED DESCRIPTION OF THE DISCLOSURE

Figure 1A:
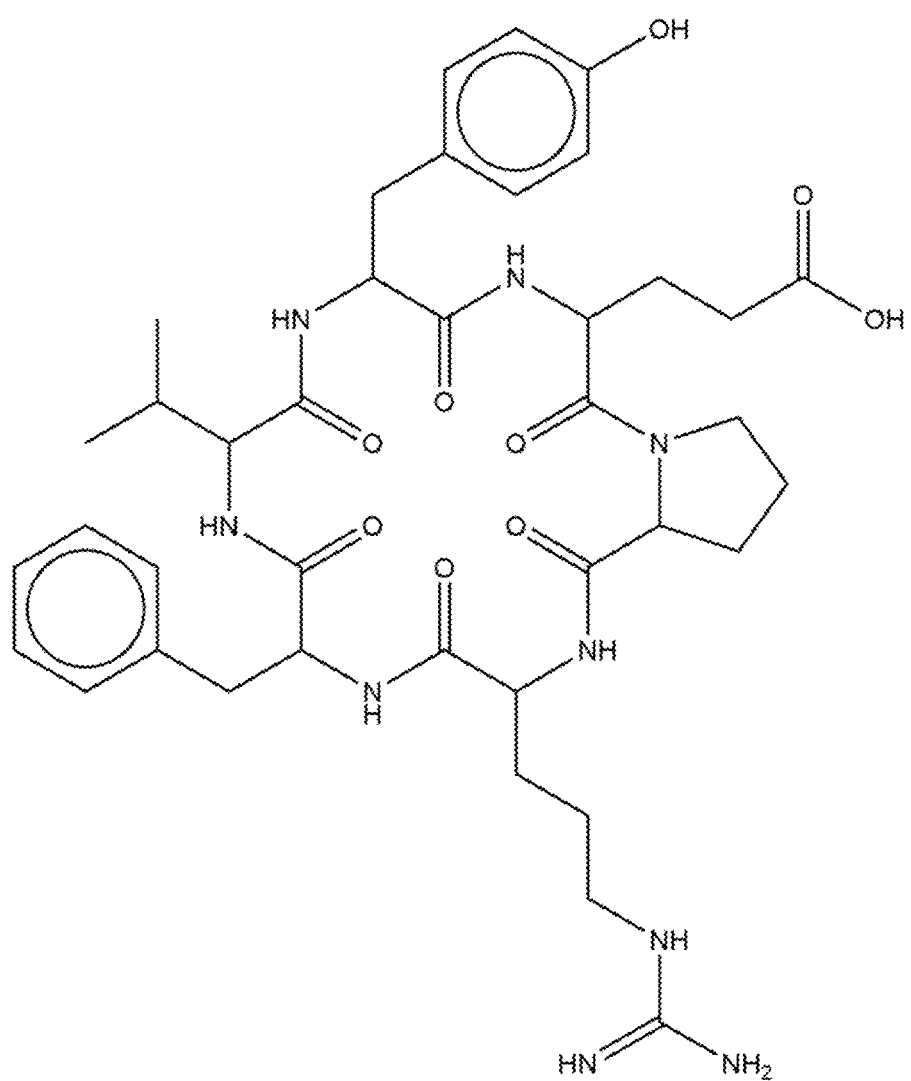
Figure 1B:
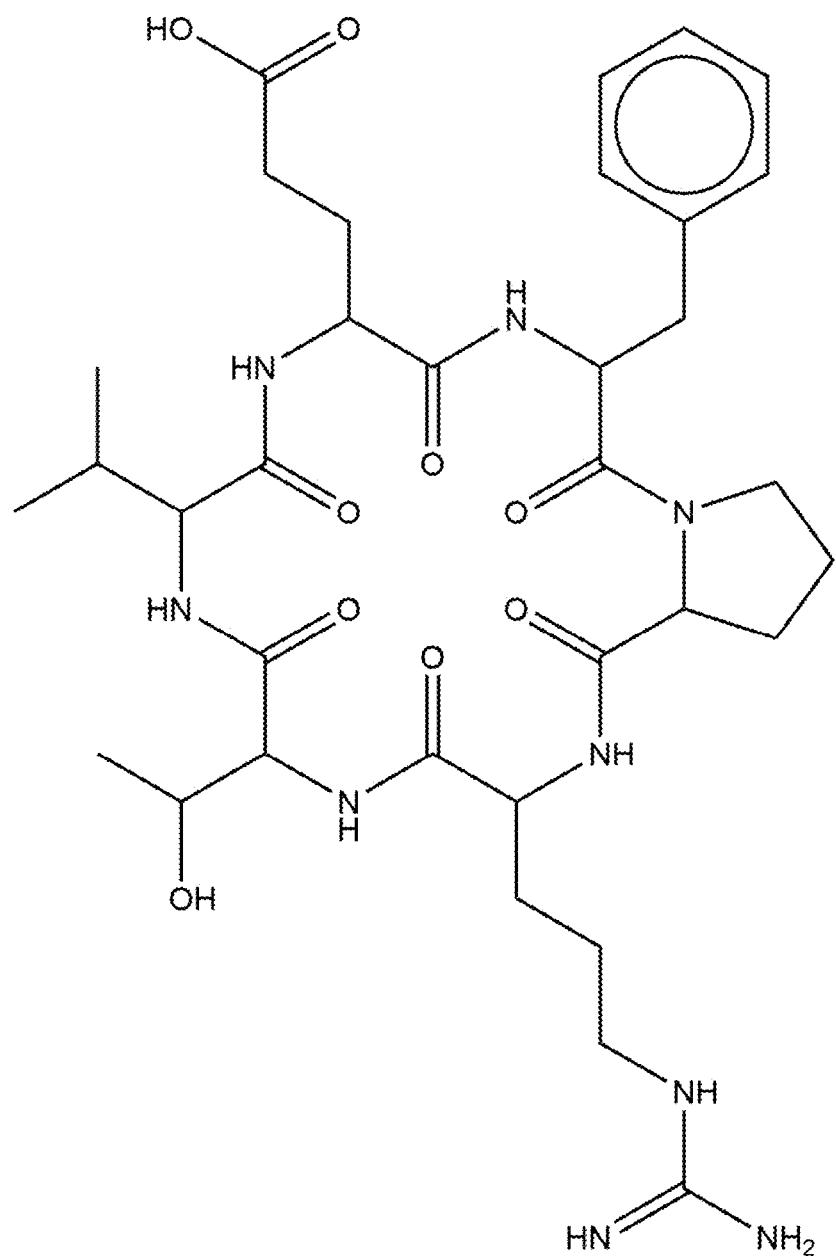
Figure 1C:
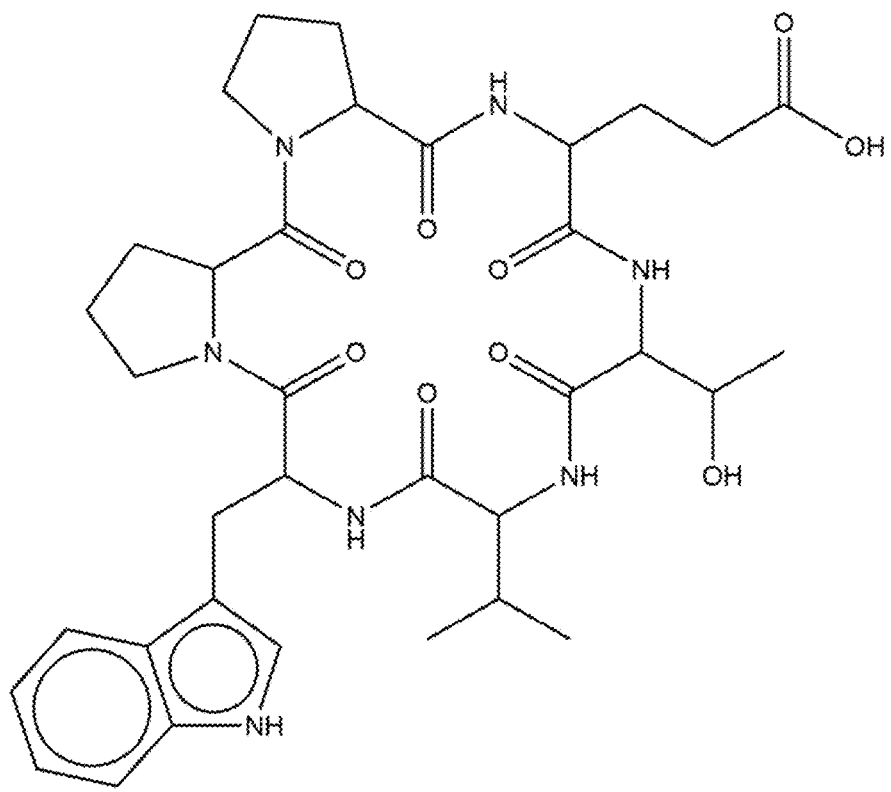
Figure 1D:
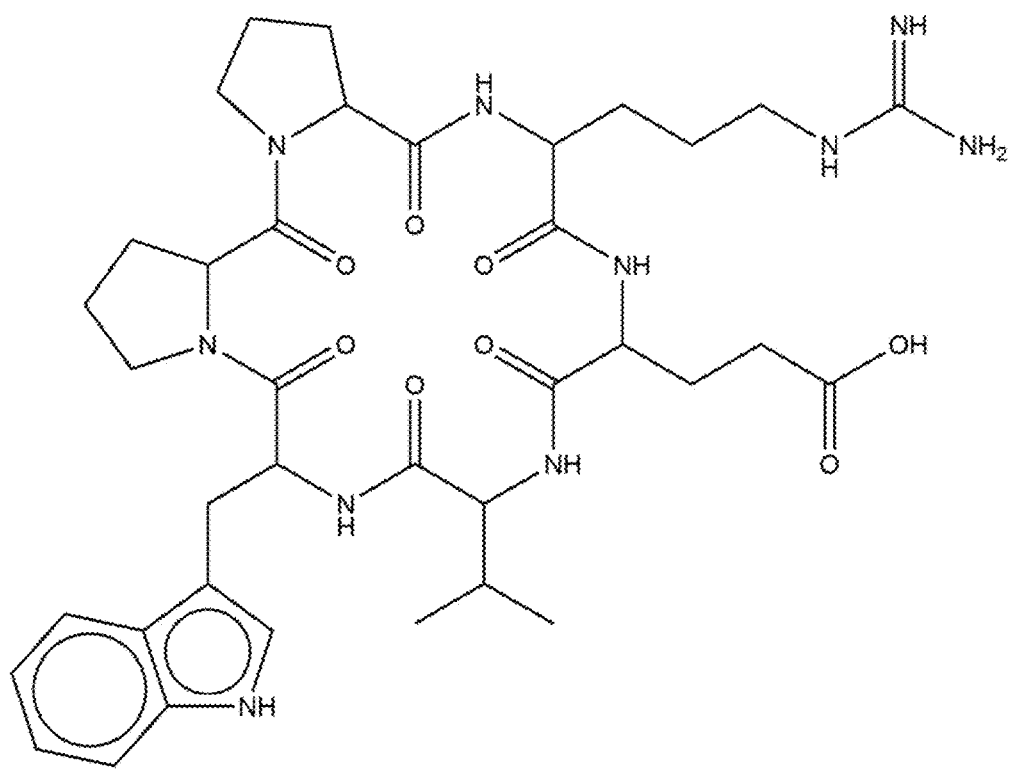
Figure 1E:
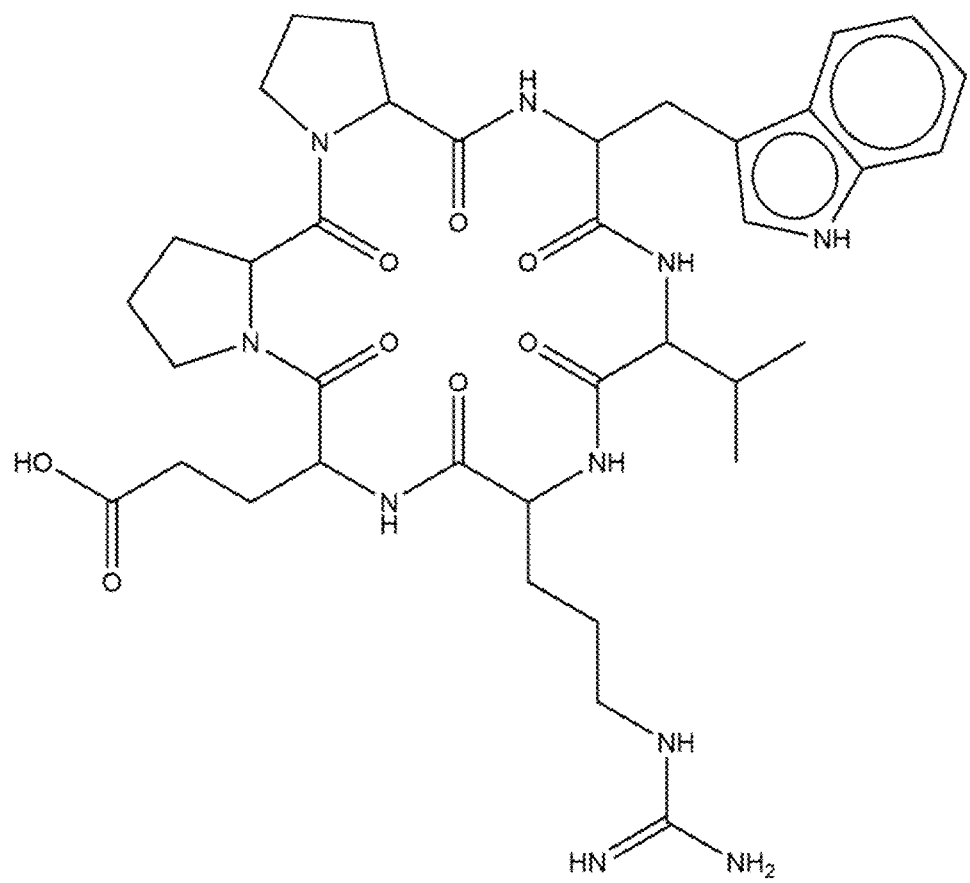
Figure 1F:
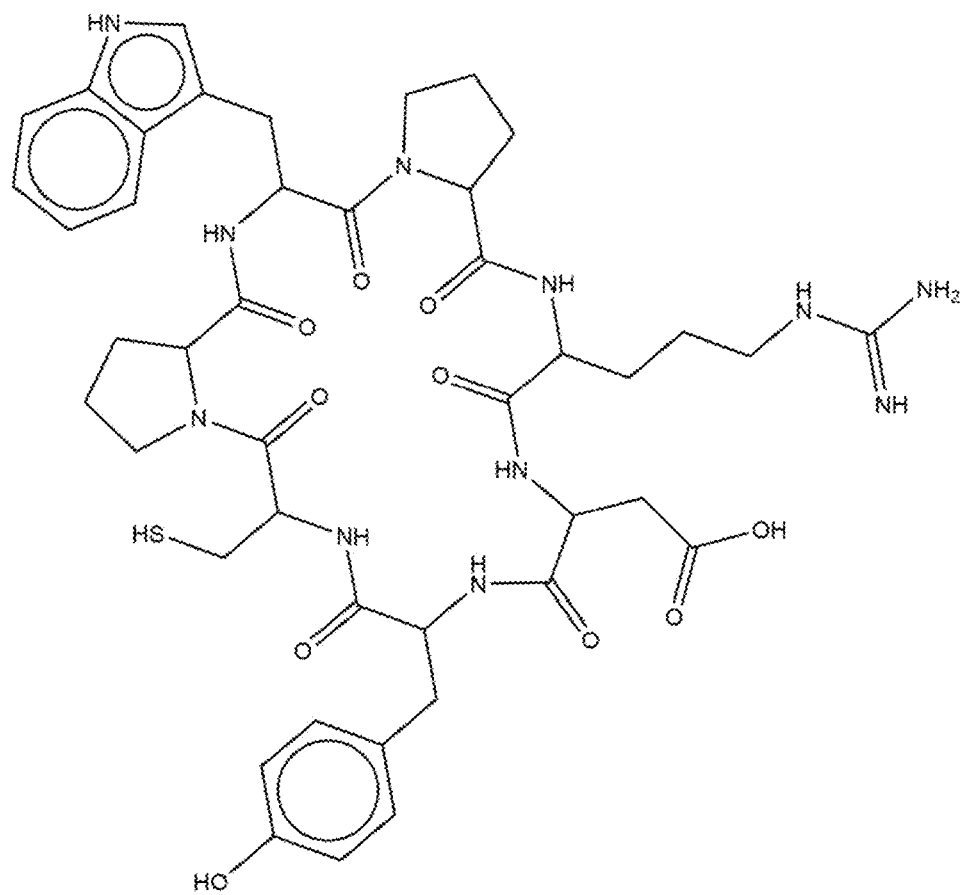
Figure 1G:
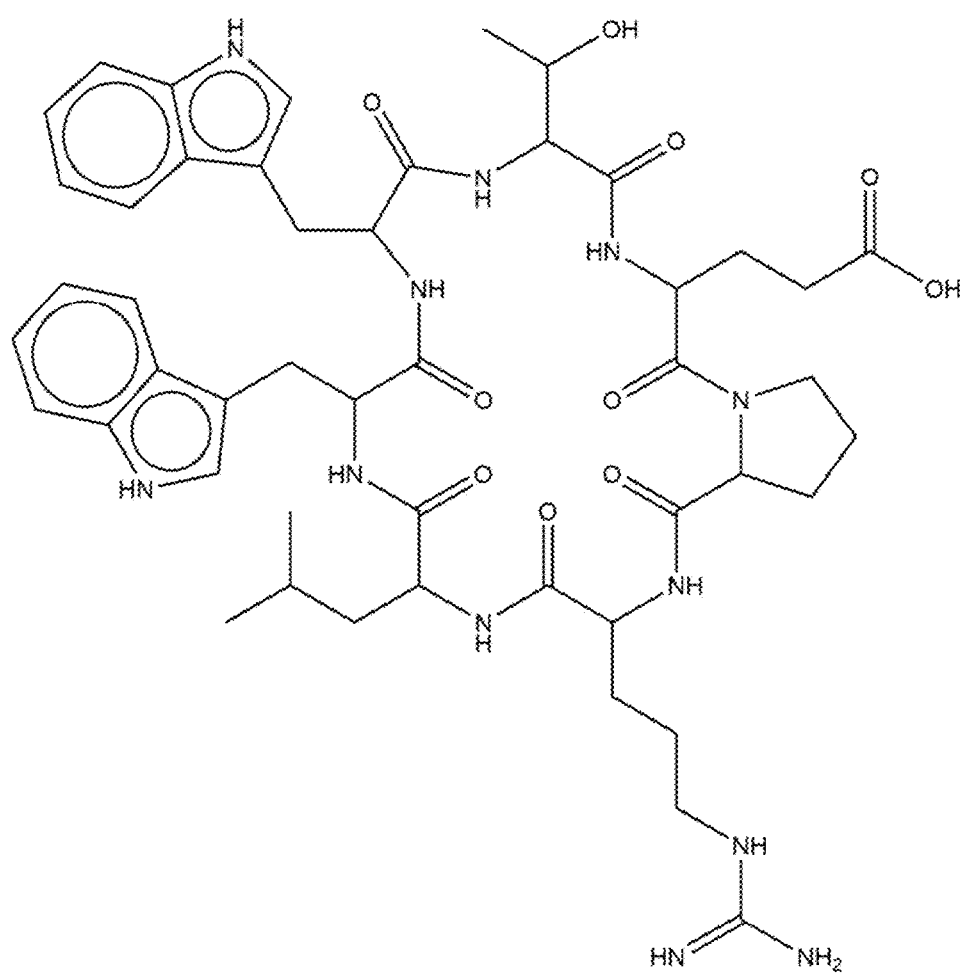
Figure 1H:
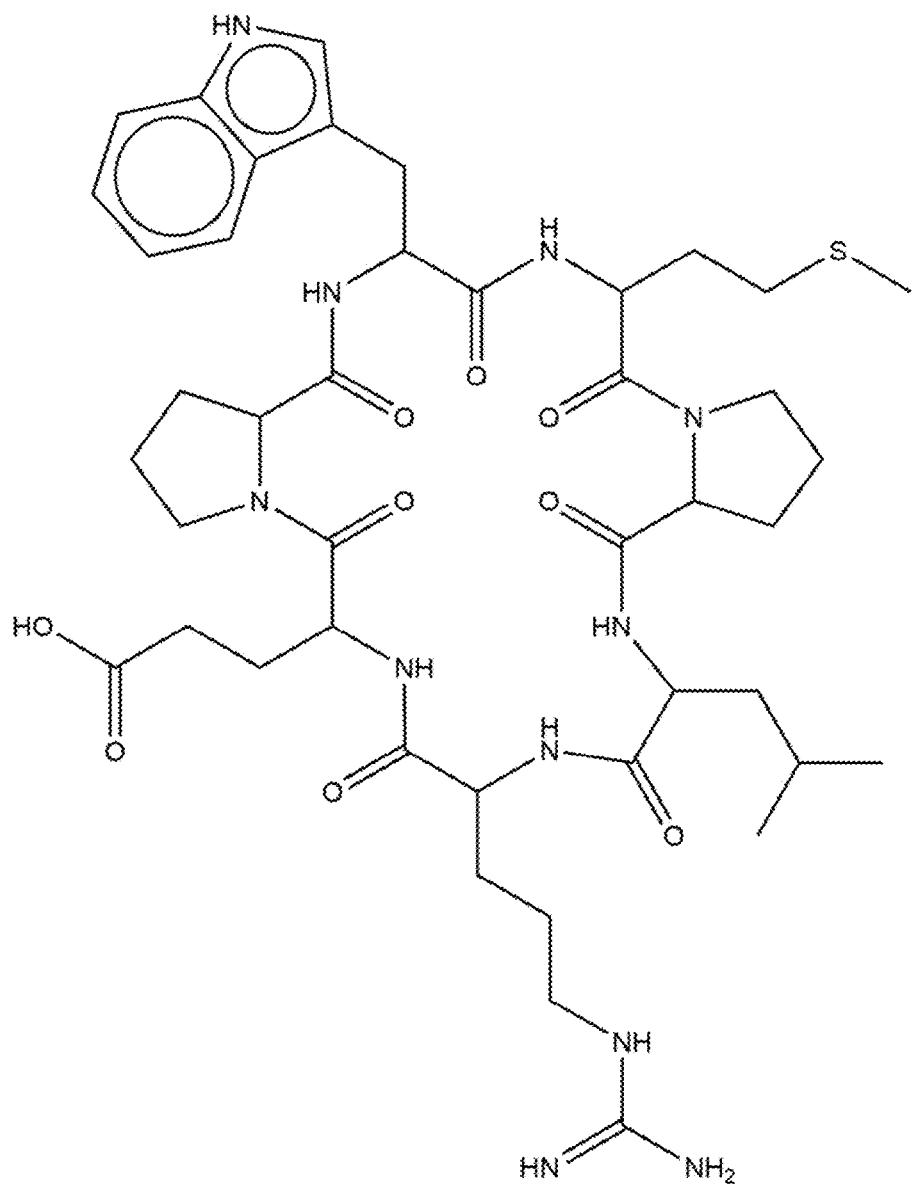
Figure 1I:
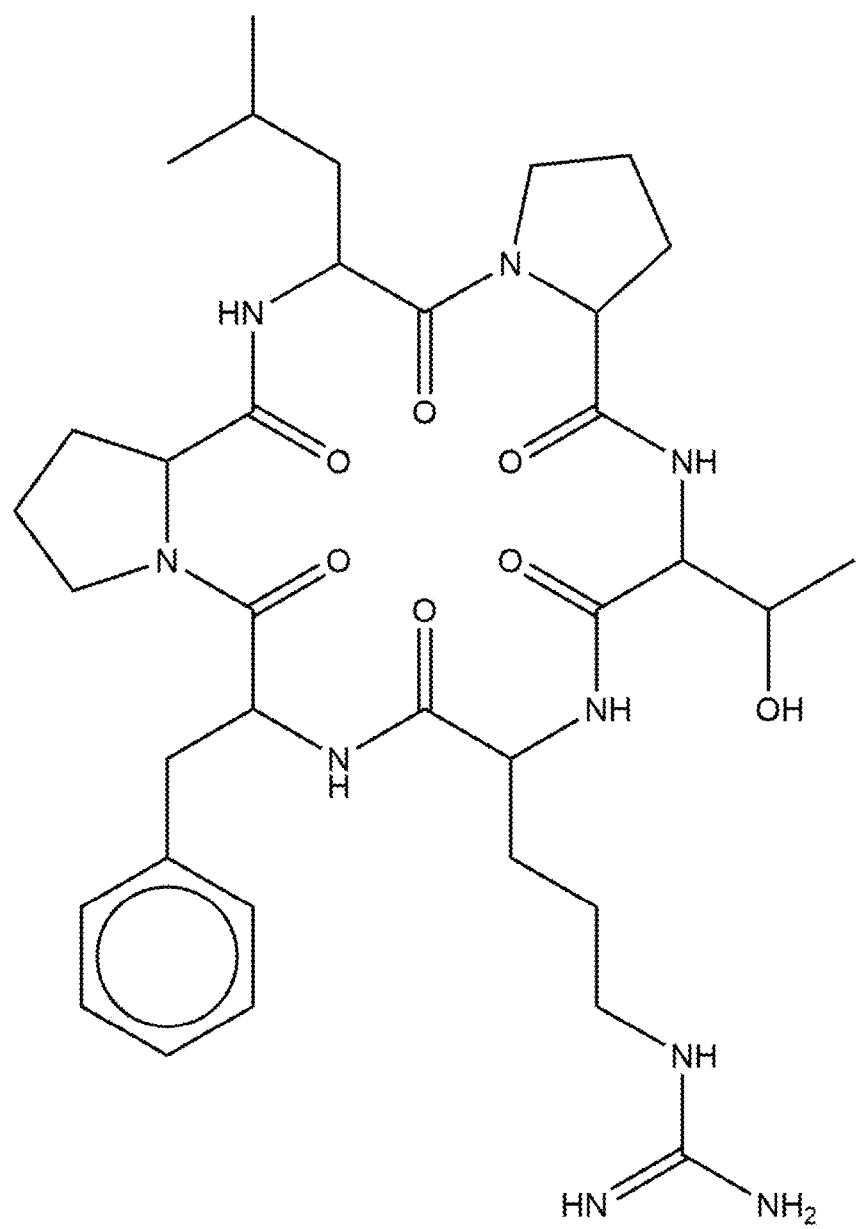
Figure 1J:
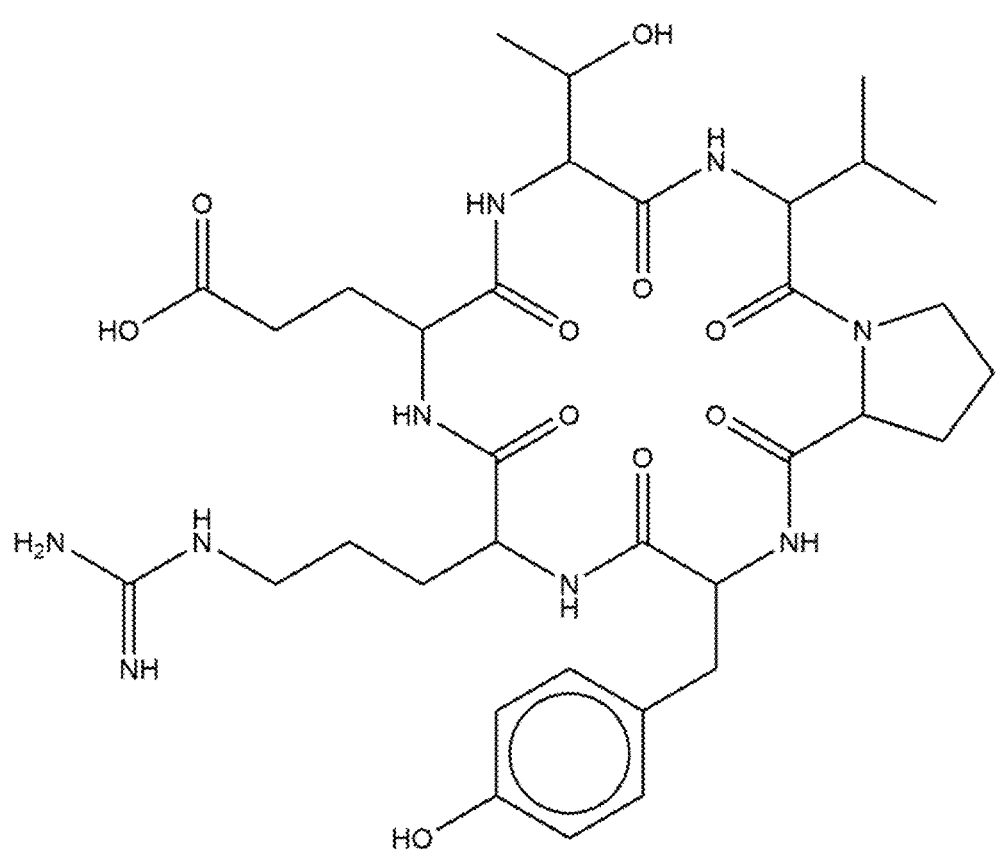
Figure 1K:
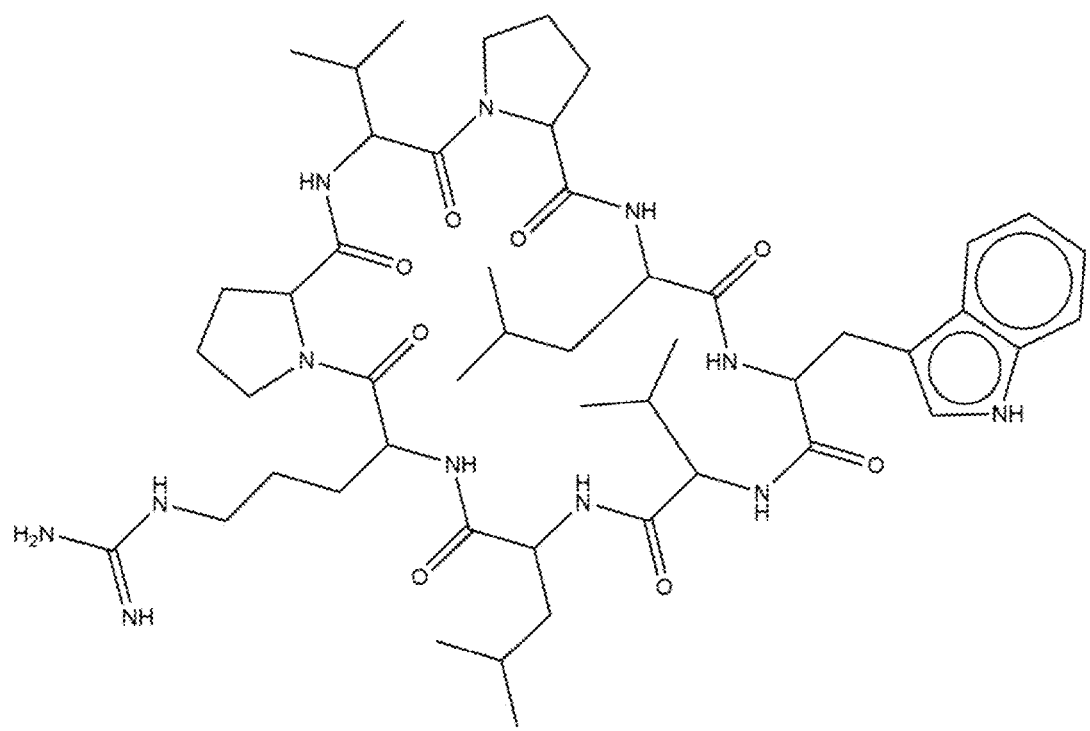

Unless otherwise defined herein, scientific and technical terms used in this application shall have the meanings that are commonly understood by those of ordinary skill in the art. In case of conflict, the present specification, including definitions, will control.

It should be understood that any of the embodiments described herein, including those described under different aspects of the disclosure and different parts of the specification (including embodiments described only in the Examples) can be combined with one or more other embodiments of this disclosure, unless explicitly disclaimed or improper. Combination of embodiments are not limited to those specific combinations claimed via the multiple dependent claims.

All of the publications, patents and published patent applications referred to in this application are specifically incorporated by reference in their entirety. In case of conflict, the present specification, including its specific definitions, will control.

Where aspects or embodiments are described in terms of a Markush group or other grouping of alternatives, the present application encompasses not only the entire group listed as a whole, but each member of the group individually and all possible subgroups of the main group, and also the main group absent one or more of the group members.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout the specification, where compositions are described as having, including, or comprising (or variations thereof), specific components, it is contemplated that compositions also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "including," as used herein, means "including but not limited to." "Including" and "including but not limited to" are used interchangeably. Thus, these terms will be understood to imply the inclusion of a stated integer (or components) or group of integers (or components), but not the exclusion of any other integer (or components) or group of integers (or components).

Any example(s) following the term "e.g." or "for example" is not meant to be exhaustive or limiting.

Unless otherwise required by context, singular terms shall include pluralities and plural terms shall include the singular.

The articles "a," "an" and "the" are used herein to refer to one or to more than one (i.e., to at least one) of the grammatical object of the article.

Notwithstanding that the disclosed numerical ranges and parameters are approximations, the numerical values set forth in the specific examples are reported as precisely as possible. Any numerical value, however, inherently contains certain errors necessarily resulting from the standard deviation found in their respective testing measurements. Accordingly, as used herein, the term "about" permits a variation of 10%. As used herein, the term "about" refers to a value or parameter that includes (and describes) embodiments that are directed to that value or parameter per se. Moreover, all ranges disclosed herein are to be understood to encompass any and all subranges subsumed therein. For example, a stated range of "1 to 10" should be considered to include any and all subranges and individual numbers between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10 or individual numbers within a stated range or subrange, e.g., 2, 5, 8 or 10.

As used herein, amino acids having L-configuration are represented using standard three letter codes, e.g. Ala for alanine, Gly for glycine, Val for valine, Leu for leucine, Ile for isoleucine, Pro for proline, Ser for serine, Thr for threonine, Asn for asparagine, Gln for glutamine, Cys for cysteine, Met for methionine, Phe for phenylalanine, Tyr for tyrosine, Trp for tryptophan, Asp for Aspartate, Glu for glutamate, His for histidine, Lys for lysine and Arg for arginine. As used herein, amino acids having D-configuration are represented by adding "D-" before the standard three letter codes, e.g. D-Ala for D-alanine, D-Gly for D-glycine, D-Val for D-valine, D-Leu for D-leucine, D-Ile for D-isoleucine, D-Pro for D-proline, D-Ser for D-serine, D-Thr for D-threonine, D-Asn for D-asparagine, D-Gln for D-glutamine, D-Cys for D-cysteine, D-Met for D-methionine, D-Phe for D-phenylalanine, D-Tyr for D-tyrosine, D-Trp for D-tryptophan, D-Asp for D-Aspartate, D-Glu for D-glutamate, D-His for D-histidine, D-Lys for D-lysine and D-Arg for D-arginine.

Definitions

In order that the disclosure may be more readily understood, certain terms are first defined. These definitions should be read in light of the remainder of the disclosure, as understood by a person of ordinary skill in the art. Unless defined otherwise, all technical and scientific terms used herein have the same meaning as commonly understood by a person of ordinary skill in the art.

As used herein, the terms "administer" and "administration" include any suitable route for providing the subject with the cyclic oligopeptides or pharmaceutical compositions of the disclosure for treatment of a skin disorder or condition, such as an IL-13 associated skin disorder or condition. For example, the cyclic oligopeptide or pharmaceutical composition may be administered topically, transdermally, subcutaneously, intravenously or orally. Dosage forms useful in the methods of this disclosure may include films, dispersions, suspensions, solutions, ointments, lotions, creams, powders, drops (e.g. eye or ear drops), sprays, patches and the like. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. When a method is part of a therapeutic regimen involving more than one pharmaceutical composition or treatment modality, the disclosure contemplates that the pharmaceutical compositions may be administered at the same or differing times and via the same or differing routes of administration.

As used herein, the terms "bind" and "binding" refer to molecular binding of two or more molecules, e.g. IL-13 and cyclic oligopeptide, which is an attractive interaction between the two or more molecules that results in a stable association in which the molecules are in close proximity to each other. The strength of molecular binding or the affinity among the binding molecules in this disclosure can be quantified by, for example, a Surface Plasmon Resonance (SPR) assay.

As used herein, the term "cyclic oligopeptide" refers to oligopeptide chains which contain a circular sequence of bonds. Cyclic oligopeptides are typically first generated as linear oligopeptides and then cyclized, e.g., by chemical or enzymatic means. The circular sequence of bonds can be formed by, for example, a connection between the amino and carboxyl ends of the linear oligopeptide, a connection between the amino end of the linear oligopeptide and a side chain of one of the amino acid residues in the oligopeptide, a connection between the carboxyl end of the linear oligopeptide and a side chain of one of the amino acid residues in the oligopeptide, and/or the side chains of two different amino acid residues in the oligopeptide. The length of a cyclic oligopeptide of this disclosure ranges from two amino acid residues to twenty amino acid residues. In some embodiments, the length of a cyclic oligopeptide of this disclosure ranges from four amino acid residues to ten amino acid residues. In some embodiments, the length of a cyclic oligopeptide of this disclosure ranges from six amino acid residues to ten amino acid residues.

The term "dosage unit form" as used herein refers to physically discrete units suited as unitary dosages for the mammalian subjects to be treated; each unit containing a predetermined quantity of active compound calculated to produce the desired therapeutic effect in association with the required pharmaceutical carrier.

As used herein, the terms "Interleukin-13" and "IL-13" refer to a protein that in humans is encoded by the IL13 gene or a protein encoded by a homologous gene of human IL13 gene in a non-human species.

As used herein, the term "IL-13-associated skin disorder or condition" refers to a skin disease, a skin disorder or a skin condition that is associated dysfunction of IL-13 involved immune regulations. An IL-13-associated skin disorder or condition may be an inflammatory, an allergic, or an autoimmune disorder or condition. Non-limiting examples of IL-13-associated skin disorders or conditions include atopic dermatitis, allergic contact dermatitis, urticaria, eczema, chronic hand eczema, bullous diseases (bullous pemphigoid), alopecia areata, prurigo and molluscum contagiosum.

The terms "oligopeptide" refers to a polymer of amino acid residues. The term also applies to amino acid polymers in which one or more amino acids are chemical analogues or modified derivatives of a corresponding naturally-occurring amino acids.

As used herein, "pharmaceutically acceptable carrier" and "pharmaceutically acceptable excipient" are used interchangeably refer to any and all solvents, dispersion media, coatings, antibacterial and antifungal agents, isotonic and absorption delaying agents, and the like that are physiologically compatible. Pharmaceutically acceptable carriers are well known in the art. See, e.g., Remington's Pharmaceutical Sciences and U.S. Pharmacopeia: National Formulary, Mack Publishing Company, Easton, PA (1984), incorporated herein by reference. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives, or buffers, which enhance the shelf life or effectiveness of the antibody. Pharmaceutical compositions may be prepared by mixing an antibody disclosed herein with acceptable carriers, excipients, or stabilizers in the form of, e.g., lyophilized powders, slurries, aqueous solutions or suspensions (see, e.g., Brunton et al. (eds.), Goodman and Gilman's The Pharmacological Basis of Therapeutics, Thirteenth Edition, (2018) McGraw-Hill, New York, NY; Adejare, A. (ed.), Remington: The Science and Practice of Pharmacy, Twenty-Third Edition, (2020) Academic Press, New York, NY; Nema, et al. (eds.), Pharmaceutical Dosage Forms: Parenteral Medications, Third Edition, (2010) Informa Healthcare, NY, Augsburger et al. (eds.), Pharmaceutical Dosage Forms: Tablets, Third Edition (2008) CRC Press, NY; Lieberman, et al. (eds.) Pharmaceutical Dosage Forms: Disperse Systems, Second Edition, (2010) Informa Helathcare, NY; Weiner and Kotkoskie, Excipient Toxicity and Safety, (2007) Informa Healthcare, New York, NY; each incorporated herein by reference).

As used herein, the term "pharmaceutically acceptable salt" refers to those salts which are suitable for pharmaceutical use, such as, for example, for use in humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in *J Pharmaceutical Sciences*, 66: 1-19 (1977), incorporated herein by reference. The salts can be prepared in situ during the final isolation and purification of the cyclic oligopeptides disclosed herein, or separately by reacting a free base or free acid function with a suitable reagent, as described generally below. For example, a free base function can be reacted with a suitable acid. Suitable pharmaceutically acceptable salts can, include metal salts such as alkali metal salts, e.g., sodium, potassium, and lithium salts; and alkaline earth metal salts, e.g., calcium or magnesium salts. Examples of pharmaceutically acceptable, nontoxic acid addition salts are salts of an amino group formed with inorganic acids such as hydrochloric acid, hydrobromic acid, hydroiodic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

The term "residue," as used herein, refers to a position in an oligopeptide and its associated amino acid identity.

The terms "subject," "patient" and "individual" are used interchangeably and refer to mammals including, but not limited to, human patients and non-human primates, as well as experimental animals such as rabbits, dogs, cats, rats, mice, and other animals. Accordingly, the term "subject" or "patient" as used herein means any mammalian patient or subject to which the cyclic oligopeptides or related compositions of the disclosure can be administered. In some embodiments, the subject is a human patient. Subjects of the present invention include those with an IL-13-associated disorder or condition.

The terms "therapeutically effective amount," or "therapeutically effective dose" refer to an amount of a cyclic oligopeptide of the disclosure that will relieve, to some extent, one or more of the symptoms of an IL-13-associated skin disease or condition in a patient, e.g., effecting a beneficial and/or desirable alteration in the general health of a patient suffering from an IL-13-associated skin disorder or condition, as described herein. The full therapeutic effect does not necessarily occur by administration of one dose and may occur only after administration of a series of doses. Thus, a therapeutically effective amount may be administered in one or more administrations. The precise effective amount needed for a subject will depend upon, for example, the subject's size, health and age, the nature and extent of disease, the therapeutics or combination of therapeutics selected for administration, and the mode of administration. The skilled worker can readily determine the effective amount for a given situation by routine experimentation. The therapeutic methods or methods of treating described herein are not to be interpreted as or otherwise limited to "curing" the disease.

As used herein, the term "treat" and its cognates refer to reversing, reducing, or arresting the symptoms, clinical signs, and underlying pathology of an IL-13-associated skin disease or condition in manner to improve or stabilize a subject's condition. As used herein, and as well understood in the art, "treatment" is an approach for obtaining beneficial or desired results, including clinical results. Beneficial or desired results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (partially or completely). In some embodiments, the term "treat atopic dermatitis" refers to an approach for obtaining one or more beneficial or desired results including but not limited to, alleviation or amelioration of dry skin, itching, red to brownish-gray patches, small, raised bumps, thickened, cracked, scaly skin, and raw, sensitive, swollen skin from scratching. In some embodiments, the term "treat atopic dermatitis" refers to an approach to diminish extent of one or more symptoms of atopic dermatitis, wherein the one or more symptoms include but are not limited to dry skin, itching, red to brownish-gray patches, small, raised bumps, thickened, cracked, scaly skin, and raw, sensitive, swollen skin from scratching. In some embodiments, the term "treat atopic dermatitis" refers to an approach to stabilize (i.e. prevent the worsening) the state of one or more symptoms of atopic dermatitis, wherein the one or more symptoms include but are not limited to dry skin, itching, red to brownish-gray patches, small, raised bumps, thickened, cracked, scaly skin, and raw, sensitive, swollen skin from scratching. In some embodiments, the term "treat atopic dermatitis" refers to an approach to prevent spread of one or more symptoms of atopic dermatitis, wherein the one or more symptoms include but are not limited to dry skin, itching, red to brownish-gray patches, small, raised bumps, thickened, cracked, scaly skin, and raw, sensitive, swollen skin from scratching. In some embodiments, the term "treat atopic dermatitis" refers to an approach to delay or slow down progression of one or more symptoms of atopic dermatitis, wherein the one or more symptoms include but are not limited to dry skin, itching, red to brownish-gray patches, small, raised bumps, thickened, cracked, scaly skin, and raw, sensitive, swollen skin from scratching. In some embodiments, the term "treat atopic dermatitis" refers to an approach to partially or completely diminish the reoccurrence or remission of one or more symptoms of atopic dermatitis, wherein the one or more symptoms include but are not limited to dry skin, itching, red to brownish-gray patches, small, raised bumps, thickened, cracked, scaly skin, and raw, sensitive, swollen skin from scratching.

As used herein, the term "skin permeation rate" of a cyclic oligopeptide is measured using artificial skin (Start M, Merck), and refers to the percentage of the cyclic oligopeptide that penetrate the artificial skin after certain amount of time. For example, if 60% of the total amount of a cyclic oligopeptide of this disclosure has penetrated the artificial skin after 24 hours, then the skin permeation rate of the cyclic oligopeptide is 60% after 24 hours.

As used herein, the term "skin permeability coefficient (Kp)" refers to the rate at which the cyclic oligopeptide penetrates the skin, as measured using artificial skin (Start M, Merck). In some embodiments, permeability coefficient (Kp)(cm/hr) is calculated with the following equation:

$$\text{permeability coefficient } (Kp) = \frac{Q}{AT\Delta C};$$

wherein Q(mg) refers to the total amount of cyclic oligopeptide that pass through the artificial skin within a certain amount of time; A($cm^2$) refers to the internal cross-section area of the artificial skin in a diffusion cell; T(hr) refers to the total amount of time of cyclic oligopeptide permeation; and $\Delta$C(mg/mL) refers to the concentration difference of the cyclic oligopeptide between the two sides of the artificial skin. In some embodiments, the diffusion cell is a Franz Cell.

As used herein, the term "fast-acting" or "rapid-acting" refers to that an agent is able to penetrate skin at a relatively fast rate after application to the skin. In some embodiments, a fast-acting or a rapid-acting agent has a skin permeation rate of at least 10% after 1 hour. In some embodiments, a fast-acting or a rapid-acting agent has an average permeability coefficient of at least $1.0\times10^{-2}$ cm/hr after 1 hour. In some embodiments, a fast-acting or a rapid-acting agent has an average permeability coefficient of at least $2.0\times10^{-2}$ cm/hr after 1 hour.

As used herein, the term "long-lasting delivery" refers to that an agent is able to penetrate skin through a relatively long period time after application to the skin. In some embodiments, a long-lasting delivery agent has a skin permeation rate of at least 25% after 24 hours. In some embodiments, a long-lasting delivery agent has an average permeability coefficient of at least $1.0\times10^{-5}$ cm/hr after 24 hours. In some embodiments, a long-lasting delivery agent has an average permeability coefficient of at least $2.0\times10^{-5}$ cm/hr after 24 hours.

Cyclic Oligopeptides of the Disclosure

In a first aspect, the present disclosure provides a cyclic oligopeptide that binds to IL-13. Without being bound by theory, the cyclic oligopeptides disclosed herein are advantageous for use as active ingredients in disease treatment and other contexts, because they have both the high specificity of biological molecules and the bioavailability of small molecules. In addition, these cyclic oligopeptides can be locally applied, with superior skin permeability, concentrating on skin areas that affected by an IL-13 associated disorder or conditions. Linear oligopeptides have been proven to be effective when used to target extracellular receptors, but their applications are limited by their instability due to degradation by proteases. The cyclic oligopeptides disclosed herein, which are conformationally rigid, are advantageous compares to their linear counterparts due, in part, to their improved target affinity and specificity, as well as improved stability due to their resistance to proteolysis.

In some embodiments, the cyclic oligopeptide that binds to IL-13 comprises between two and twenty-two amino acid residues. In some embodiments, the cyclic oligopeptide that binds to IL-13 comprises between four and ten amino acid residues. In some embodiments, the cyclic oligopeptide that binds to IL-13 comprises between six and eight amino acid residues. In some embodiments, the cyclic oligopeptide that binds to IL-13 comprises six amino acid residues. In some embodiments, the cyclic oligopeptide that binds to IL-13 comprises seven amino acid residues. In some embodiments, the cyclic oligopeptide that binds to IL-13 comprises eight amino acid residues.

In some embodiments, the cyclic oligopeptide that binds to IL-13 comprises a L-proline residue or a D-proline residue. In some embodiments, the cyclic oligopeptide that binds to IL-13 comprises an amino acid sequence selected from the group consisting of SEQ ID NO:1-11. In some embodiments, the cyclic oligopeptide that binds to IL-13 comprises the amino acid sequence of SEQ ID NO:1. In some embodiments, the cyclic oligopeptide that binds to IL-13 comprises the amino acid sequence of SEQ ID NO:2. In some embodiments, the cyclic oligopeptide that binds to IL-13 comprises the amino acid sequence SEQ ID NO:3. In some embodiments, the cyclic oligopeptide that binds to IL-13 comprises the amino acid sequence of SEQ ID NO:4. In some embodiments, the cyclic oligopeptide that binds to IL-13 comprises the amino acid sequence of SEQ ID NO:5. In some embodiments, the cyclic oligopeptide that binds to IL-13 comprises the amino acid sequence of SEQ ID NO:6. In some embodiments, the cyclic oligopeptide that binds to IL-13 comprises the amino acid sequence of SEQ ID NO:7. In some embodiments, the cyclic oligopeptide that binds to IL-13 comprises the amino acid sequence of SEQ ID NO:8. In some embodiments, the cyclic oligopeptide that binds to IL-13 comprises the amino acid sequence of SEQ ID NO:9. In some embodiments, the cyclic oligopeptide that binds to IL-13 comprises the amino acid sequence of SEQ ID NO:10. In some embodiments, the cyclic oligopeptide that binds to IL-13 comprises the amino acid sequence of SEQ ID NO:11.

In some embodiments, the cyclic oligopeptide that binds to IL-13 has the structure of any one of Compounds 1-11, as defined herein (see, e.g., Table 1). In some embodiments, the cyclic oligopeptide that binds to IL-13 has the structure of Compound 1, as defined herein. In some embodiments, the cyclic oligopeptide that binds to IL-13 has the structure of Compound 2, as defined herein. In some embodiments, the cyclic oligopeptide that binds to IL-13 has the structure of Compound 3, as defined herein. In some embodiments, the cyclic oligopeptide that binds to IL-13 has the structure of Compound 4, as defined herein. In some embodiments, the cyclic oligopeptide that binds to IL-13 has the structure of Compound 5, as defined herein. In some embodiments, the cyclic oligopeptide that binds to IL-13 has the structure of Compound 6, as defined herein. In some embodiments, the cyclic oligopeptide that binds to IL-13 has the structure of Compound 7, as defined herein. In some embodiments, the cyclic oligopeptide that binds to IL-13 has the structure of Compound 8, as defined herein. In some embodiments, the cyclic oligopeptide that binds to IL-13 has the structure of Compound 9, as defined herein. In some embodiments, the cyclic oligopeptide that binds to IL-13 has the structure of Compound 10, as defined herein. In some embodiments, the cyclic oligopeptide that binds to IL-13 has the structure of Compound 11, as defined herein.

In some embodiments, the cyclic oligopeptide that binds to IL-13 has the structure of any one of Compounds 1-11, as defined herein (see, e.g., Table 1), or pharmaceutically acceptable salts thereof. In some embodiments, the cyclic oligopeptide that binds to IL-13 has the structure of Compound 1, as defined herein, or a pharmaceutically acceptable salt thereof. In some embodiments, the cyclic oligopeptide that binds to IL-13 has the structure of Compound 2, as defined herein, or a pharmaceutically acceptable salt thereof. In some embodiments, the cyclic oligopeptide that binds to IL-13 has the structure of Compound 3, as defined herein, or a pharmaceutically acceptable salt thereof. In some embodiments, the cyclic oligopeptide that binds to IL-13 has the structure of Compound 4, as defined herein, or a pharmaceutically acceptable salt thereof. In some embodiments, the cyclic oligopeptide that binds to IL-13 has the structure of Compound 5, as defined herein, or a pharmaceutically acceptable salt thereof. In some embodiments, the cyclic oligopeptide that binds to IL-13 has the structure of Compound 6, as defined herein, or a pharmaceutically acceptable salt thereof. In some embodiments, the cyclic oligopeptide that binds to IL-13 has the structure of Compound 7, as defined herein, or a pharmaceutically acceptable salt thereof. In some embodiments, the cyclic oligopeptide that binds to IL-13 has the structure of Compound 8, as defined herein, or a pharmaceutically acceptable salt thereof. In some embodiments, the cyclic oligopeptide that binds to IL-13 has the structure of Compound 9, as defined herein, or a pharmaceutically acceptable salt thereof. In some embodiments, the cyclic oligopeptide that binds to IL-13 has the structure of Compound 10, as defined herein, or a pharmaceutically acceptable salt thereof. In some embodiments, the cyclic oligopeptide that binds to IL-13 has the structure of Compound 11, as defined herein, or a pharmaceutically acceptable salt thereof.

In some embodiments, the cyclic oligopeptide that binds to IL-13 is lipidated. In some embodiments, the cyclic oligopeptide that binds to IL-13 is PEGylated.

In some embodiments, the cyclic oligopeptide that binds to IL-13 has a skin permeation rate of at least 25% after 24 hours. In some embodiments, the cyclic oligopeptide that binds to IL-13 has a skin permeation rate of at least 30% after 24 hours. In some embodiments, the cyclic oligopeptide that binds to IL-13 has a skin permeation rate of at least 35% after 24 hours. In some embodiments, the cyclic oligopeptide that binds to IL-13 has a skin permeation rate of at least 40% after 24 hours. In some embodiments, the cyclic oligopeptide that binds to IL-13 has a skin permeation rate of at least 45% after 24 hours. In some embodiments, the cyclic oligopeptide that binds to IL-13 has a skin permeation rate of at least 50% after 24 hours. In some embodiments, the cyclic oligopeptide that binds to IL-13 has a skin permeation rate of at least 55% after 24 hours. In some embodiments, the cyclic oligopeptide that binds to IL-13 has a skin permeation rate of at least 60% after 24 hours. In some embodiments, the cyclic oligopeptide that binds to IL-13 has a skin permeation rate of not more than 65% after 24 hours. In some embodiments, the cyclic oligopeptide that binds to IL-13 has a skin permeation rate of about 25% after 24 hours. In some embodiments, the cyclic oligopeptide that binds to IL-13 has a skin permeation rate of about 30% after 24 hours. In some embodiments, the cyclic oligopeptide that binds to IL-13 has a skin permeation rate of about 35% after 24 hours. In some embodiments, the cyclic oligopeptide that binds to IL-13 has a skin permeation rate of about 40% after 24 hours. In some embodiments, the cyclic oligopeptide that binds to IL-13 has a skin permeation rate of about 45% after 24 hours. In some embodiments, the cyclic oligopeptide that binds to IL-13 has a skin permeation rate of about 50% after 24 hours. In some embodiments, the cyclic oligopeptide that binds to IL-13 has a skin permeation rate of about 55% after 24 hours. In some embodiments, the cyclic oligopeptide that binds to IL-13 has a skin permeation rate of about 60% after 24 hours.

In some embodiments, the cyclic oligopeptide that binds to IL-13 has a skin permeation rate of between 25% and 60% after 24 hours. In some embodiments, the cyclic oligopeptide that binds to IL-13 has a skin permeation rate of between 25% and 55% after 24 hours. In some embodiments, the cyclic oligopeptide that binds to IL-13 has a skin permeation rate of between 25% and 50% after 24 hours. In some embodiments, the cyclic oligopeptide that binds to IL-13 has a skin permeation rate of between 25% and 45% after 24 hours. In some embodiments, the cyclic oligopeptide that binds to IL-13 has a skin permeation rate of between 25% and 40% after 24 hours. In some embodiments, the cyclic oligopeptide that binds to IL-13 has a skin permeation rate of between 25% and 35% after 24 hours. In some embodiments, the cyclic oligopeptide that binds to IL-13 has a skin permeation rate of between 25% and 30% after 24 hours. In some embodiments, the cyclic oligopeptide that binds to IL-13 has a skin permeation rate of between 30% and 60% after 24 hours. In some embodiments, the cyclic oligopeptide that binds to IL-13 has a skin permeation rate of between 35% and 60% after 24 hours. In some embodiments, the cyclic oligopeptide that binds to IL-13 has a skin permeation rate of between 40% and 60% after 24 hours. In some embodiments, the cyclic oligopeptide that binds to IL-13 has a skin permeation rate of between 45% and 60% after 24 hours. In some embodiments, the cyclic oligopeptide that binds to IL-13 has a skin permeation rate of between 50% and 60% after 24 hours. In some embodiments, the cyclic oligopeptide that binds to IL-13 has a skin permeation rate of between 55% and 60% after 24 hours. In some embodiments, the cyclic oligopeptide that binds to IL-13 has a skin permeation rate of between 30% and 50% after 24 hours. In some embodiments, the cyclic oligopeptide that binds to IL-13 has a skin permeation rate of between 35% and 45% after 24 hours. In some embodiments, the cyclic oligopeptide that binds to IL-13 has a skin permeation rate of between 30% and 40% after 24 hours. In some embodiments, the cyclic oligopeptide that binds to IL-13 has a skin permeation rate of between 35% and 40% after 24 hours. In some embodiments, the cyclic oligopeptide that binds to IL-13 has a skin permeation rate of between 40% and 45% after 24 hours.

In some embodiments, the cyclic oligopeptide that binds to IL-13 has a skin permeation rate of at least 10% after 1 hour. In some embodiments, the cyclic oligopeptide that binds to IL-13 has a skin permeation rate of at least 15% after 1 hour. In some embodiments, the cyclic oligopeptide that binds to IL-13 has a skin permeation rate of at least 20% after 1 hour. In some embodiments, the cyclic oligopeptide that binds to IL-13 has a skin permeation rate of at least 25% after 1 hour. In some embodiments, the cyclic oligopeptide that binds to IL-13 has a skin permeation rate of not more than 30% after 1 hour. In some embodiments, the cyclic oligopeptide that binds to IL-13 has a skin permeation rate of about 10% after 1 hour. In some embodiments, the cyclic oligopeptide that binds to IL-13 has a skin permeation rate of about 15% after 1 hour. In some embodiments, the cyclic oligopeptide that binds to IL-13 has a skin permeation rate of about 20% after 1 hour. In some embodiments, the cyclic oligopeptide that binds to IL-13 has a skin permeation rate of about 25% after 1 hour.

In some embodiments, the cyclic oligopeptide that binds to IL-13 has a skin permeation rate of between 10% and 25% after 1 hour. In some embodiments, the cyclic oligopeptide that binds to IL-13 has a skin permeation rate of between 10% and 20% after 1 hour. In some embodiments, the cyclic oligopeptide that binds to IL-13 has a skin permeation rate of between 10% and 15% after 1 hour. In some embodiments, the cyclic oligopeptide that binds to IL-13 has a skin permeation rate of between 15% and 25% after 1 hour. In some embodiments, the cyclic oligopeptide that binds to IL-13 has a skin permeation rate of between 20% and 25% after 1 hour. In some embodiments, the cyclic oligopeptide that binds to IL-13 has a skin permeation rate of between 15% and 20% after 1 hour.

In some embodiments, the cyclic oligopeptide that binds to IL-13 has an average skin permeability coefficient of at least $1.0\times10^{-5}$ cm/hr after 24 hours. In some embodiments, the cyclic oligopeptide that binds to IL-13 has an average skin permeability coefficient of at least $2.0\times10^{-5}$ cm/hr after 24 hours. In some embodiments, the cyclic oligopeptide that binds to IL-13 has an average skin permeability coefficient of at least $5.0\times10^{-5}$ cm/hr after 24 hours. In some embodiments, the cyclic oligopeptide that binds to IL-13 has an average skin permeability coefficient of at least $1.0\times10^{-4}$ cm/hr after 24 hours. In some embodiments, the cyclic oligopeptide that binds to IL-13 has an average skin permeability coefficient of at least $2.0\times10^{-4}$ cm/hr after 24 hours. In some embodiments, the cyclic oligopeptide that binds to IL-13 has an average skin permeability coefficient of at least $3.0\times10^{-4}$ cm/hr after 24 hours. In some embodiments, the cyclic oligopeptide that binds to IL-13 has an average skin permeability coefficient of at least $4.0\times10^{-4}$ cm/hr after 24 hours. In some embodiments, the cyclic oligopeptide that binds to IL-13 has an average skin permeability coefficient of not more than $5.0\times10^{-4}$ cm/hr after 24 hours. In some embodiments, the cyclic oligopeptide that binds to IL-13 has an average skin permeability coefficient of about $1.0\times10^{-5}$ cm/hr after 24 hours. In some embodiments, the cyclic oligopeptide that binds to IL-13 has an average skin permeability coefficient of about $2.0\times10^{-5}$ cm/hr after 24 hours. In some embodiments, the cyclic oligopeptide that binds to IL-13 has an average skin permeability coefficient of about $5.0\times10^{-5}$ cm/hr after 24 hours. In some embodiments, the cyclic oligopeptide that binds to IL-13 has an average skin permeability coefficient of about $1.0\times10^{-4}$ cm/hr after 24 hours. In some embodiments, the cyclic oligopeptide that binds to IL-13 has an average skin permeability coefficient of about $2.0\times10^{-4}$ cm/hr after 24 hours. In some embodiments, the cyclic oligopeptide that binds to IL-13 has an average skin permeability coefficient of about $3.0\times10^{-4}$ cm/hr after 24 hours. In some embodiments, the cyclic oligopeptide that binds to IL-13 has an average skin permeability coefficient of about $4.0\times10^{-4}$ cm/hr after 24 hours. In some embodiments, the cyclic oligopeptide that binds to IL-13 has an average skin permeability coefficient of about $4.5\times10^{-4}$ cm/hr after 24 hours.

In some embodiments, the cyclic oligopeptide that binds to IL-13 has an average skin permeability coefficient of between $1.0\times10^{-5}$ cm/hr and $5.0\times10^{-4}$ cm/hr after 24 hours. In some embodiments, the cyclic oligopeptide that binds to IL-13 has an average skin permeability coefficient of between $5.0\times10^{-5}$ cm/hr and $5.0\times10^{-4}$ cm/hr after 24 hours. In some embodiments, the cyclic oligopeptide that binds to IL-13 has an average skin permeability coefficient of between $1.0\times10^{-4}$ cm/hr and $5.0\times10^{-4}$ cm/hr after 24 hours. In some embodiments, the cyclic oligopeptide that binds to IL-13 has an average skin permeability coefficient of between $1.0\times10^{-5}$ cm/hr and $1.0\times10^{-4}$ cm/hr after 24 hours. In some embodiments, the cyclic oligopeptide that binds to IL-13 has an average skin permeability coefficient of between $1.0\times10^{-5}$ cm/hr and $5.0\times10^{-5}$ cm/hr after 24 hours. In some embodiments, the cyclic oligopeptide that binds to IL-13 has an average skin permeability coefficient of between $5.0\times10^{-5}$ cm/hr and $1.0\times10^{-4}$ cm/hr after 24 hours.

In some embodiments, the cyclic oligopeptide that binds to IL-13 has an average skin permeability coefficient of at least $1.0\times10^{-2}$ cm/hr after 1 hour. In some embodiments, the cyclic oligopeptide that binds to IL-13 has an average skin permeability coefficient of at least $2.0 \times 10^{-2}$ cm/hr after 1 hour. In some embodiments, the cyclic oligopeptide that binds to IL-13 has an average skin permeability coefficient of at least $3.0 \times 10^{-2}$ cm/hr after 1 hour. In some embodiments, the cyclic oligopeptide that binds to IL-13 has an average skin permeability coefficient of at least $4.0 \times 10^{-2}$ cm/hr after 1 hour. In some embodiments, the cyclic oligopeptide that binds to IL-13 has an average skin permeability coefficient of at least $5.0 \times 10^{-2}$ cm/hr after 1 hour. In some embodiments, the cyclic oligopeptide that binds to IL-13 has an average skin permeability coefficient of not more than $6.0 \times 10^{-2}$ cm/hr after 1 hour. In some embodiments, the cyclic oligopeptide that binds to IL-13 has an average skin permeability coefficient of about $1.0 \times 10^{-2}$ cm/hr after 1 hour. In some embodiments, the cyclic oligopeptide that binds to IL-13 has an average skin permeability coefficient of about $2.0 \times 10^{-2}$ cm/hr after 1 hour. In some embodiments, the cyclic oligopeptide that binds to IL-13 has an average skin permeability coefficient of about $3.0 \times 10^{-2}$ cm/hr after 1 hour. In some embodiments, the cyclic oligopeptide that binds to IL-13 has an average skin permeability coefficient of about $4.0 \times 10^{-2}$ cm/hr after 1 hour. In some embodiments, the cyclic oligopeptide that binds to IL-13 has an average skin permeability coefficient of about $5.0 \times 10^{-2}$ cm/hr after 1 hour. In some embodiments, the cyclic oligopeptide that binds to IL-13 has an average skin permeability coefficient of about $5.5 \times 10^{-2}$ cm/hr after 1 hour.

In some embodiments, the cyclic oligopeptide that binds to IL-13 has an average skin permeability coefficient of between $1.0 \times 10^{-2}$ cm/hr and $5.0 \times 10^{-2}$ cm/hr after 1 hour. In some embodiments, the cyclic oligopeptide that binds to IL-13 has an average skin permeability coefficient of between $2.0 \times 10^{-2}$ cm/hr and $5.0 \times 10^{-2}$ cm/hr after 1 hour. In some embodiments, the cyclic oligopeptide that binds to IL-13 has an average skin permeability coefficient of between $3.0 \times 10^{-2}$ cm/hr and $5.0 \times 10^{-2}$ cm/hr after 1 hour. In some embodiments, the cyclic oligopeptide that binds to IL-13 has an average skin permeability coefficient of between $4.0 \times 10^{-2}$ cm/hr and $5.0 \times 10^{-2}$ cm/hr after 1 hour. In some embodiments, the cyclic oligopeptide that binds to IL-13 has an average skin permeability coefficient of between $1.0 \times 10^{-2}$ cm/hr and $4.0 \times 10^{-2}$ cm/hr after 1 hour. In some embodiments, the cyclic oligopeptide that binds to IL-13 has an average skin permeability coefficient of between $1.0 \times 10^{-2}$ cm/hr and $3.0 \times 10^{-2}$ cm/hr after 1 hour. In some embodiments, the cyclic oligopeptide that binds to IL-13 has an average skin permeability coefficient of between $1.0 \times 10^{-2}$ cm/hr and $2.0 \times 10^{-2}$ cm/hr after 1 hour. In some embodiments, the cyclic oligopeptide that binds to IL-13 has an average skin permeability coefficient of between $2.0 \times 10^{-2}$ cm/hr and $4.0 \times 10^{-2}$ cm/hr after 1 hour. In some embodiments, the cyclic oligopeptide that binds to IL-13 has an average skin permeability coefficient of between $3.0 \times 10^{-2}$ cm/hr and $4.0 \times 10^{-2}$ cm/hr after 1 hour. In some embodiments, the cyclic oligopeptide that binds to IL-13 has an average skin permeability coefficient of between $2.0 \times 10^{-2}$ cm/hr and $3.0 \times 10^{-2}$ cm/hr after 1 hour.

Pharmaceutical Compositions and Administration

In a second aspect, the present disclosure provides a pharmaceutical formulation comprising a cyclic oligopeptide disclosed herein and a pharmaceutically acceptable carrier. In some embodiments, the pharmaceutical composition comprises a therapeutically effective amount of the cyclic oligopeptide described herein.

The pharmaceutical compositions may be in a variety of forms, for example, liquid, semi-solid and solid dosage forms, such as liquid solutions (e.g., injectable and infusible solutions), dispersions or suspensions, powders, capsules, pills, tablets and liposomes. The preferred form depends on the intended mode of administration and therapeutic application. In some embodiments, the pharmaceutical compositions are in the form of injectable or infusible solutions. Optionally, mode of administration is topical. The pharmaceutical composition may be administered by intravenous infusion or injection. In some embodiments, the pharmaceutical composition is formulated for subcutaneous injection. Optionally, the pharmaceutical composition is formulated for transdermal administration. In some embodiments, the cyclic oligopeptide is formulated in a tape or a patch. Formulations for injection may be presented in unit dosage form, e.g., in ampoules, pre-filled syringes, or in multi-dose containers, with or without an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be prepared in powder form for reconstitution with a suitable vehicle, e.g., sterile pyrogen-free water, before use.

Therapeutic compositions typically must be sterile and stable under the conditions of manufacture and storage. The composition may be formulated as a solution, microemulsion, dispersion, liposome, or other ordered structure suitable to high drug concentration. Sterile injectable solutions may be prepared by incorporating the cyclic oligopeptide in the required amount in an appropriate solvent with one or a combination of ingredients enumerated above, as required, followed by filtered sterilization. Dispersions may be prepared by incorporating the cyclic oligopeptide into a sterile vehicle that contains a basic dispersion medium and the required other ingredients from those enumerated above. In the case of sterile powders for the preparation of sterile injectable or topical solutions, the preferred methods of preparation include vacuum drying and freeze drying that yield a powder of the cyclic oligopeptide and any additional desired ingredient from a previously sterile filtered solution thereof. The proper fluidity of a solution can be maintained, for example, by the use of a coating such as lecithin, by the maintenance of the required particle size in the case of dispersion and/or by the use of surfactants. Prolonged absorption of injectable compositions can be brought about by including in the composition an agent that delays absorption, for example, monostearate salts and gelatin.

The pharmaceutical compositions may be administered by a variety of methods known in the art. In some embodiments, the route/mode of administration is topical, transdermal, subcutaneous injection, intravenous infusion or oral. In some embodiments, the route/mode of administration is topical, transdermal, or subcutaneous injection. In some embodiments, the route/mode of administration is topical. In some embodiments, the route/mode of administration is transdermal. In some embodiments, the route/mode of administration is subcutaneous injection. In some embodiments, the route/mode of administration is intravenous infusion. In some embodiments, the route/mode of administration is oral. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It may be advantageous to formulate pharmaceutical compositions in dosage unit form for ease of administration and uniformity of dosage. The specification for the dosage unit forms may be dictated by and directly dependent on (a) the unique characteristics of the cyclic oligopeptide and the particular therapeutic or prophylactic effect to be achieved, and (b) the limitations inherent in the art of compounding such a cyclic oligopeptide for the treatment of sensitivity in individuals. Dosage values may vary with the type and severity of the condition to be alleviated. For any particular subject, specific dosage regimens may be adjusted over time according to the individual need and the professional judgment of the person administering or supervising the administration of the compositions, and that dosage ranges set forth herein are exemplary only and are not intended to limit the scope or practice of the paragraphed composition.

Methods of Treating IL-13-Associated Skin Diseases and Conditions

In a third aspect, the present disclosure provides a method of treating or preventing an IL-13-associated skin disorder or condition in a subject in need thereof. In some embodiments, the method comprises administering to the subject a therapeutically effective amount of any one of the cyclic oligopeptides disclosed herein or a combination thereof. In some embodiments, the subject is a human. The cyclic oligopeptide may be administered as a pharmaceutical composition disclosed herein. The cyclic oligopeptide may be administered according to any of the routes of administration disclosed herein.

In some embodiments, the cyclic oligopeptide used for treatment comprises an amino acid sequence selected from the group consisting of SEQ ID NO:1-11. In some embodiments, the cyclic oligopeptide used for treatment comprises the amino acid sequence of D-ARG D-PHE D-VAL TYR GLU PRO (SEQ ID NO:1). Optionally, the cyclic oligopeptide used for treatment comprises the amino acid sequence of ARG THR D-VAL GLU D-PHE D-PRO (SEQ ID NO:2). The cyclic oligopeptide used for treatment may comprise the amino acid sequence of GLU D-THR D-VAL TRP D-PRO D-PRO (SEQ ID NO:3). In some embodiments, the cyclic oligopeptide used for treatment comprises the amino acid sequence of ARG GLU D-VAL TRP D-PRO D-PRO (SEQ ID NO:4). Optionally, the cyclic oligopeptide used for treatment comprises the amino acid sequence of TRP VAL ARG GLU D-PRO D-PRO (SEQ ID NO:5). The cyclic oligopeptide used for treatment may comprise the amino acid sequence of TYR ARG GLU D-THR D-VAL D-PRO (SEQ ID NO:6). In some embodiments, the cyclic oligopeptide used for treatment comprises the amino acid sequence of THR ARG D-PHE PRO D-LEU D-PRO (SEQ ID NO:7). Optionally, the cyclic oligopeptide used for treatment comprises the amino acid sequence of D-LEU ARG GLU PRO TRP MET PRO (SEQ ID NO:8). The cyclic oligopeptide used for treatment may comprise the amino acid sequence of D-ARG LEU D-TRP TRP D-THR GLU PRO (SEQ ID NO:9). In some embodiments, the cyclic oligopeptide used for treatment comprises the amino acid sequence of ARG ASP TYR CYS D-PRO D-TRP D-PRO (SEQ ID NO:10). Optionally, the cyclic oligopeptide used for treatment comprises the amino acid sequence of VAL PRO D-LEU D-TRP D-VAL LEU ARG PRO (SEQ ID NO:11).

In some embodiments, the cyclic oligopeptide used for treatment has the structure of any one of Compounds 1-11, as defined herein (see, e.g., Table 1). In some embodiments, the cyclic oligopeptide used for treatment has the structure of Compound 1, as defined herein. Optionally, the cyclic oligopeptide used for treatment has the structure of Compound 2, as defined herein. The cyclic oligopeptide used for treatment may have the structure of Compound 3, as defined herein. In some embodiments, the cyclic oligopeptide used for treatment has the structure of Compound 4, as defined herein. Optionally, the cyclic oligopeptide used for treatment has the structure of Compound 5, as defined herein. The cyclic oligopeptide used for treatment may have the structure of Compound 6, as defined herein. In some embodiments, the cyclic oligopeptide used for treatment has the structure of Compound 7, as defined herein. Optionally, the cyclic oligopeptide used for treatment has the structure of Compound 8, as defined herein. The cyclic oligopeptide used for treatment may have the structure of Compound 9, as defined herein. In some embodiments, the cyclic oligopeptide used for treatment has the structure of Compound 10, as defined herein. Optionally, the cyclic oligopeptide used for treatment has the structure of Compound 11, as defined herein.

In some embodiments, the cyclic oligopeptide used for treatment has the structure of any one of Compounds 1-11, as defined herein (see, e.g., Table 1), or pharmaceutically acceptable salts thereof. In some embodiments, the cyclic oligopeptide used for treatment has the structure of Compound 1, as defined herein, or a pharmaceutically acceptable salt thereof. Optionally, the cyclic oligopeptide used for treatment has the structure of Compound 2, as defined herein, or a pharmaceutically acceptable salt thereof. The cyclic oligopeptide used for treatment may have the structure of Compound 3, as defined herein, or a pharmaceutically acceptable salt thereof. In some embodiments, the cyclic oligopeptide used for treatment has the structure of Compound 4, as defined herein, or a pharmaceutically acceptable salt thereof. Optionally, the cyclic oligopeptide used for treatment has the structure of Compound 5, as defined herein, or a pharmaceutically acceptable salt thereof. The cyclic oligopeptide used for treatment may have the structure of Compound 6, as defined herein, or a pharmaceutically acceptable salt thereof. In some embodiments, the cyclic oligopeptide used for treatment has the structure of Compound 7, as defined herein, or a pharmaceutically acceptable salt thereof. Optionally, the cyclic oligopeptide used for treatment has the structure of Compound 8, as defined herein, or a pharmaceutically acceptable salt thereof. The cyclic oligopeptide used for treatment may have the structure of Compound 9, as defined herein, or a pharmaceutically acceptable salt thereof. In some embodiments, the cyclic oligopeptide used for treatment has the structure of Compound 10, as defined herein, or a pharmaceutically acceptable salt thereof. Optionally, the cyclic oligopeptide used for treatment has the structure of Compound 11, as defined herein, or a pharmaceutically acceptable salt thereof.

In some embodiments, the IL-13-associated skin disorder or condition is an inflammatory, an allergic, or an autoimmune disorder or condition. In some embodiments, the IL-13-associated skin disorder or condition is an inflammatory disorder or condition. In some embodiments, the IL-13-associated skin disorder or condition is an allergic disorder or condition. In some embodiments, the IL-13-associated skin disorder or condition is an autoimmune disorder or condition. In some embodiments, the IL-13-associated skin disorder or condition is selected from the group consisting of: atopic dermatitis, allergic contact dermatitis, urticaria, eczema, chronic hand eczema, bullous diseases (bullous pemphigoid), alopecia areata, and prurigo and molluscum contagiosum. In some embodiments, the IL-13-associated skin disorder or condition is atopic dermatitis. In some embodiments, the IL-13-associated skin disorder or condition is allergic contact dermatitis. In some embodiments, the IL-13-associated skin disorder or condition is urticaria. In some embodiments, the IL-13-associated skin disorder or condition is eczema. In some embodiments, the IL-13-associated skin disorder or condition is chronic hand eczema. In some embodiments, the IL-13-associated skin disorder or condition is bullous diseases (bullous pemphigoid). In some embodiments, the IL-13-associated skin disorder or condition is alopecia areata. In some embodiments, the IL-13-associated skin disorder or condition is prurigo. In some embodiments, the IL-13-associated skin disorder or condition is molluscum contagiosum.

In some embodiments, the one or more cyclic oligopeptides bind to IL-13 and reduces biological activities of IL-13 and/or an IL-13 receptor (IL-13R). In some embodiments, the one or more cyclic oligopeptides bind to IL-13 and reduces biological activities of IL-13. In some embodiments, the one or more cyclic oligopeptides bind to IL-13 and reduces biological activities of an IL-13 receptor (IL-13R). In some embodiments, the one or more cyclic oligopeptides bind to IL-13 and reduces biological activities of IL-13 or an IL-13 receptor (IL-13R). In some embodiments, the one or more cyclic oligopeptides bind to IL-13 and reduces biological activities of IL-13 and an IL-13 receptor (IL-13R).

In some embodiments, the present disclosure provides a method of treating or preventing an IL-13-associated skin disorder or condition in a subject in need thereof, comprising administering to the subject a therapeutically effective amount of any one of the cyclic oligopeptides of this disclosure or a combination thereof. In some embodiments, the cyclic oligopeptide or the combination thereof is administered topically. In some embodiments, the cyclic oligopeptide or the combination thereof is administered transdermally. In some embodiments, the cyclic oligopeptide or the combination thereof is administered subcutaneously.

In some embodiments, the cyclic oligopeptide or the combination thereof is administered intravenously. In some embodiments, the cyclic oligopeptide or the combination thereof is administered orally. Methods for oral administration of biologically active proteins and peptides are known in the art. A number of strategies for preventing degradation of orally administered peptides have been suggested. Examples of methods for oral administration of the cyclic oligopeptide include, but are not limited to, the use of core-shell particles (U.S. Pat. No. 7,090,868) and nanotubes (U.S. Pat. No. 7,195,780); liposomes and aqueous emulsions and suspensions (U.S. Pat. No. 7,316,818; WO 06/062544; U.S. Pat. Nos. 6,071,535 and 5,874,105); gas-filled liposomes (U.S. Pat. Nos. 6,551,576; 6,808,720; and 7,083,572); nanodroplets dispersed in an aqueous medium (US 2007/0184076); matrix-carriers containing peptide-effectors that provide penetration across biological barriers for administration of hydrophobic proteins (WO 06/097793, WO 05/094785, and WO 03/066859); use of non-covalent protein-polysaccharide complexes (EP0491114B1); use of pharmaceutical compositions described in U.S. Pat. No. 8,936,786; use of Peptelligence® system (U.S. Pat. No. 8,377,863; WO 2014/138241; and WO 2016/115082); all of these publications and patents are specifically incorporated herein by reference.

Methods of Producing Cyclic Oligopeptides

In a fourth aspect, the present disclosure provides a method of producing a cyclic oligopeptide that binds to IL-13. In some embodiments, the methods comprises the steps of: (1) contacting FMOC (9-fluorenylmethyloxycarbonyl)-D-Pro-2cl-resin or FMOC-Pro-2cl-resin with a first amino acid residue under conditions suitable to form a peptide bond between the first amino acid residue and the resin-bound D-Pro or Pro to form a resin-bound oligopeptide; (2) washing the resin-bound oligopeptide to remove any unbound amino acid residue; (3) contacting the resin-bound oligopeptide with an additional amino acid residue under conditions suitable to form a peptide bond between the additional amino acid residue and the resin-bound oligopeptide; (4) washing the resin-bound oligopeptide to remove any unbound amino acid residue; (5) removing the resin from the oligopeptide; and (6) cyclizing the oligopeptide.

In some embodiments, the conditions suitable to form a peptide bond in steps (1) and (3) include the addition of O-(Benzotriazol-1-yl)-N, N, N', N'-tetramethyluronium tetrafluoroborate (TBTU). In some embodiments, the conditions suitable to form a peptide bond in steps (1) and (3) further include the addition of N,N-Dimethylformamide (DMF) and N,N-Diisopropylethylamine (DIEA). In some embodiments, steps (3) and (4) are repeated between 1 and 20 times before the resin is removed from the oligopeptide.

In some embodiments, the cyclizing step comprises the carboxyl group of the D-Pro or Pro residue forming a covalent bond with one or more amino groups of the linear oligopeptide. In some embodiments, the cyclizing step comprises the addition of DMF, PyBOP (Benzotriazol-1-yl-oxytripyrrolidinophosphonium hexafluorophosphate), HOBT (1-Hydroxybenzotriazole), and DIEA to the linear oligopeptide and incubation of the mixture thereof at room temperature.

In some embodiments, the cyclic oligopeptide that binds to IL-13 is a cyclic oligopeptide disclosed herein. In some embodiments, the method disclosed herein is used to produce the cyclic oligopeptides of the present disclosure.

EXAMPLES

Exemplary methods and materials are described herein, although methods and materials similar or equivalent to those described herein can also be used in the practice or testing of the various aspects and embodiments of the disclosure. The materials, methods, and examples are illustrative only and not intended to be limiting.

Example 1. Production of Cyclic Oligopeptides that Bind to IL-13

Cyclic oligopeptides of the disclosure were produced using the following steps:
1) FMOC (9-fluorenylmethyloxycarbonyl)-D-Pro-2cl-resin or FMOC-Pro-2cl-resin (selected according to the sequence and structure of oligopeptides to be produced) was weighed and placed into a glass reaction column, and Dichloromethane(methylene chloride or DCM) was added and incubated for 30 minutes to allow the resin to swell.

2) DCM was removed by vacuum.
3) The resin 3 was washed times with N,N-Dimethylformamide (DMF).
4) 20% piperidine/DMF solution was added and incubated for 20 minutes to remove the FMOC protective group.
5) The liquid solution was removed by vacuum, and the resin was washed 6 times with DMF.
6) The second amino acid, which would be added to the N-terminus of D-Pro or Pro, and TBTU (0-(Benzotriazol-1-yl)-N, N, N', N'-tetramethyluronium tetrafluoroborate) were weighed and added to the resin.
7) DIEA (N,N-Diisopropylethylamine) was dissolved in DMF and added to the resin and react for 30 minutes. The progress of the reaction was followed using a color detection reaction. The reaction was determined to be complete when the solution was bright yellow, and the resin was yellow.
8) The solvent was removed by vacuum.
9) Steps 6) to 8) were repeated to add each additional amino acid residue to the N-terminus of the growing oligopeptide until the last amino acid residue was added to the oligopeptide. The last amino acid residue is the residue that was subsequently cyclized with the C-terminus of the initial D-Pro or Pro residue, as shown in the structures Table 1, below.
10) The resin was washed three times with DMF, DCM, and methanol and dried by vacuum.
11) Full protection lysis solution was added, and the resin was removed by filtering the solution with sand core.
12) 0.5 ml DIEA (N,N-Diisopropylethylamine) was added to the passthrough.
13) The DCM was removed from the passthrough by spin-drying with a vacuum rotary evaporator until the solution became viscous. Analytically pure DMF, PyBOP (Benzotriazol-1-yl-oxytripyrrolidinophosphonium hexafluorophosphate), HOBT (1-Hydroxybenzotriazole), and DIEA were added and incubated for 4 hours at room temperature.
14) After the reaction is complete, an acidic solution was added to separate out the solid, which was dried under vacuum.
15) A lysis solution was added to remove the protective groups from the amino acid side chains.
16) Ether was added to the solution to separate out solid products, which were centrifuged and washed three times and then dried under vacuum.

Figure 2A:
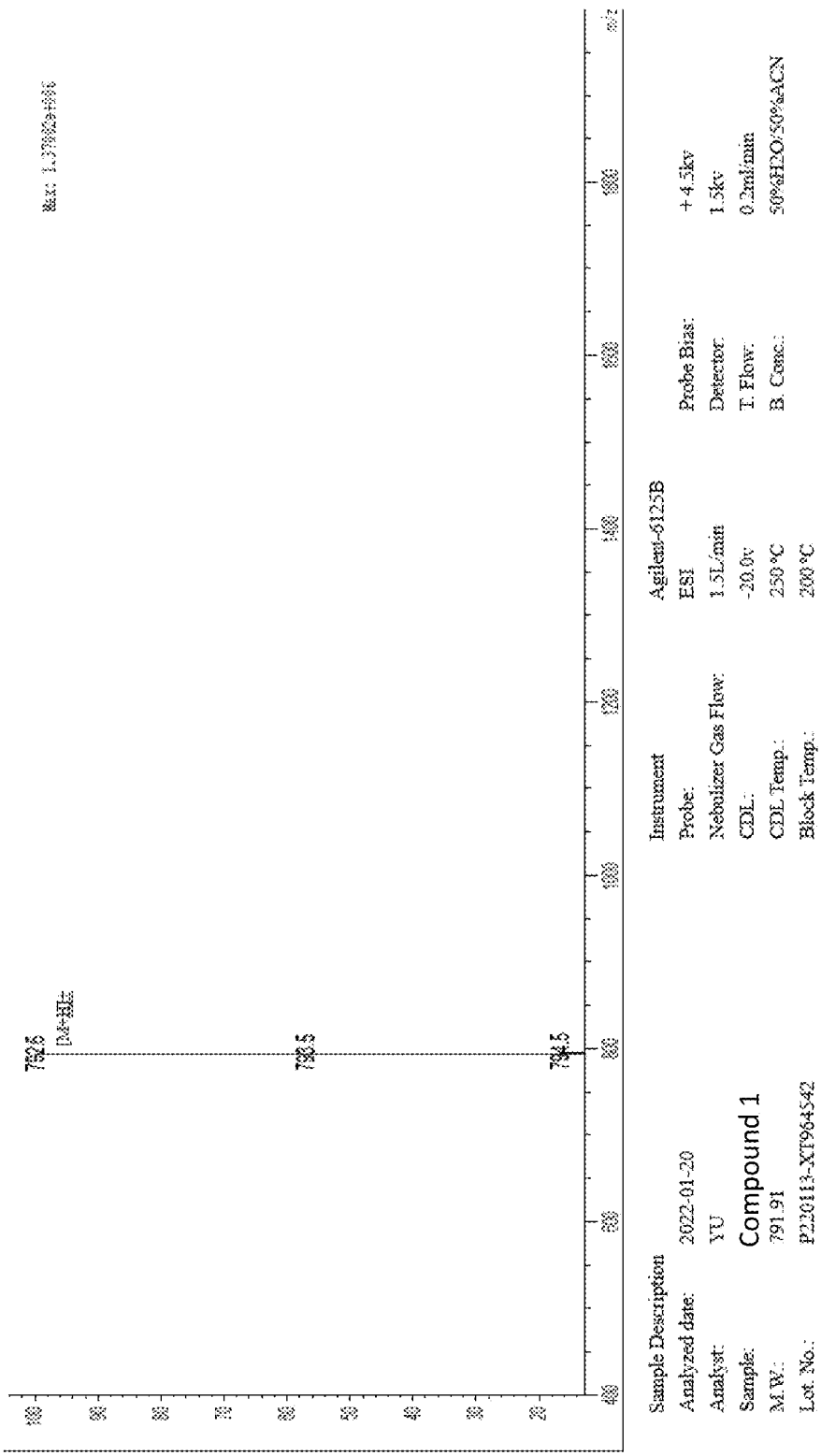
FIG. 2A provides the mass spectrometry (MS) spectrum for Compound 1.
Figure 2B:
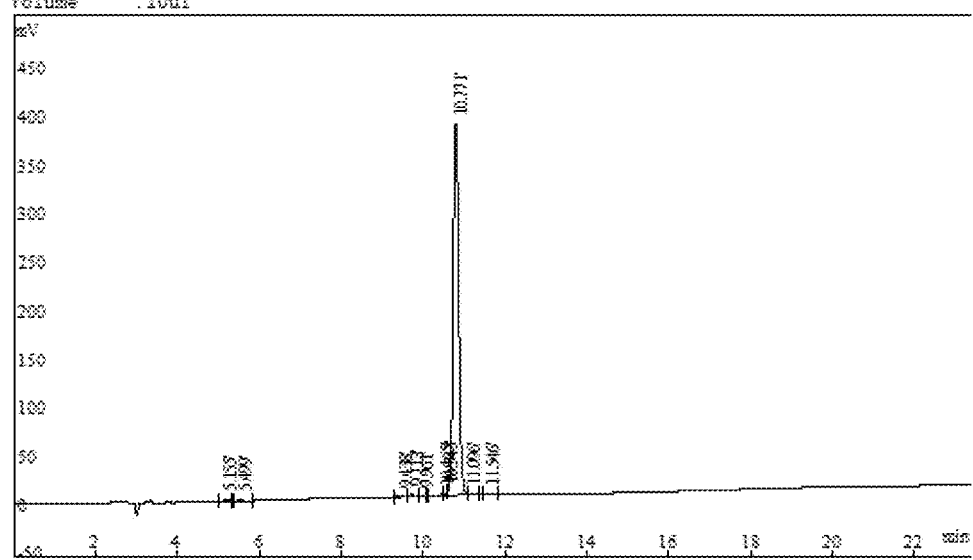
FIG. 2B provides the high-performance liquid chromatography (HPLC) chromatogram for Compound 1.
Figure 3A:
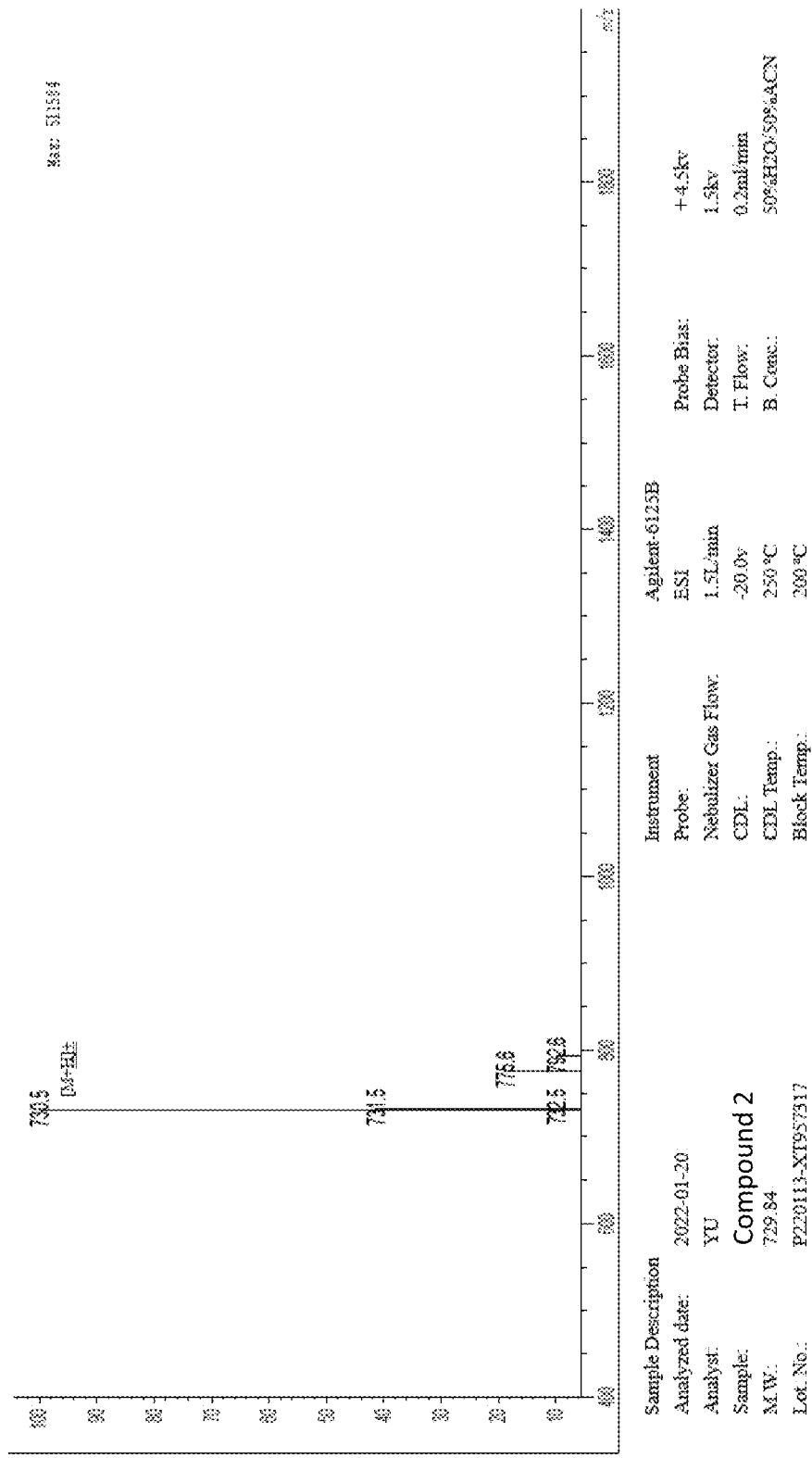
FIG. 3A provides the MS spectrum for Compound 2.
Figure 3B:
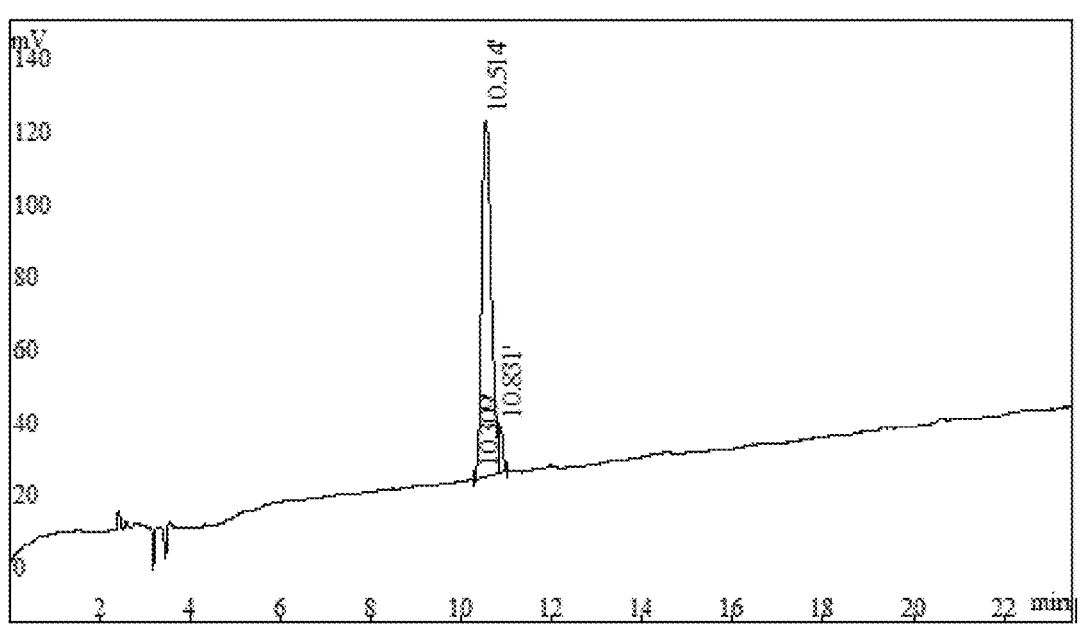
FIG. 3B provides the HPLC chromatogram for Compound 2.
Figure 4A:
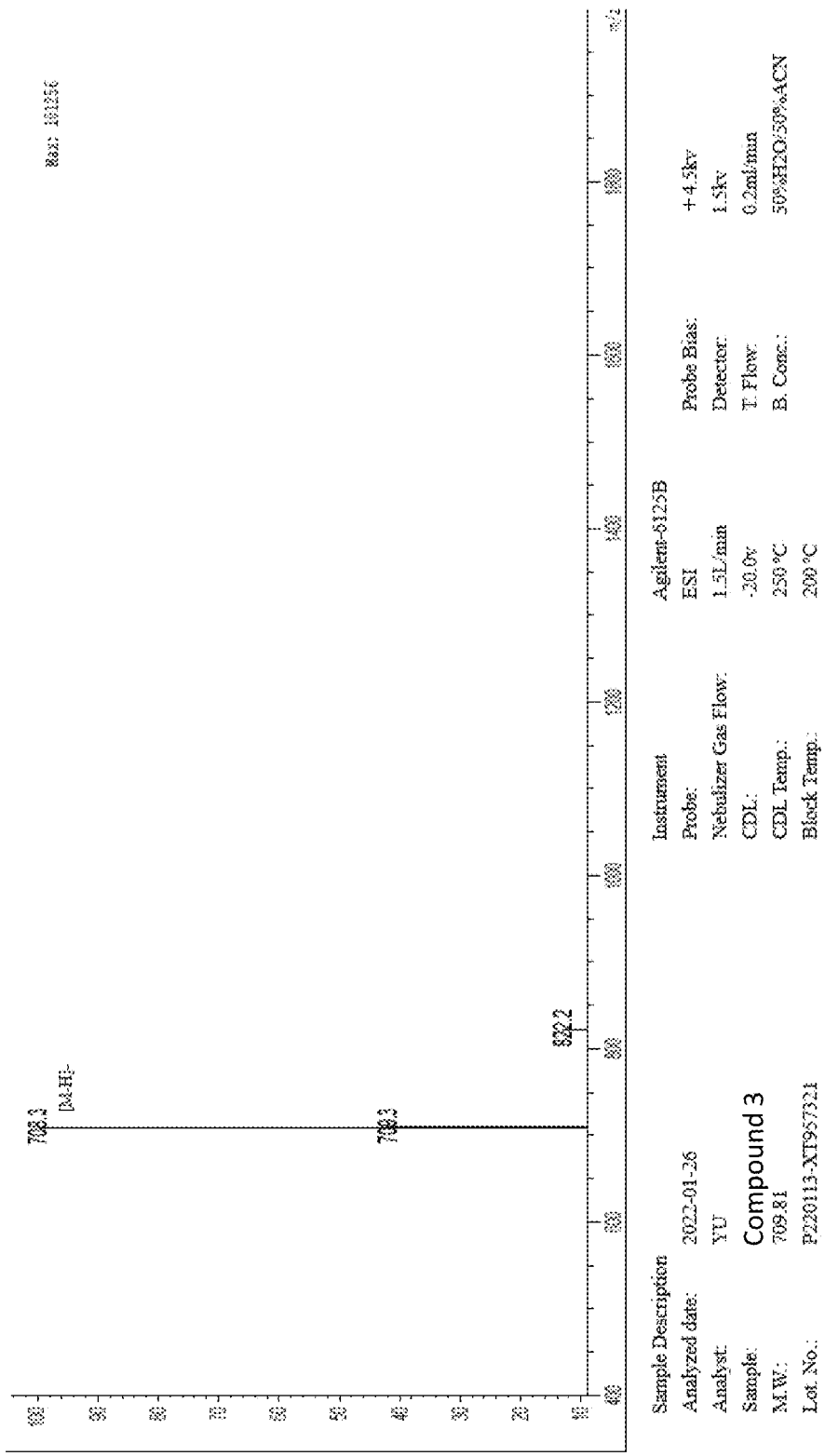
FIG. 4A provides the MS spectrum for Compound 3.
Figure 4B:
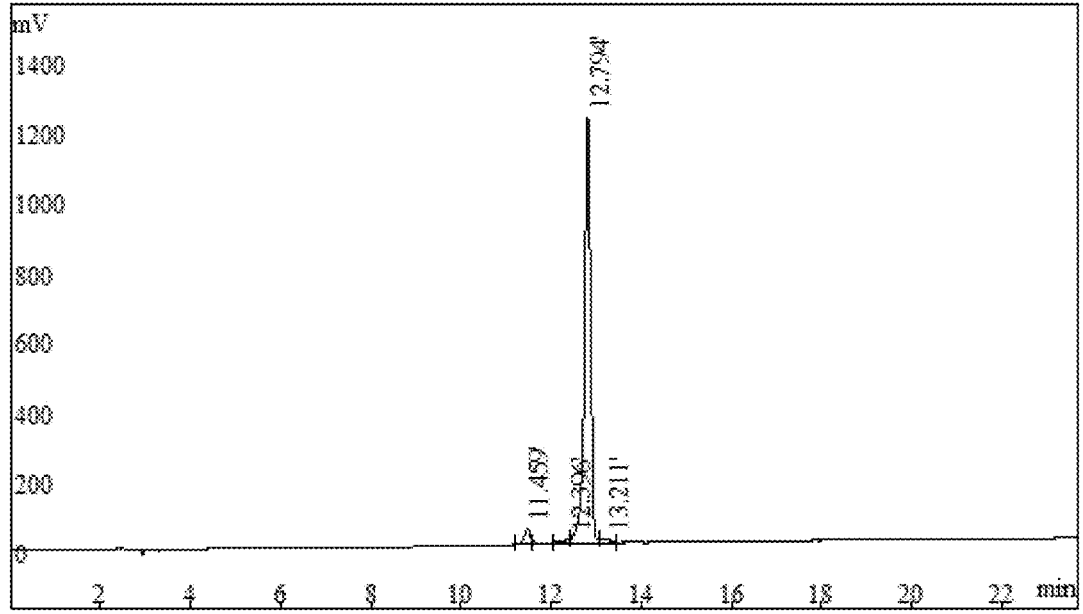
FIG. 4B provides the HPLC chromatogram for Compound 3.
Figure 5A:
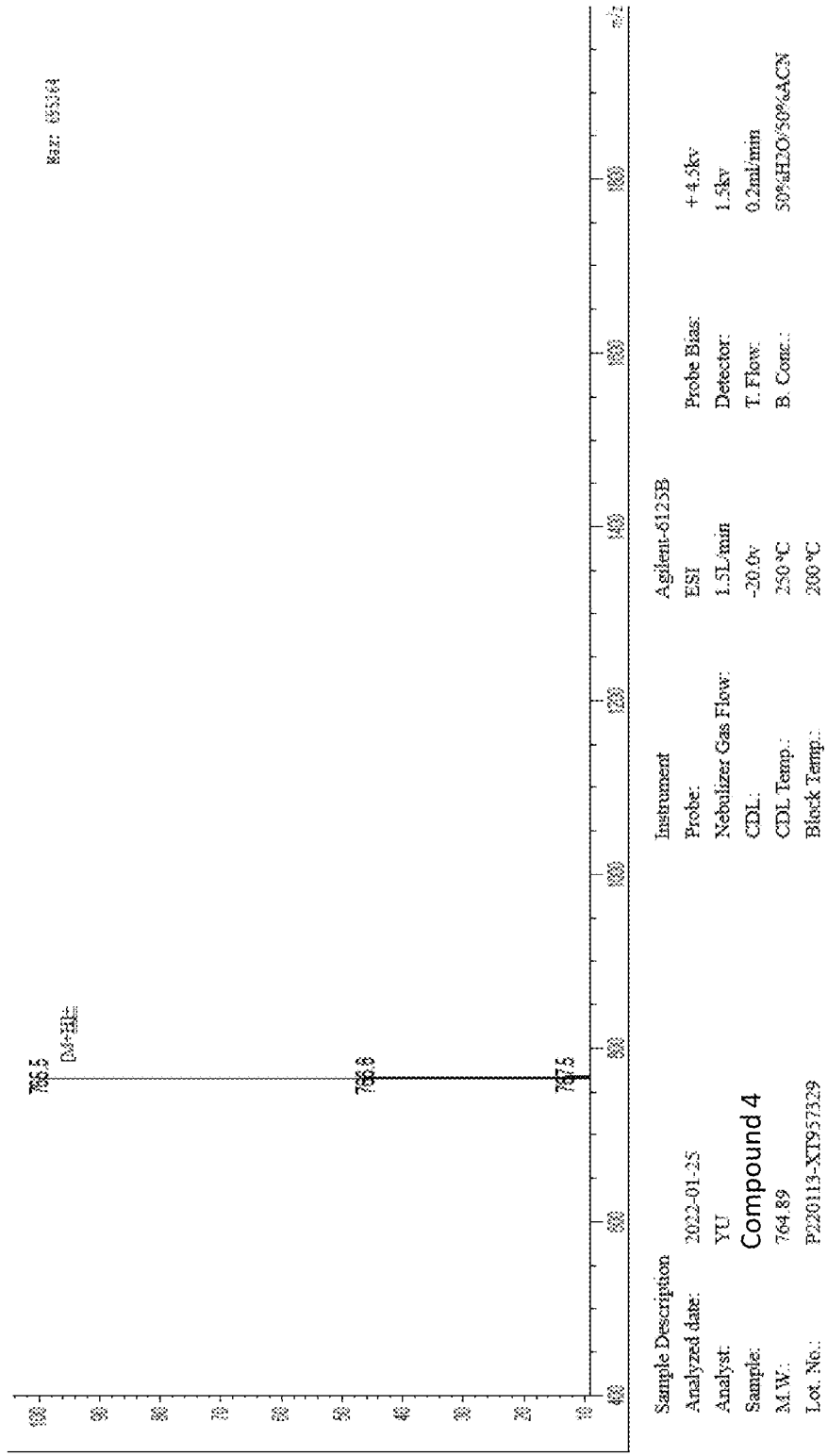
FIG. 5A provides the MS spectrum for Compound 4.
Figure 5B:
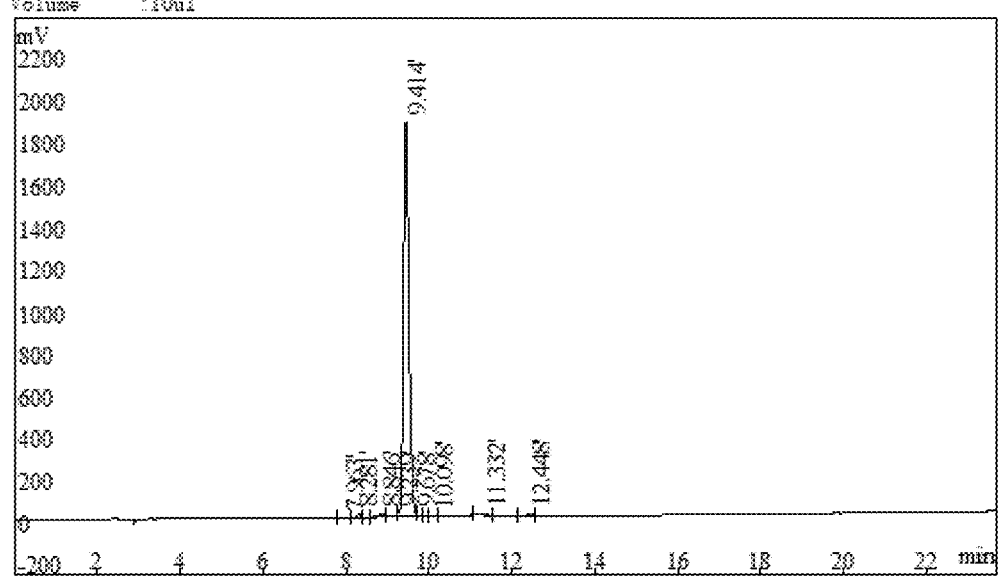
FIG. 5B provides the HPLC chromatogram for Compound 4.
Figure 6A:
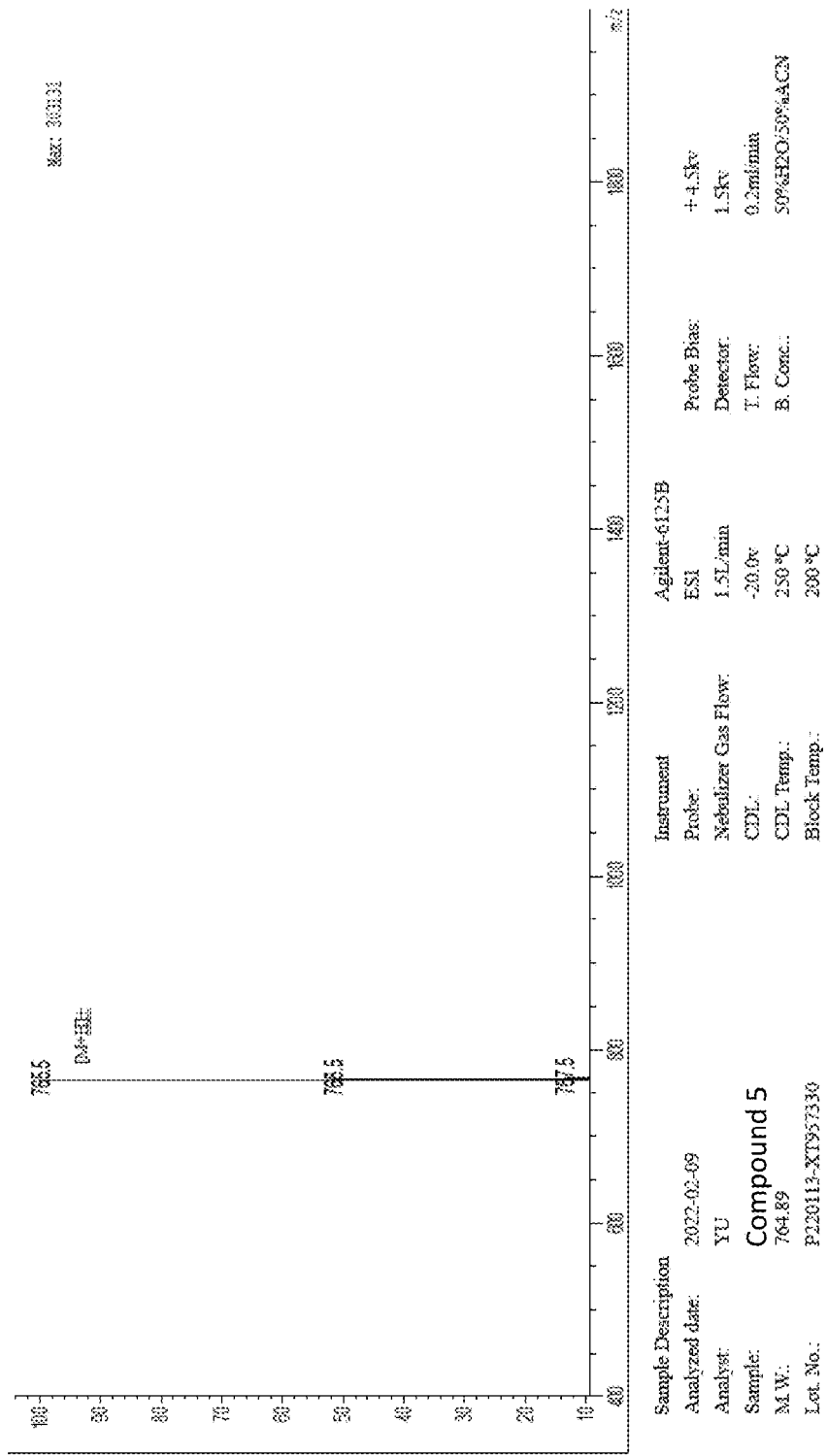
FIG. 6A provides the MS spectrum of Compound 5.
Figure 6B:
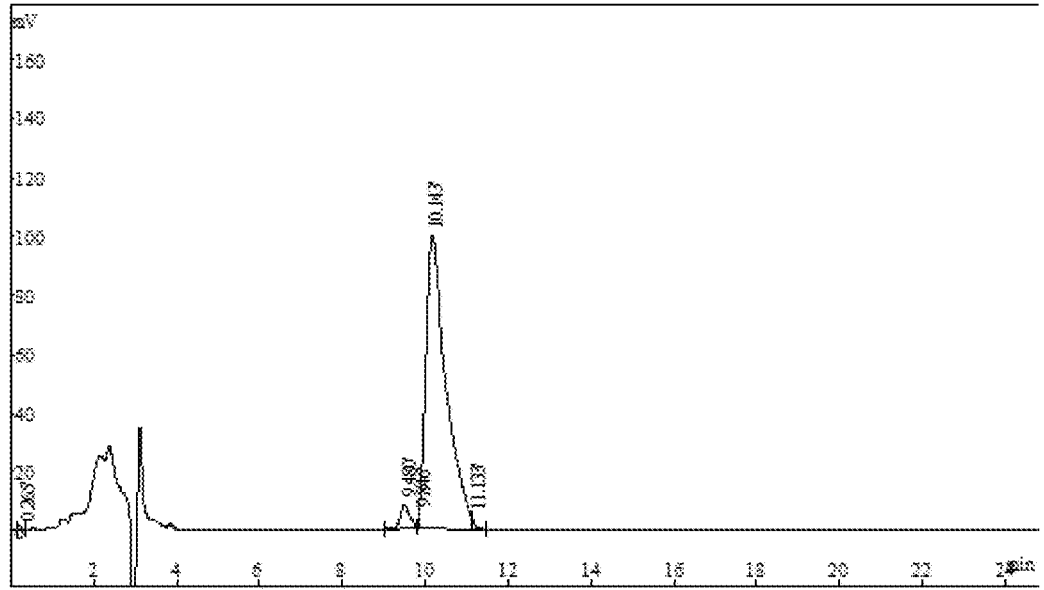
FIG. 6B provides the HPLC chromatogram for Compound 5.
Figure 7A:
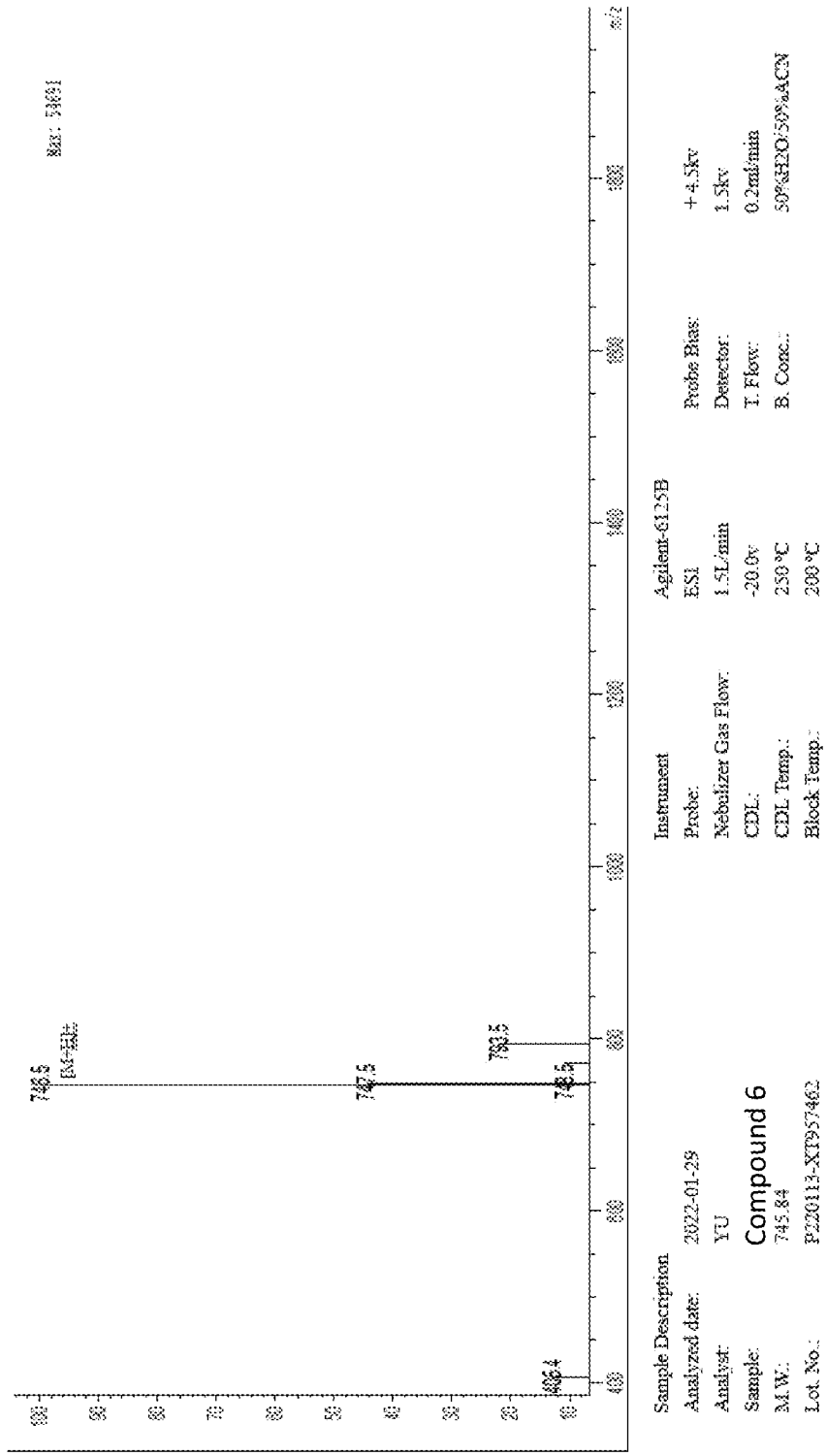
FIG. 7A provides the MS spectrum for Compound 6.
Figure 7B:
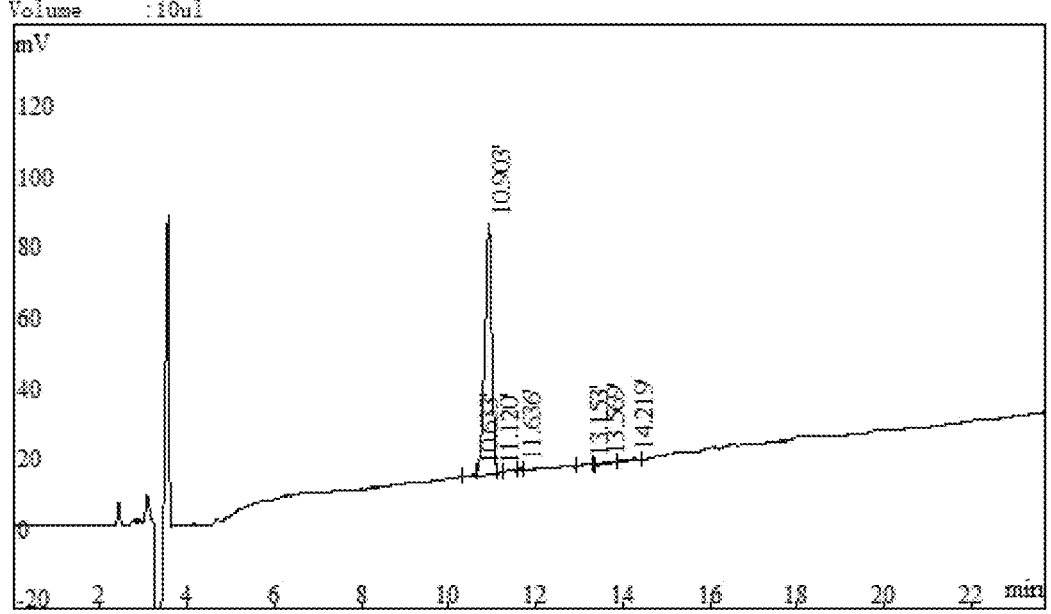
FIG. 7B provides the HPLC chromatogram for Compound 6.
Figure 8A:
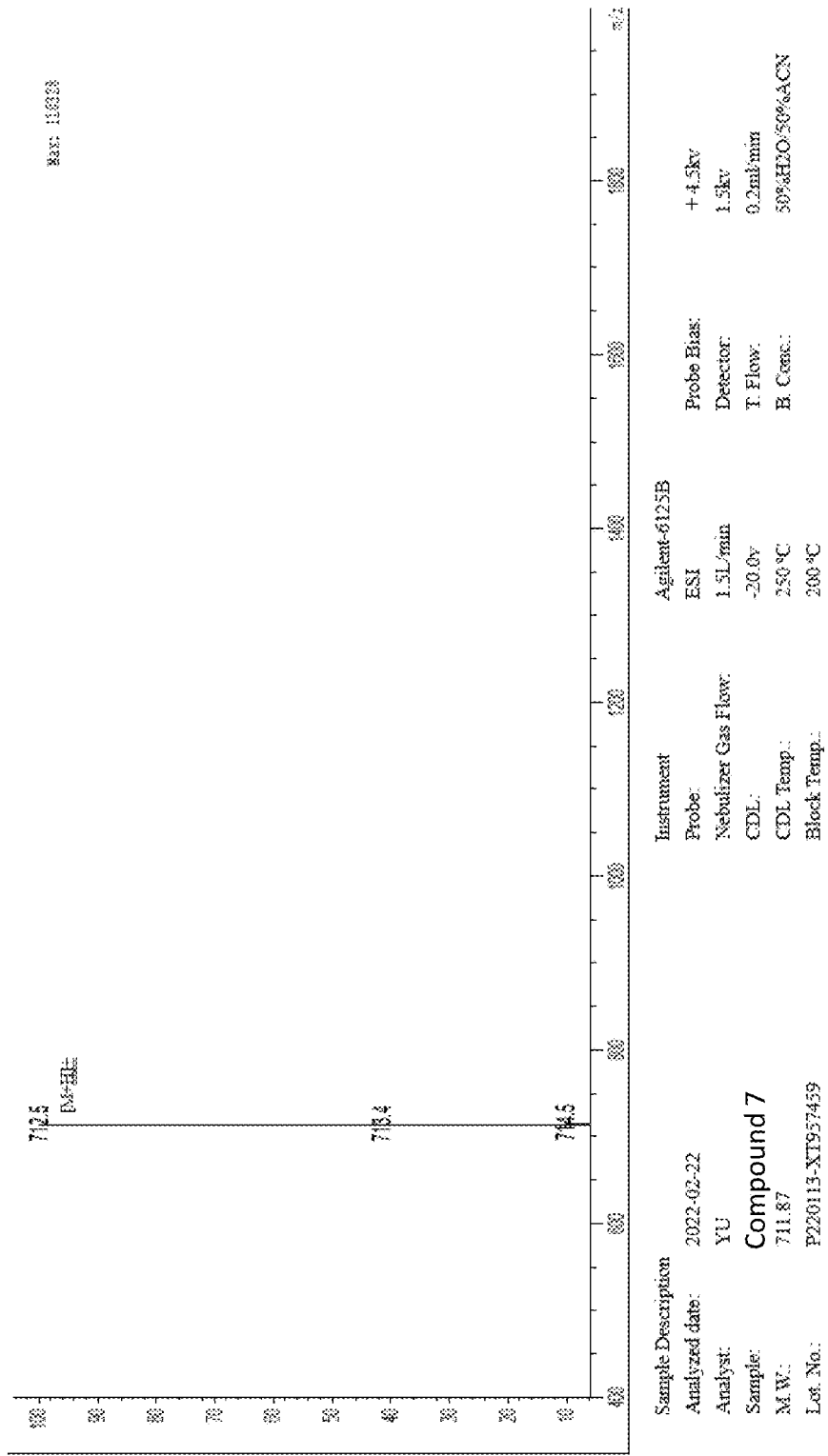
FIG. 8A provides the MS spectrum for Compound 7.
Figure 8B:
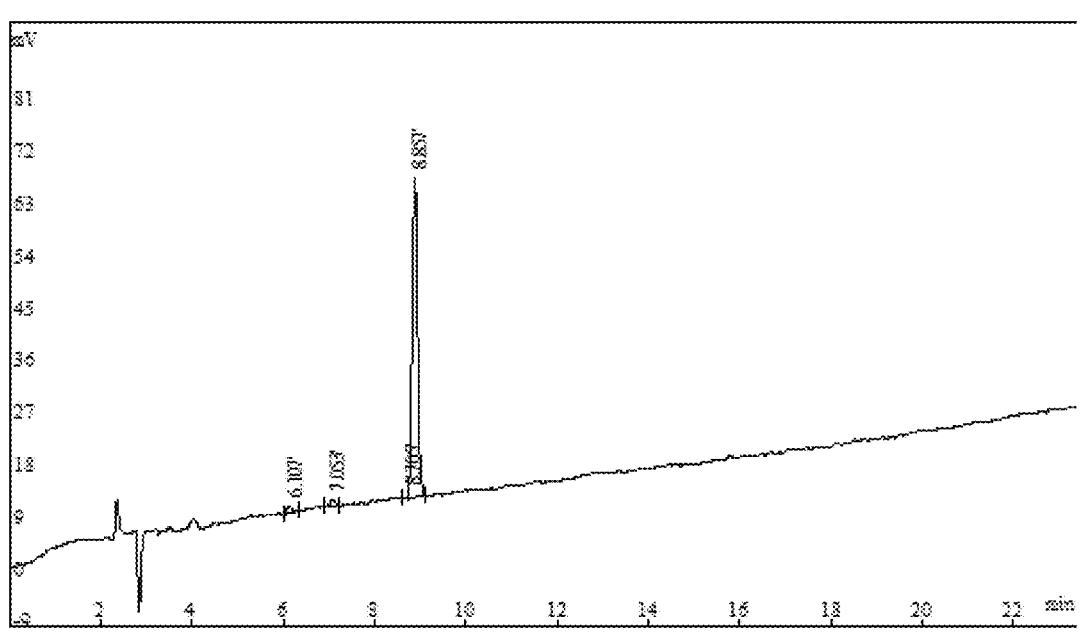
FIG. 8B provides the HPLC chromatogram for Compound 7.
Figure 9A:
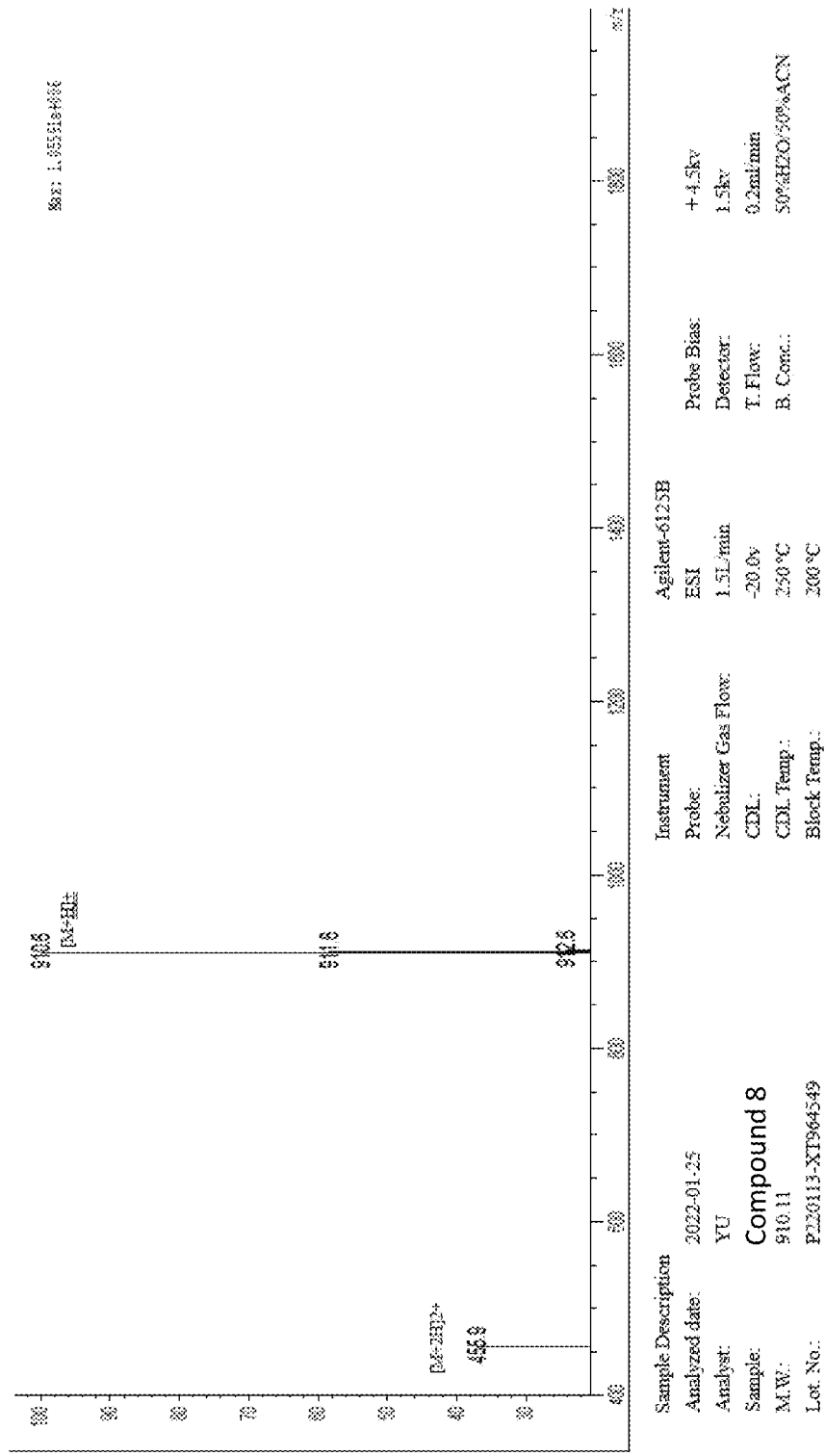
FIG. 9A provides the MS spectrum for Compound 8.
Figure 9B:
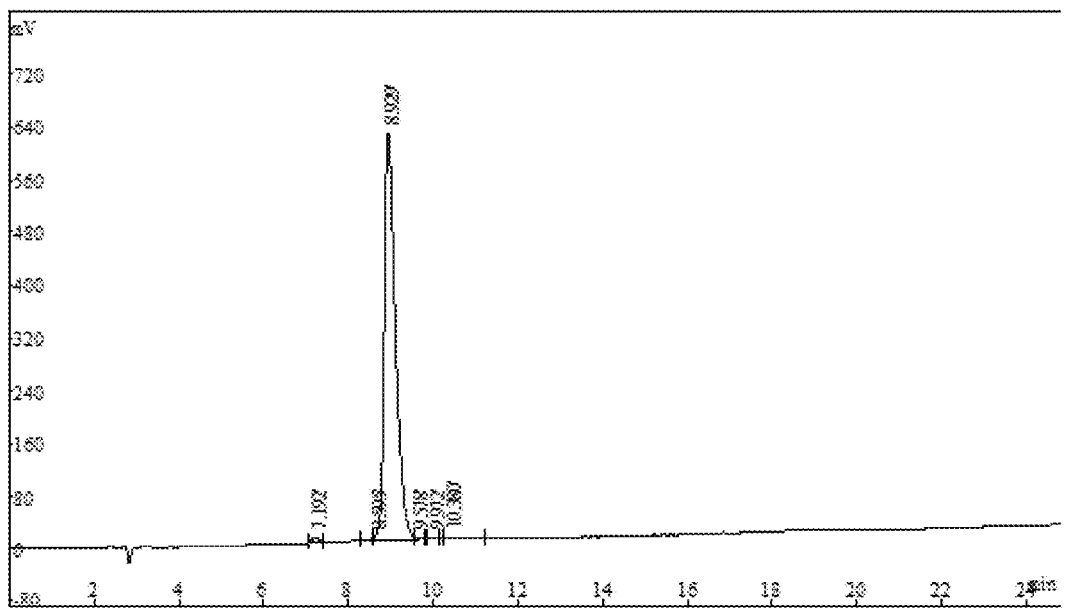
FIG. 9B provides the HPLC chromatogram for Compound 8.
Figure 10A:
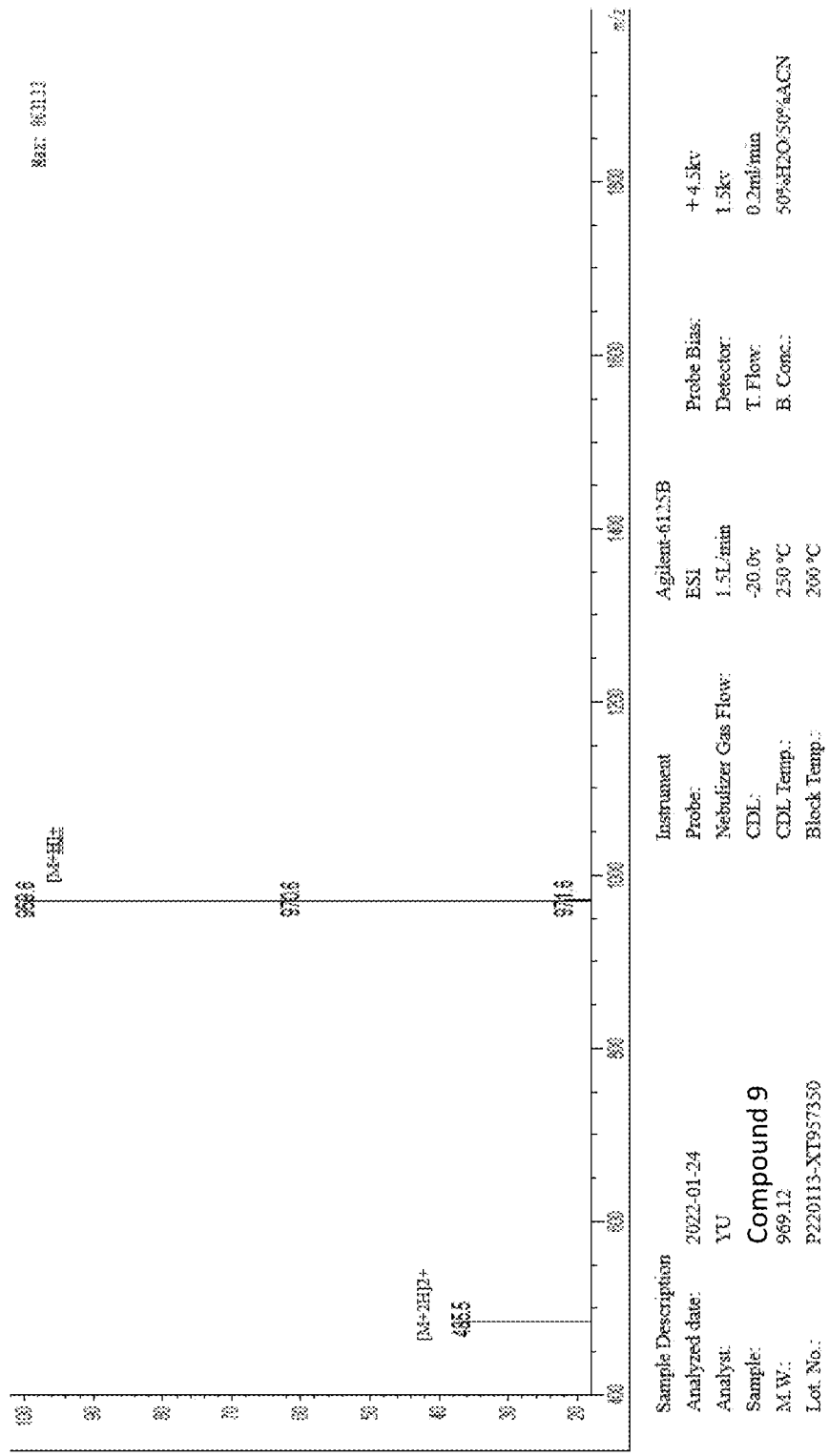
FIG. 10A provides the MS spectrum for Compound 9.
Figure 10B:
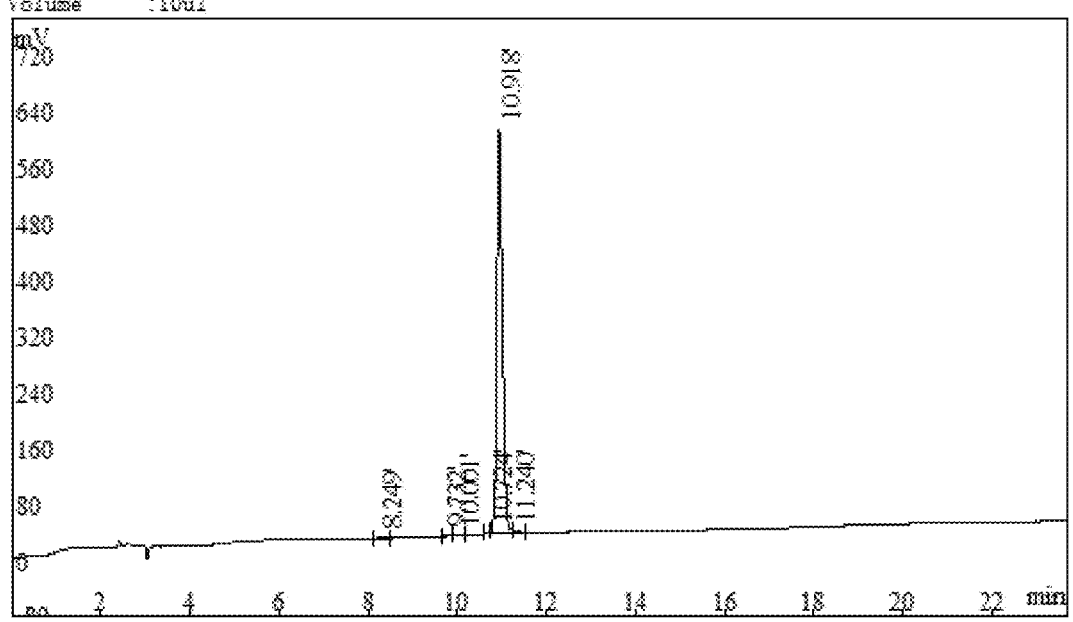
FIG. 10B provides the HPLC chromatogram for Compound 9.
Figure 11A:
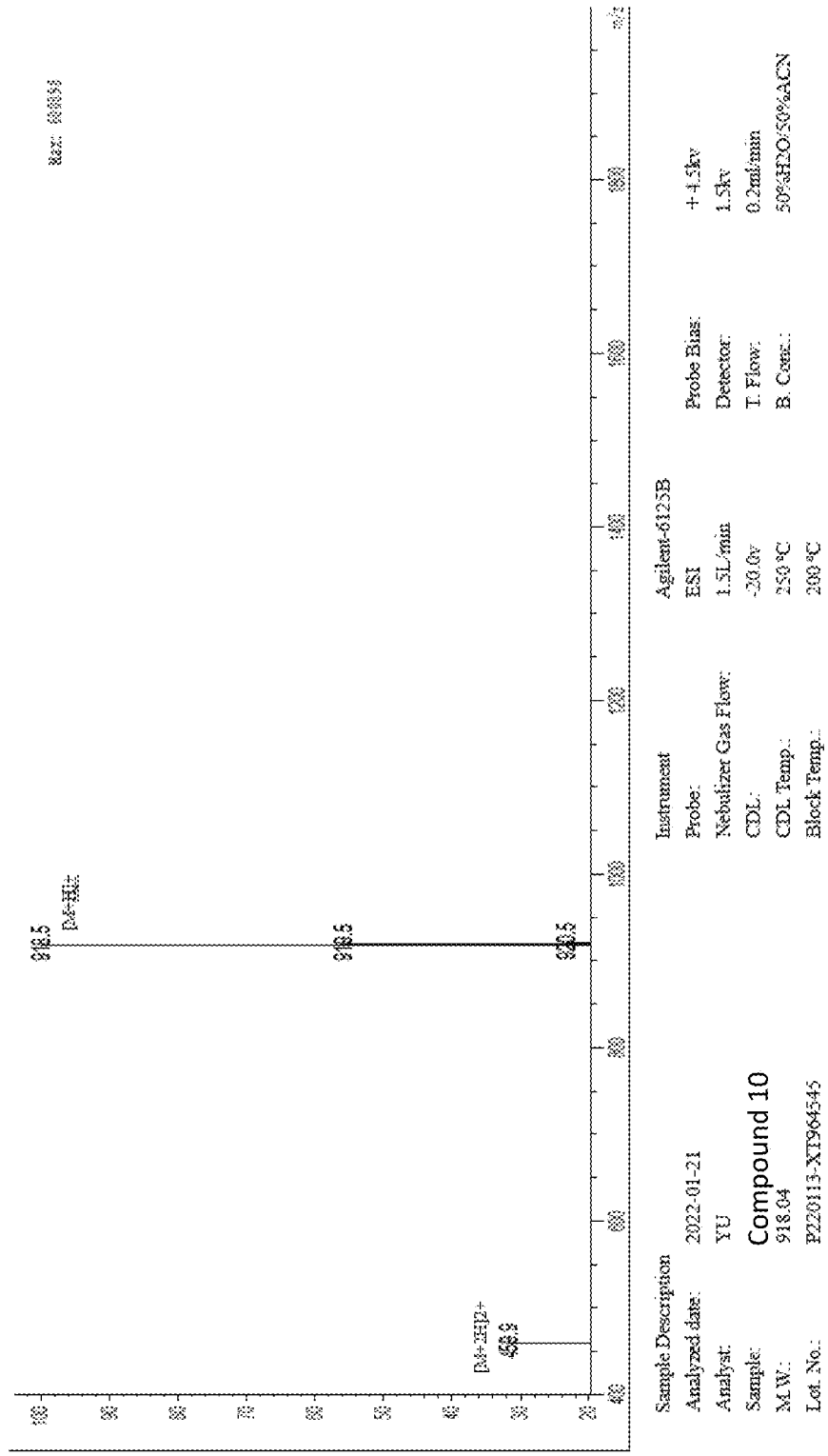
FIG. 11A provides the MS spectrum for Compound 10.
Figure 11B:
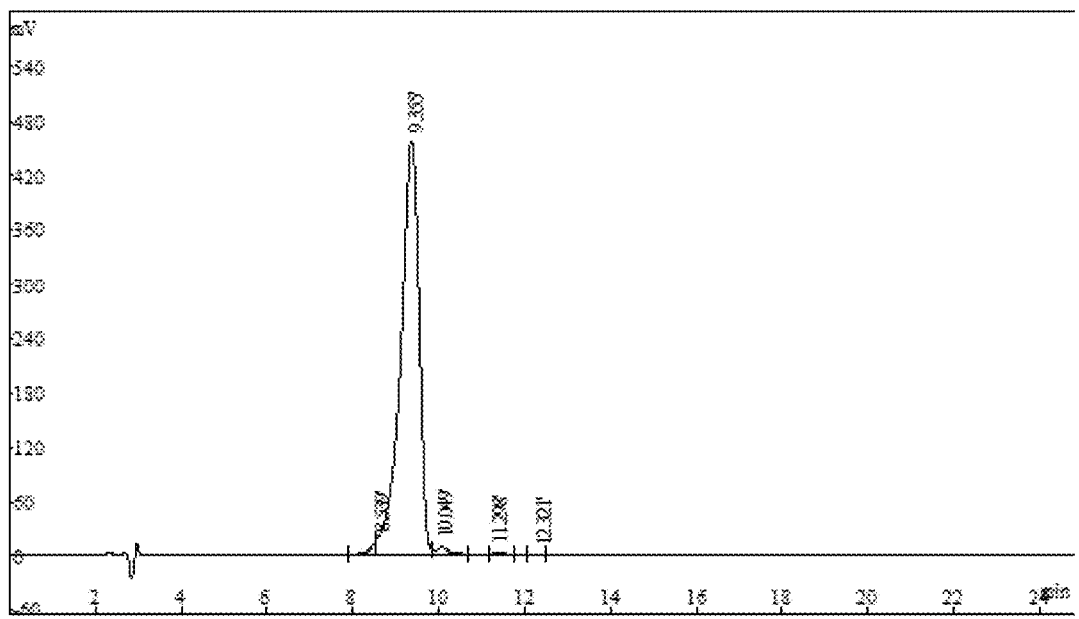
FIG. 11B provides the HPLC chromatogram for Compound 10.
Figure 12A:
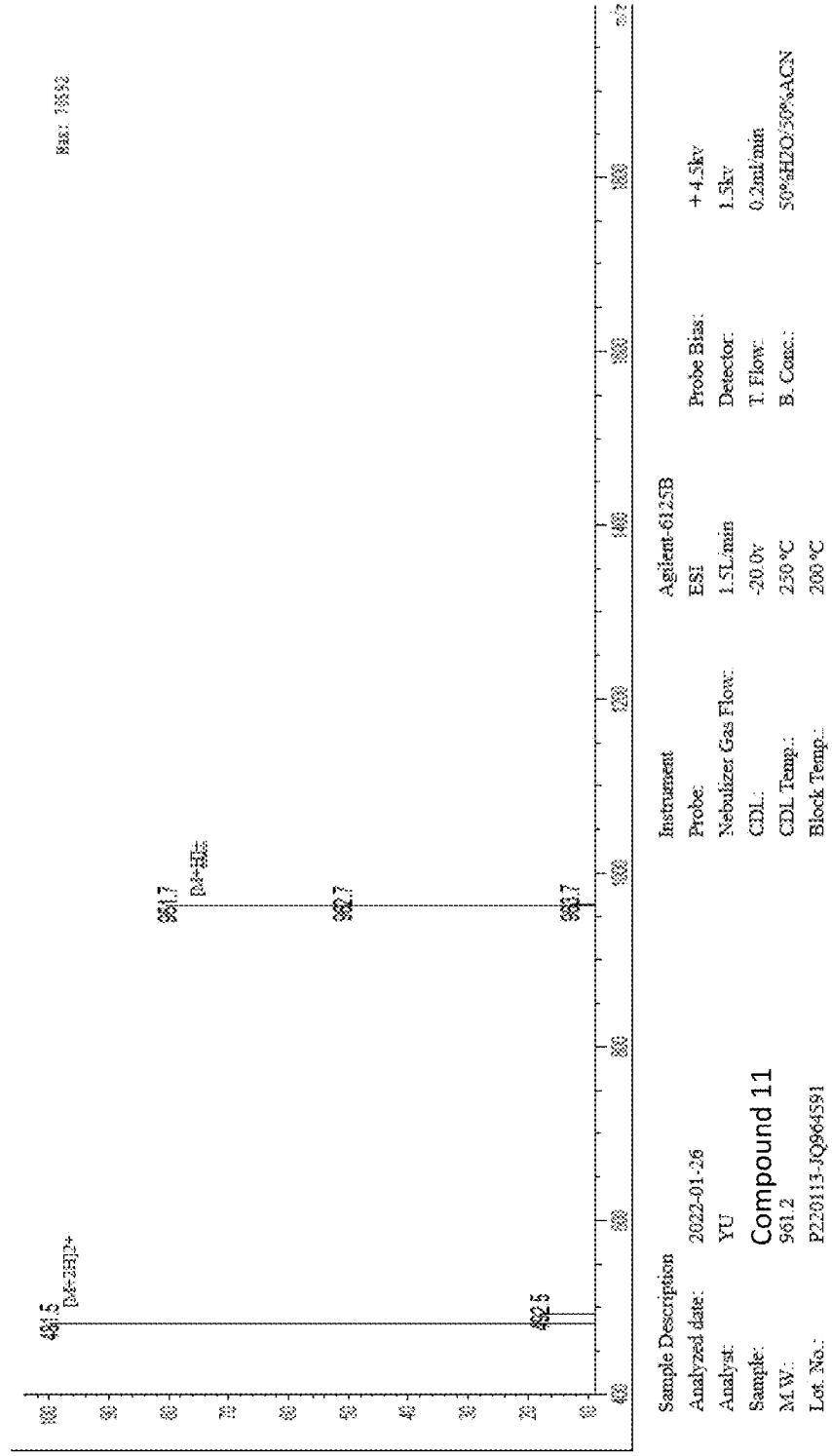
FIG. 12A provides the MS spectrum for Compound 11.
Figure 12B:
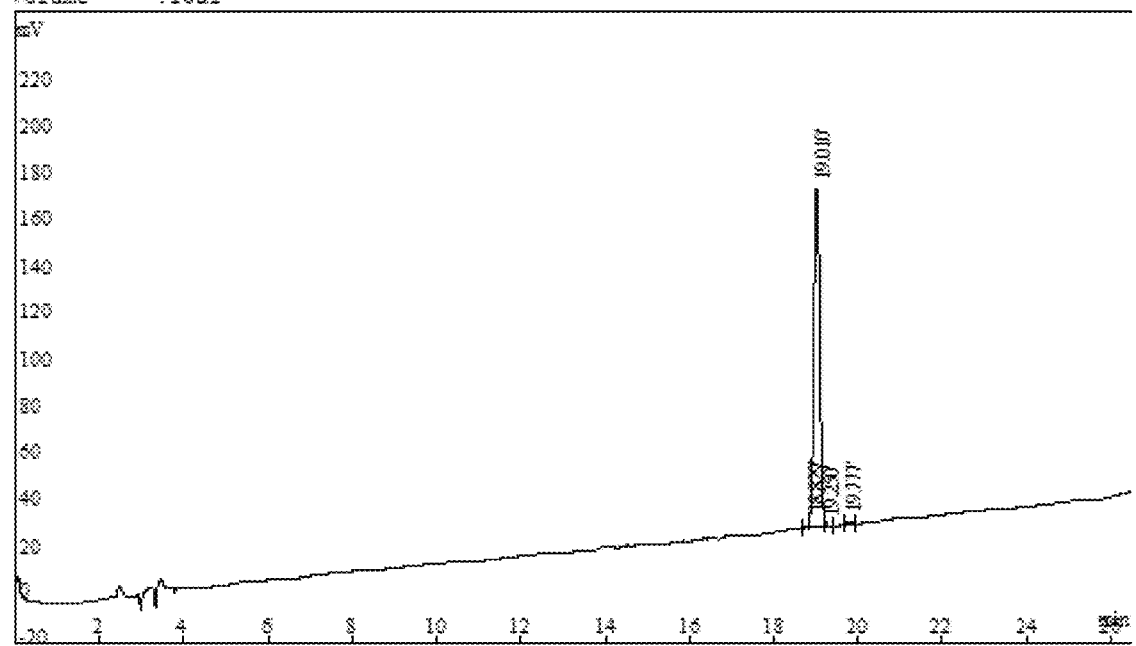
FIG. 12B provides the HPLC chromatogram for Compound 11.

The synthesized cyclic oligopeptides were analyzed for purity and structural characteristics by MS (Mass Spectrometry) (see, FIGS. 2A, 3A, 4A, 5A, 6A, 7A, 8A, 9A, 10A, 11A, and 12A) and HPLC (see, FIGS. 2B, 3B, 4B, 5B, 6B, 7B, 8B, 9B, 10B, 11B, and 12B). Exemplary structure and amino acid sequences of cyclic oligopeptides that bind to IL-13 are illustrated in Table 1.

TABLE 1

Structure and amino acid sequence of cyclic oligopeptides

| SEQ ID NO: | Structure | Amino Acid Sequence |
|---|---|---|
| 1 | 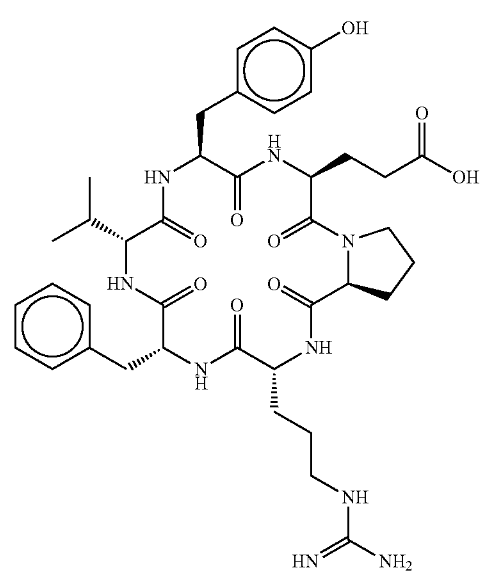 | D-Arg D-Phe D-Val Tyr Glu Pro (SEQ ID NO: 1) |

Compound 1

TABLE 1-continued

Structure and amino acid sequence of cyclic oligopeptides

| SEQ ID NO: | Structure | Amino Acid Sequence |
|---|---|---|
| 2 | Compound 2 | Arg Thr D-Val Glu D-Phe D-Pro (SEQ ID NO: 2) |
| 3 | Compound 3 | Glu D-Thr D-Val Trp D-Pro D-Pro (SEQ ID NO: 3) |
| 4 | Compound 4 | Arg Glu D-Val Trp D-Pro D-Pro (SEQ ID NO: 4) |

TABLE 1-continued
Structure and amino acid sequence of cyclic oligopeptides
| SEQ ID NO: | Structure | Amino Acid Sequence |
|---|---|---|
| 5 | 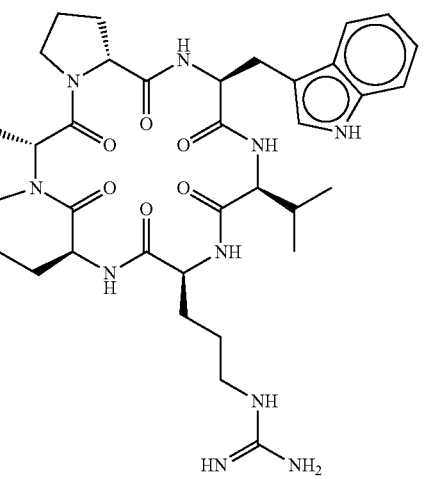<br>Compound 5 | Trp Val Arg Glu D-Pro D-Pro (SEQ ID NO: 5) |
| 6 | 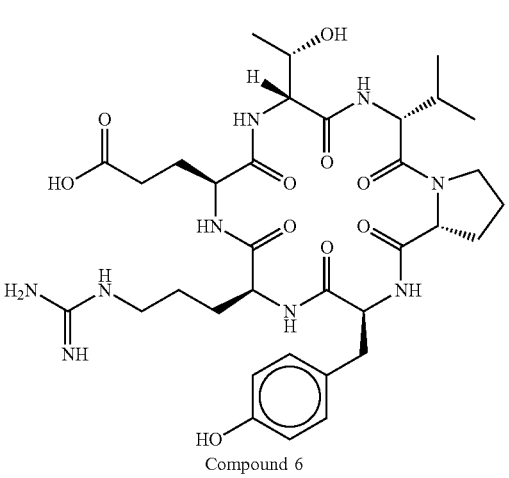<br>Compound 6 | Tyr Arg Glu D-Thr D-Val D-Pro (SEQ ID NO: 6) |
| 7 | 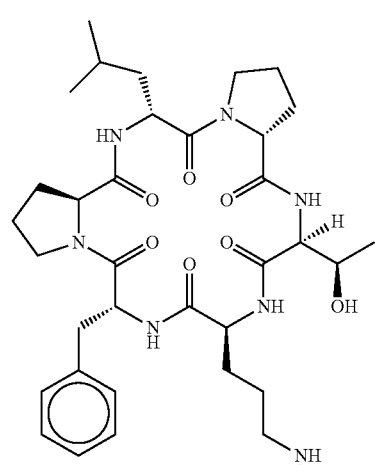<br>Compound 7 | Thr Arg D-Phe Pro D-Leu D-Pro (SEQ ID NO: 7) |

TABLE 1-continued
Structure and amino acid sequence of cyclic oligopeptides
| SEQ ID NO: | Structure | Amino Acid Sequence |
|---|---|---|
| 8 | 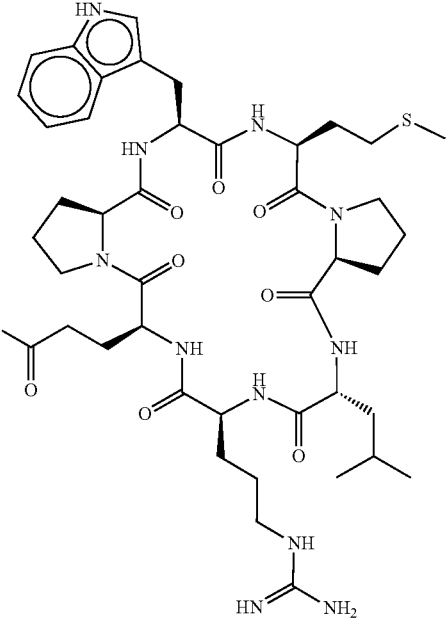Compound 8 | D-Leu Arg Glu Pro Trp Met Pro (SEQ ID NO: 8) |
| 9 | 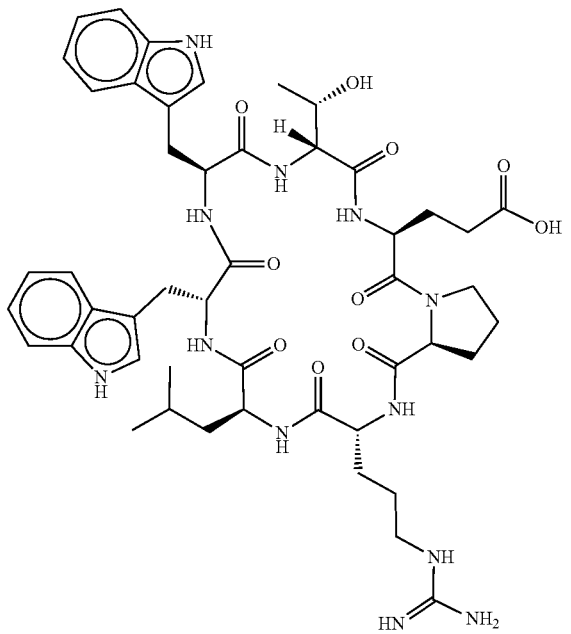Compound 9 | D-Arg Leu D-Trp Trp D-Thr Glu Pro (SEQ ID NO: 9) |

TABLE 1-continued

Structure and amino acid sequence of cyclic oligopeptides

| SEQ ID NO: | Structure | Amino Acid Sequence |
|---|---|---|
| 10 | 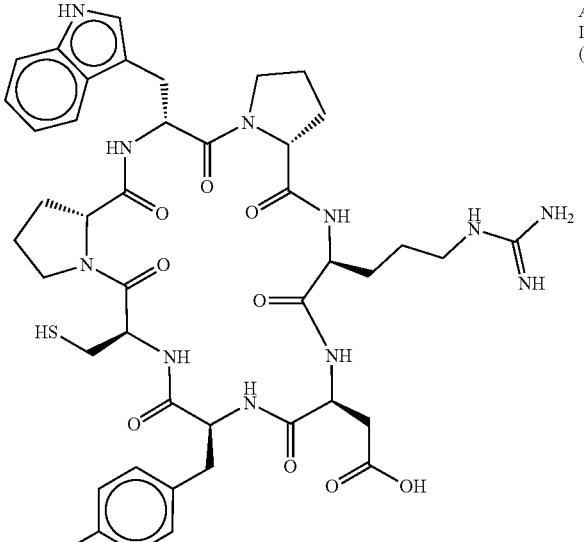<br>Compound 10 | Arg Asp Tyr Cys D-Pro D-Trp D-Pro (SEQ ID NO: 10) |
| 11 | 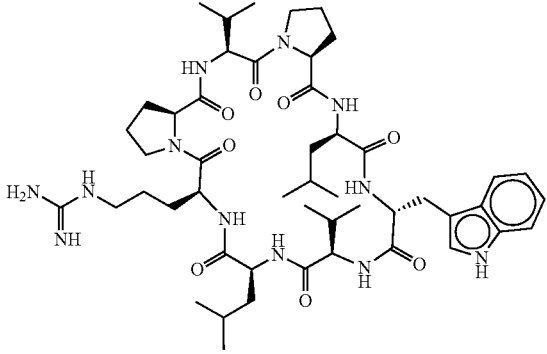<br>Compound 11 | Val Pro D-Leu D-Trp D-Val Leu Arg Pro (SEQ ID NO: 11) |

Example 2. Evaluation of Cyclic Oligopeptides by Surface Plasmon Resonance (SPR)

A SPR assay was conducted to determine the binding affinity of the cyclic oligopeptides generated in Example 1 for IL-13 using a BIAcore 8K plus instrument (GE Healthcare). Human IL-13 with an Fc-tag was immobilized onto the surfaces of Series S Sensor CM5 (GE Healthcare) chips in the range of 5000 resonance units (RU). The binding kinetics were performed at 25° C. with a flow rate of 30 µL/min. The cyclic oligopeptides were analyzed in running buffer comprising 20 mM PBS, 2.7 mM KCl, 37 mM NaCl, 0.0500 Surfactant P20, pH 7.4, 1% DMSO, starting at 100 µM with gradient of ten two-fold dilutions using solvent correction mode. The affinity between IL-13 and the cyclic oligopeptides, as demonstrated by $K_D$ values, was determined using the BIAcore 8K plus evaluation software.

Figure 2C:
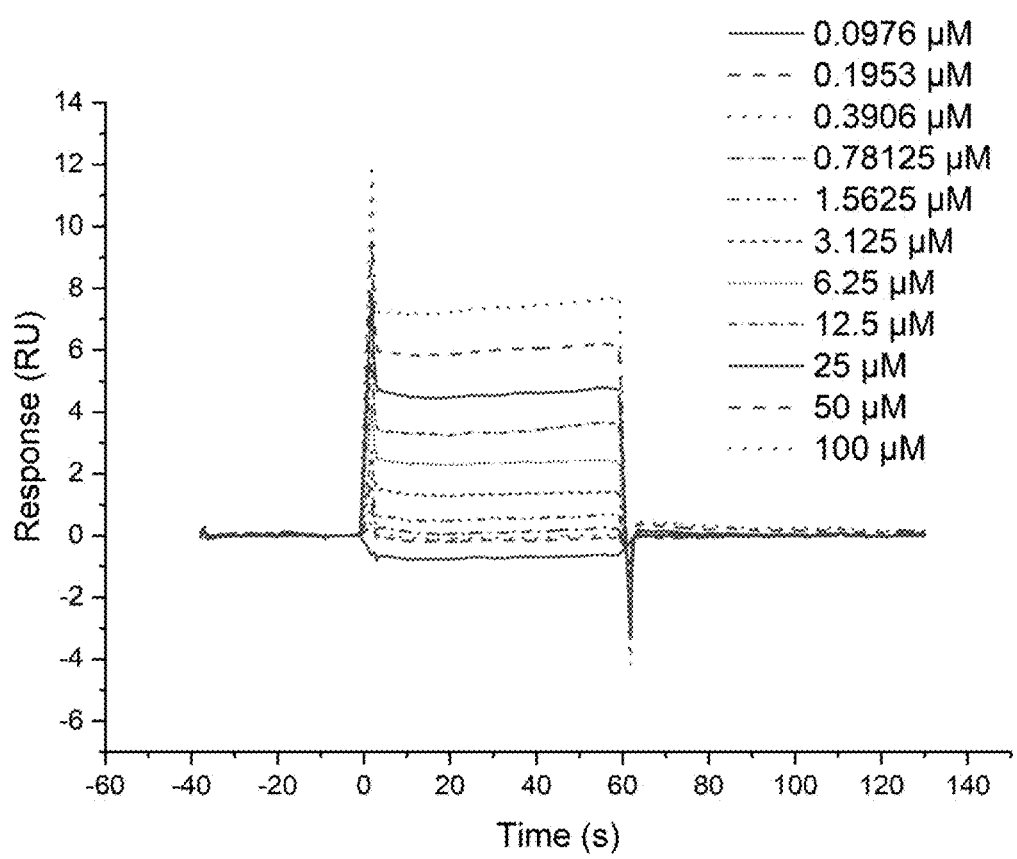
FIG. 2C provides surface plasmon resonance (SPR) assay curves showing the binding affinity of Compound 1 for IL-13, the x-axis represents time of reaction and y-axis represents altitude of response (Response Units).
Figure 3C:
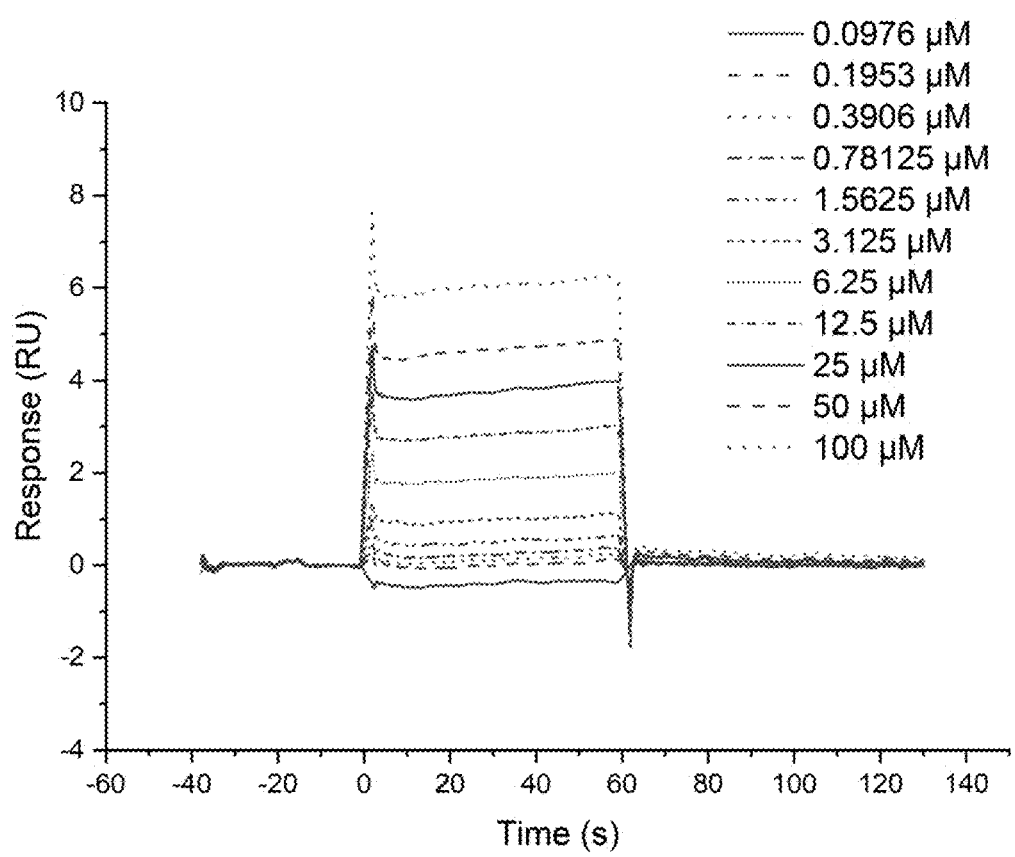
FIG. 3C provides SPR assay curves showing the binding affinity of Compound 2 for IL-13, the x-axis represents time of reaction and y-axis represents altitude of response (Response Units).
Figure 4C:
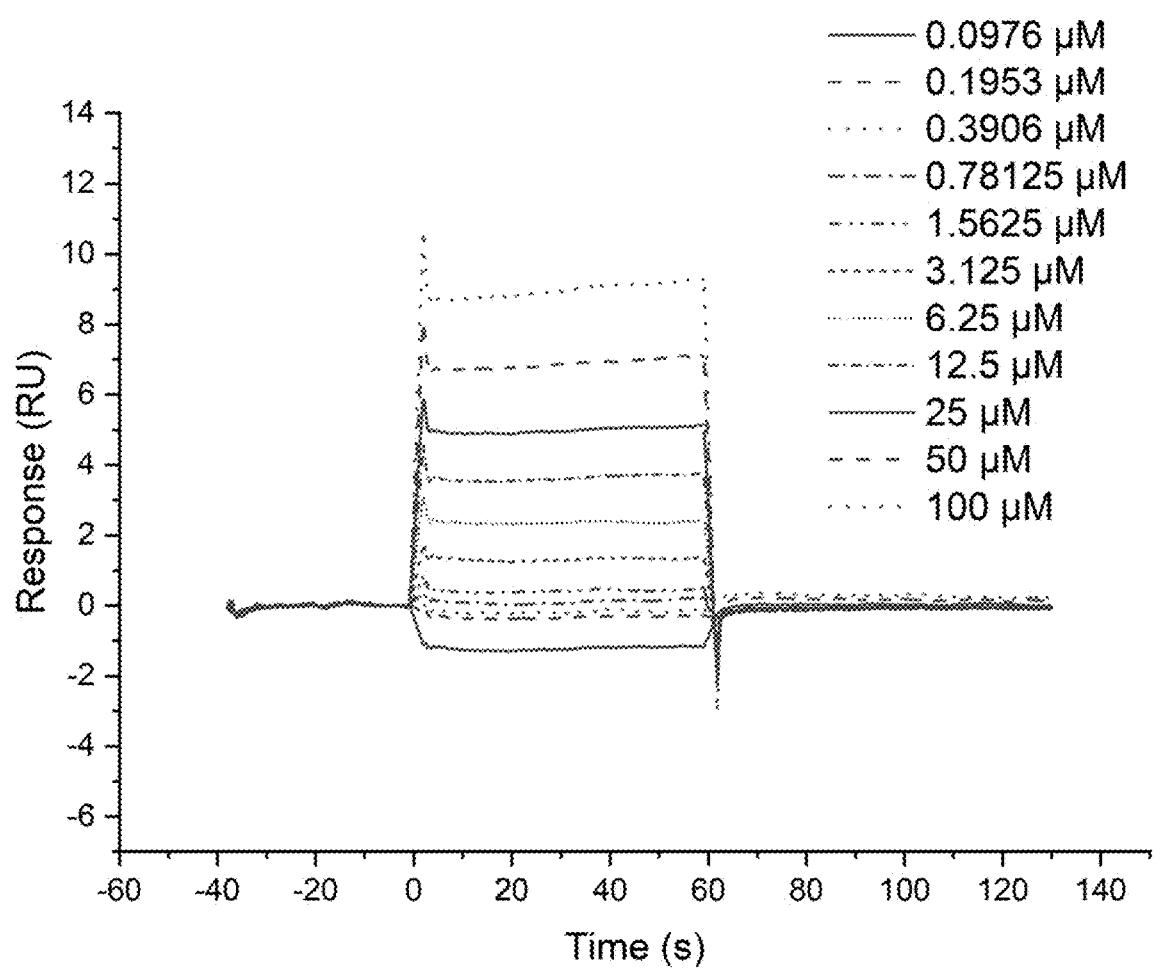
FIG. 4C provides SPR assay curves showing the binding affinity of Compound 3 for IL-13, the x-axis represents time of reaction and y-axis represents altitude of response (Response Units).
Figure 5C:
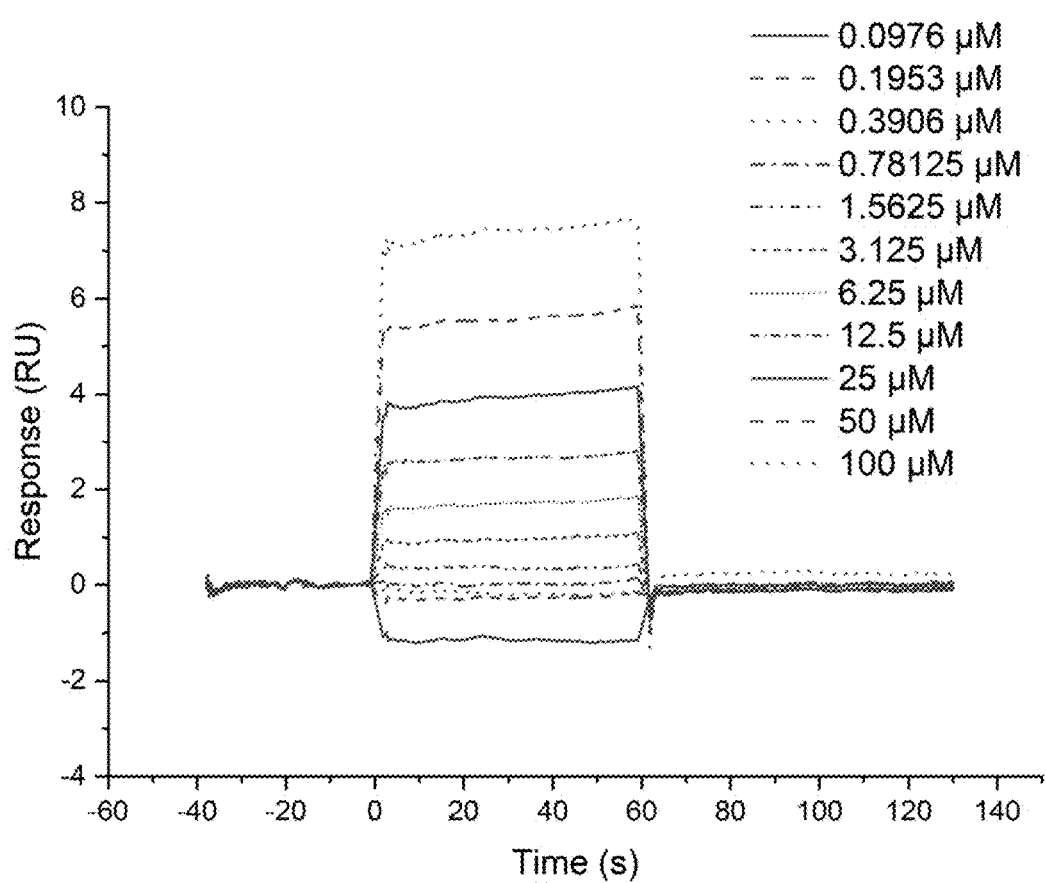
FIG. 5C provides SPR assay curves showing the binding affinity of Compound 4 for IL-13, the x-axis represents time of reaction and y-axis represents altitude of response (Response Units).
Figure 6C:
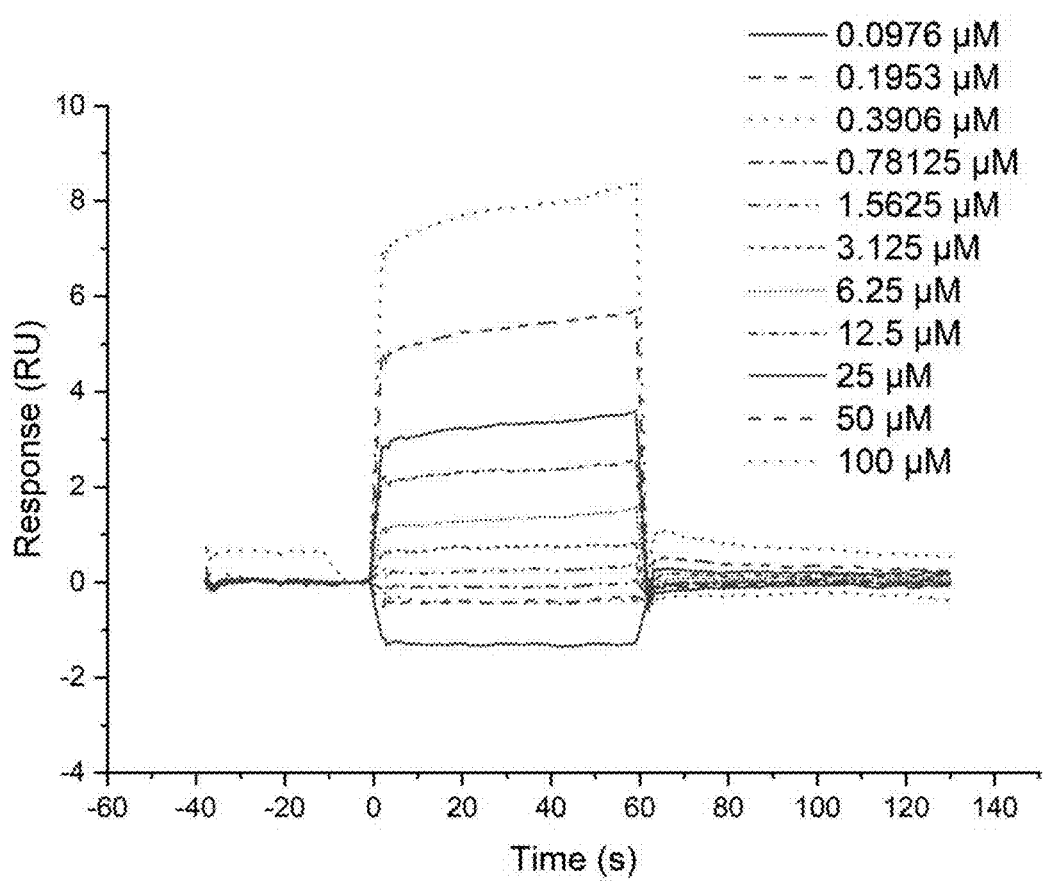
FIG. 6C provides SPR assay curves showing the binding affinity of Compound 5 for IL-13, the x-axis represents time of reaction and y-axis represents altitude of response (Response Units).
Figure 7C:
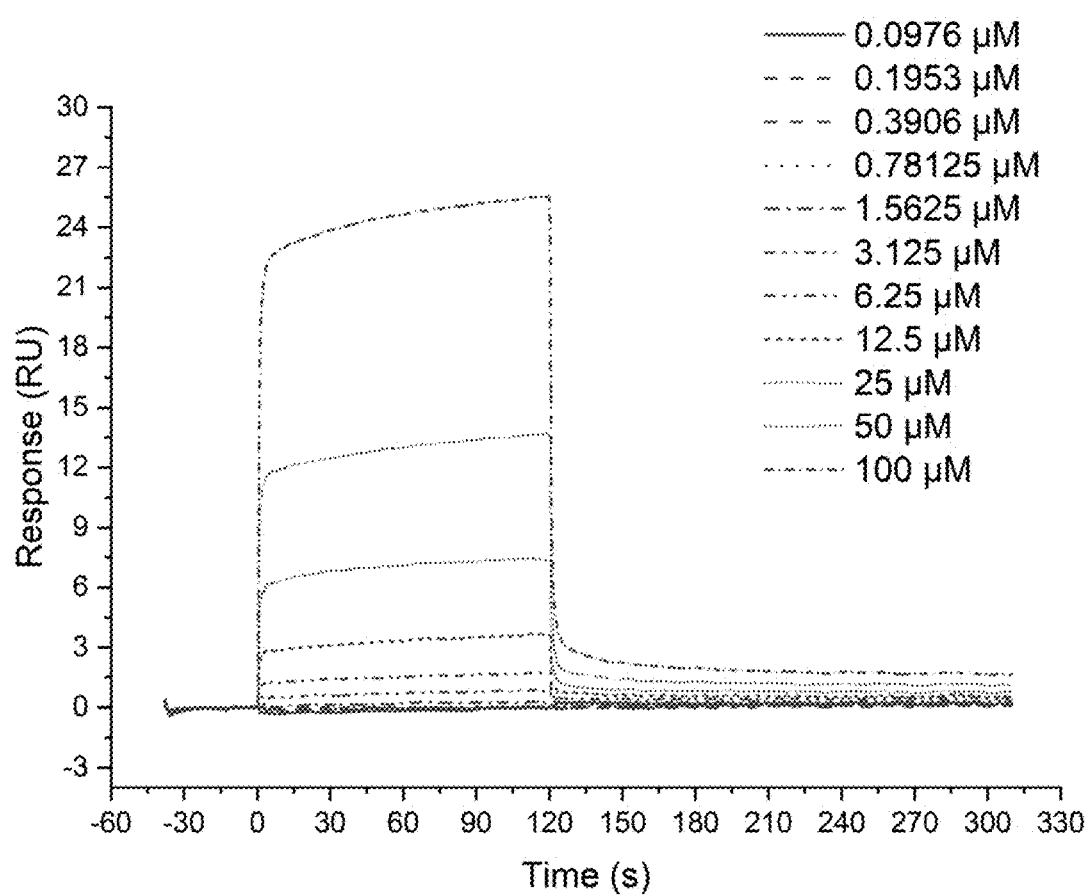
FIG. 7C provides SPR assay curves showing the binding affinity of Compound 6 for IL-13, the x-axis represents time of reaction and y-axis represents altitude of response (Response Units).
Figure 8C:
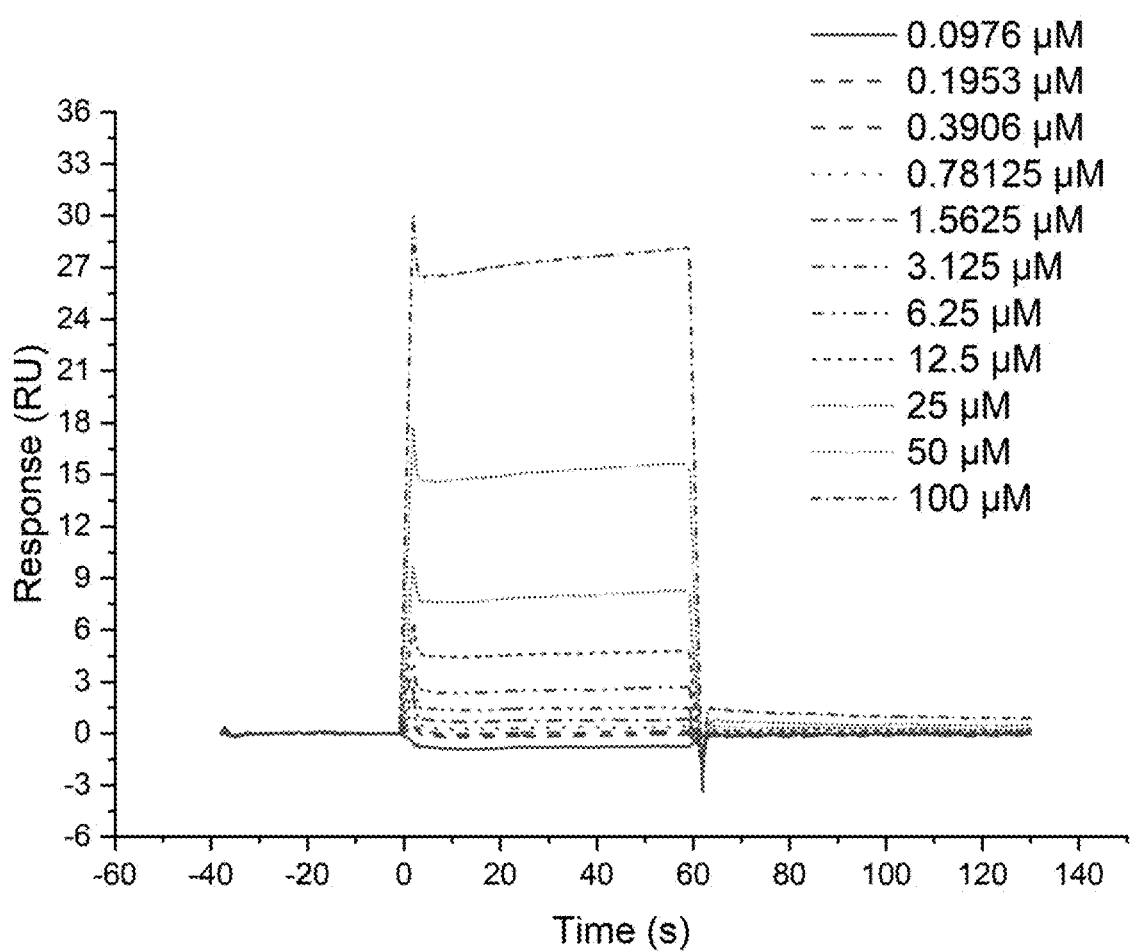
FIG. 8C provides SPR assay curves showing the binding affinity of Compound 7 for IL-13, the x-axis represents time of reaction and y-axis represents altitude of response (Response Units).
Figure 9C:
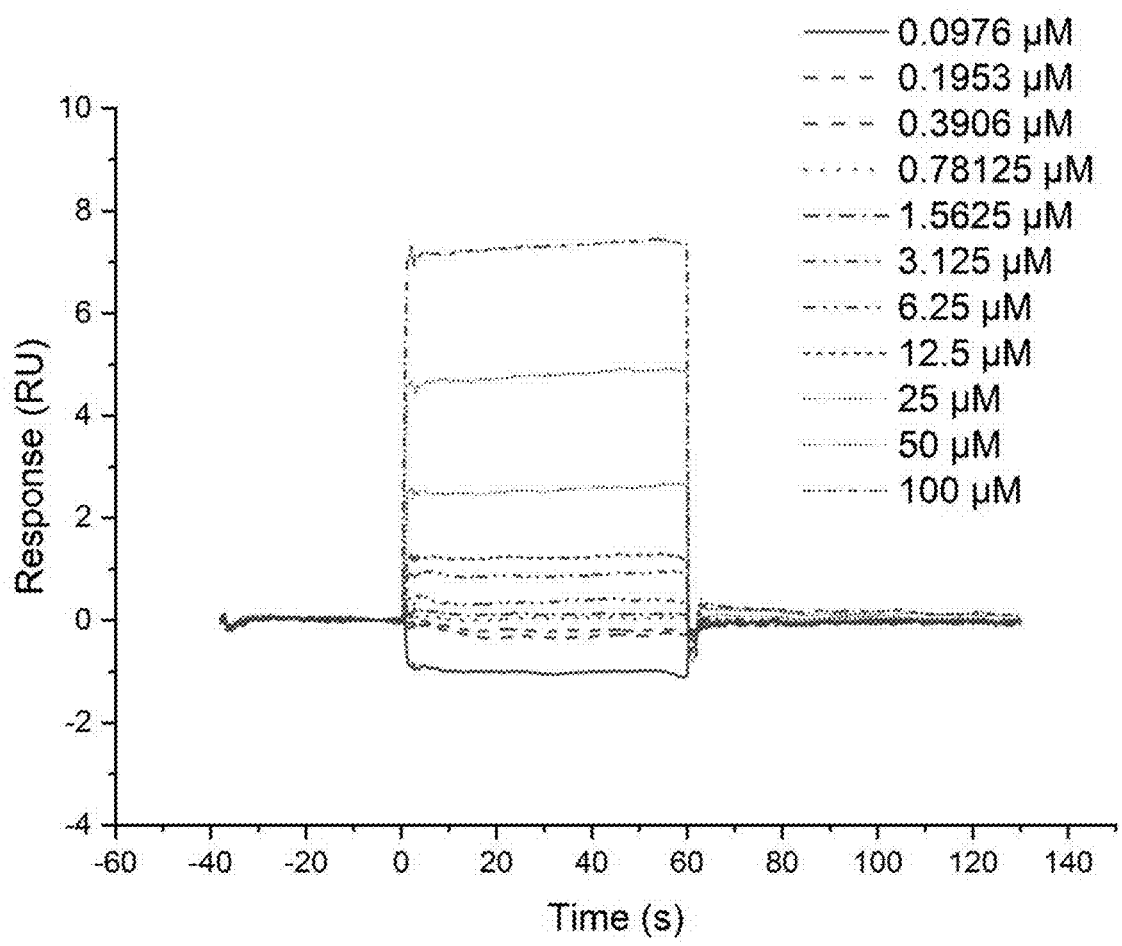
FIG. 9C provides SPR assay curves showing the binding affinity of Compound 8 for IL-13, the x-axis represents time of reaction and y-axis represents altitude of response (Response Units).
Figure 10C:
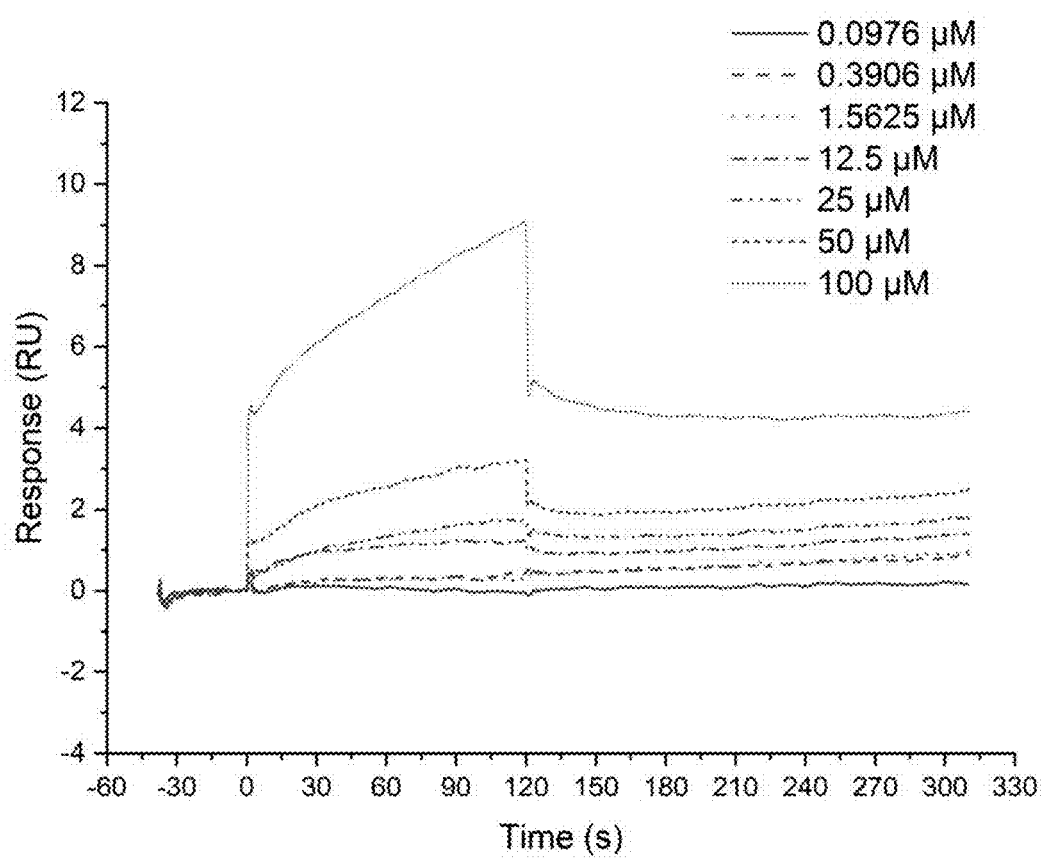
FIG. 10C provides SPR assay curves showing the binding affinity of Compound 9 for IL-13, the x-axis represents time of reaction and y-axis represents altitude of response (Response Units).
Figure 11C:
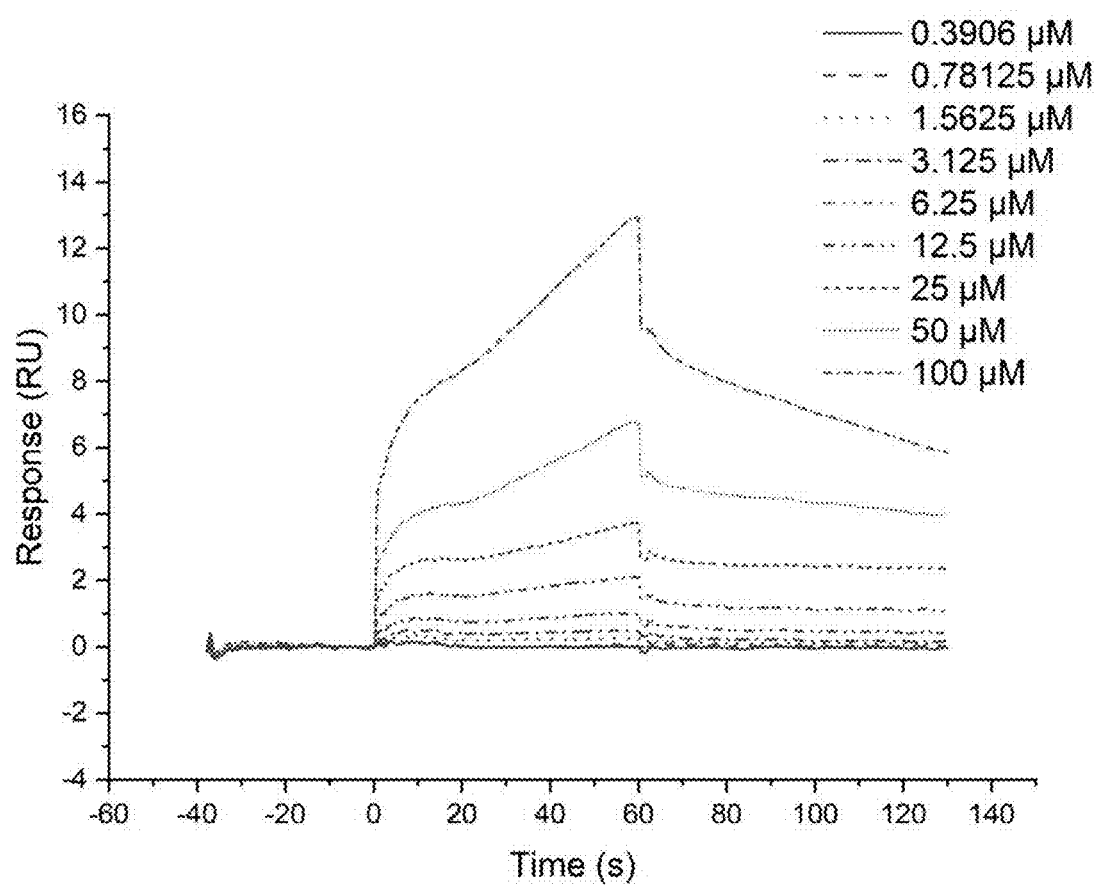
FIG. 11C provides SPR assay curves showing the binding affinity of Compound 10 for IL-13, the x-axis represents time of reaction and y-axis represents altitude of response (Response Units).
Figure 12C:
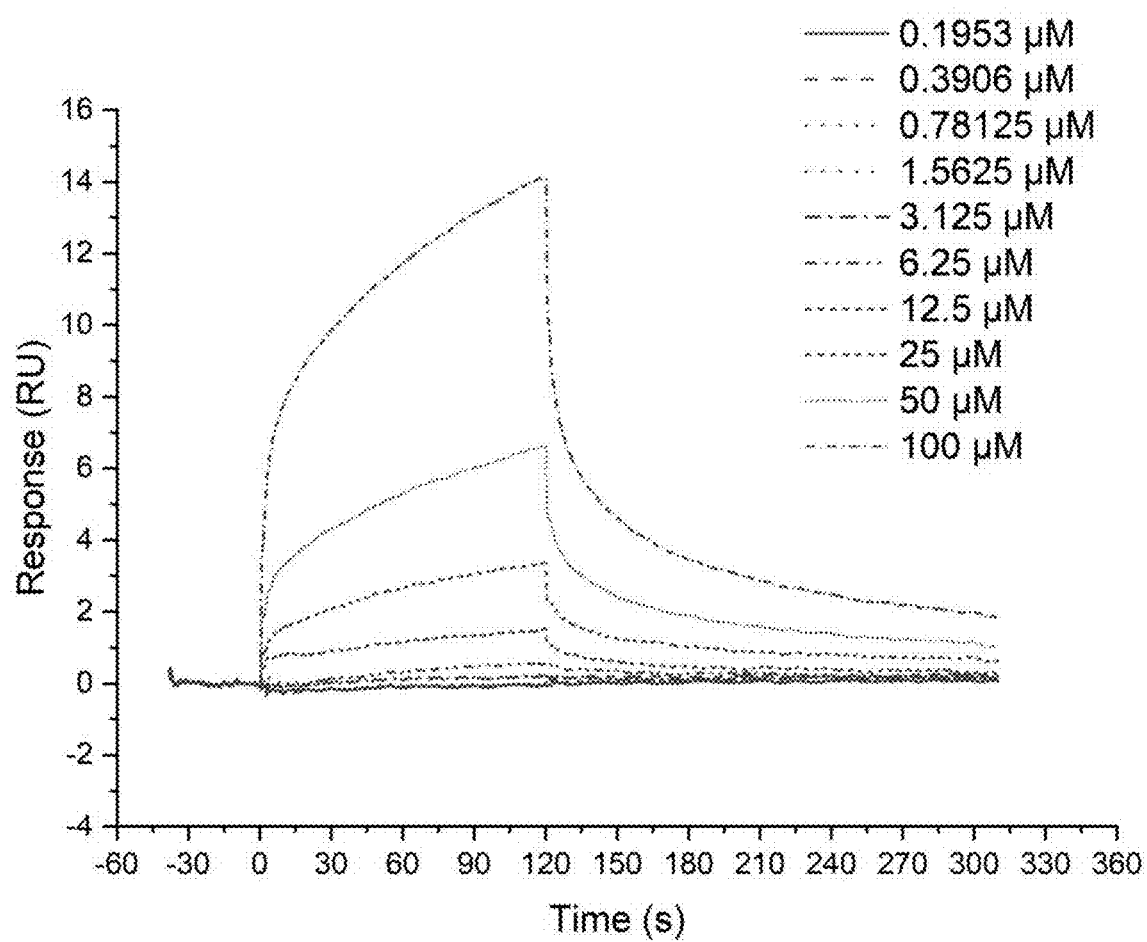
FIG. 12C provides SPR assay curves showing the binding affinity of Compound 11 for IL-13, the x-axis represents time of reaction and y-axis represents altitude of response (Response Units).

The efficiency and effectiveness of SPR assay were confirmed using tralokinumab, a monoclonal antibody against IL-13, as a positive control. FIGS. 2C, 3C, 4C, 5C, 6C, 7C, 8C, 9C, 10C, 11C, and 12C provide SPR response curves for the cyclic oligopeptides generated in Example 1, wherein the x-axis represents time of reaction and y-axis represents altitude of response (Response Units). As summarized in Table 2, infra, the SPR results demonstrate that the exemplary cyclic oligopeptides of this disclosure bind to IL-13 with $K_D$ values ranging from 16 to 622 µM.

TABLE 2

Binding Affinity ($K_D$) of exemplary cyclic oligopeptides for IL-13.

| Cyclic Oligopeptide | KD |
|---|---|
| Compound 1 | 16 µM |
| Compound 2 | 17.4 µM |
| Compound 3 | 22.8 µM |
| Compound 4 | 26.2 µM |
| Compound 5 | 47.1 µM |
| Compound 6 | 55.4 µM |
| Compound 7 | 85.1 µM |
| Compound 8 | 99.5 µM |
| Compound 9 | 337 µM |
| Compound 10 | 368 µM |

TABLE 2-continued

Binding Affinity ($K_D$) of exemplary cyclic oligopeptides for IL-13.

| Cyclic Oligopeptide | KD |
|---|---|
| Compound 11 | 622 μM |
| Tralokinumab | 309 pM |

Example 3. Skin Permeability of Cyclic Oligopeptides

Skin permeability of the cyclic oligopeptides generated in Example 1 was measured using Transdermal Diffusion Tester (TK-12D, Shanghai Kai Kai Industrial Co Ltd) and artificial skin (Start M, Merck). Three parallel experimental groups were set up for each sample. The skin permeability of cyclic oligopeptides was evaluated by the following steps:

1) 2.0 mg cyclic oligopeptide was weighed and dissolved in 100 μL DMSO. Three parallel experimental groups were set up for each cyclic oligopeptide. The cyclic oligopeptide-containing solution was then slowly added dropwise to 1900 μL 1×PBS solution and mixed evenly to prepare a PBS solution with a final concentration of 1.0 mg/mL cyclic polypeptide.
2) A magnetron was inserted into a Franz Cell diffusion cell, and an artificial skin was sandwiched in the middle of the diffusion cell with the smooth side of the artificial skin facing up. The diffusion cell was then fixed with clamps after assembly.
3) 7.75 ml 1×PBS solution were then added to the diffusion cell without generating bubbles in the diffusion cell. The sampling port of the diffusion cell was then sealed with parafilm to reduce evaporation.
4) The temperature of a Transdermal Diffusion Tester was then set to 32° C., and the magneton speed was set to 180 r/min.
5) The assembled diffusion cell was then put into the Transdermal Diffusion Tester and preheated for 5-10 mins.
6) 400 μL of 1.0 mg/mL cyclic oligopeptide solution prepared in step 1) was then added to the upper chamber of the diffusion cell, making it evenly dispersed on the surface of the artificial skin without air bubbles. The top port of the diffusion cell was then covered with parafilm to reduce evaporation.
7) Starting from the time of adding the cyclic oligopeptide solution, samples of about 0.5 mL of the receiving solution were taken at six time points, 1 h, 2 h, 4 h, 8 h, 12 h and 24 h, using a plastic dropper to take out the samples from the sampling port of the diffusion cell. 0.5 mL of 1×PBS solution was added into the diffusion cell to restore the initial volume of the receiving solution. When sampling, the diffusion cell was tilted appropriately to avoid the generation of bubbles. The samples were then numbered and store at −20° C.
8) A BCA Assay (Micro BCA Protein Assay Kit, Thermo Scientific) was conducted to measure the concentration of cyclic oligopeptide in samples obtained in step 7) (Actual Concentration of the cyclic oligopeptide at the particular time point). Three parallel groups were used. The weight of cyclic oligopeptide in each sample obtained in step 7) equals to Actual Concentration×0.5 mL.
9) Permeation rate of each cyclic oligopeptide at each time point was calculated according to the following equation:

Permeation rate (%) =

$$\frac{7.75 \times \text{Actual Concentration} + \sum \text{weight of cyclic oligopeptide in previous samples}}{0.4} \times 100\%$$

Figure 2D:
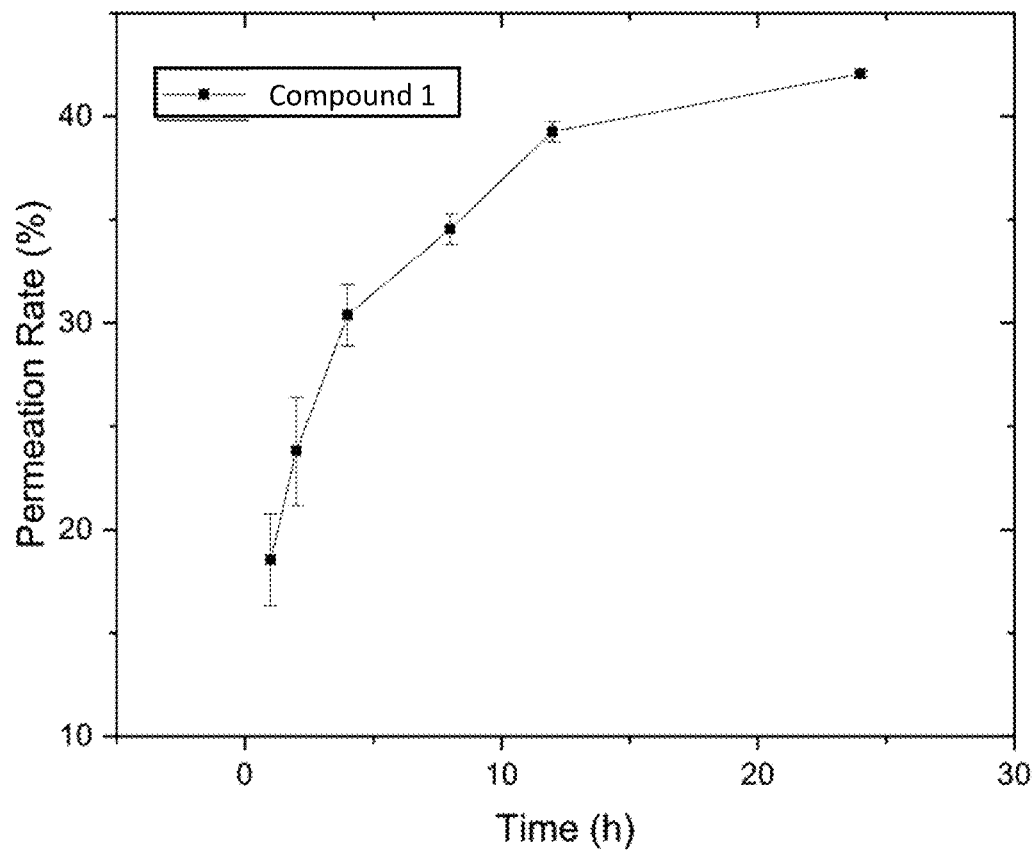
FIG. 2D illustrates skin permeation rate of Compound 1 for up to 24 hours.
Figure 3D:
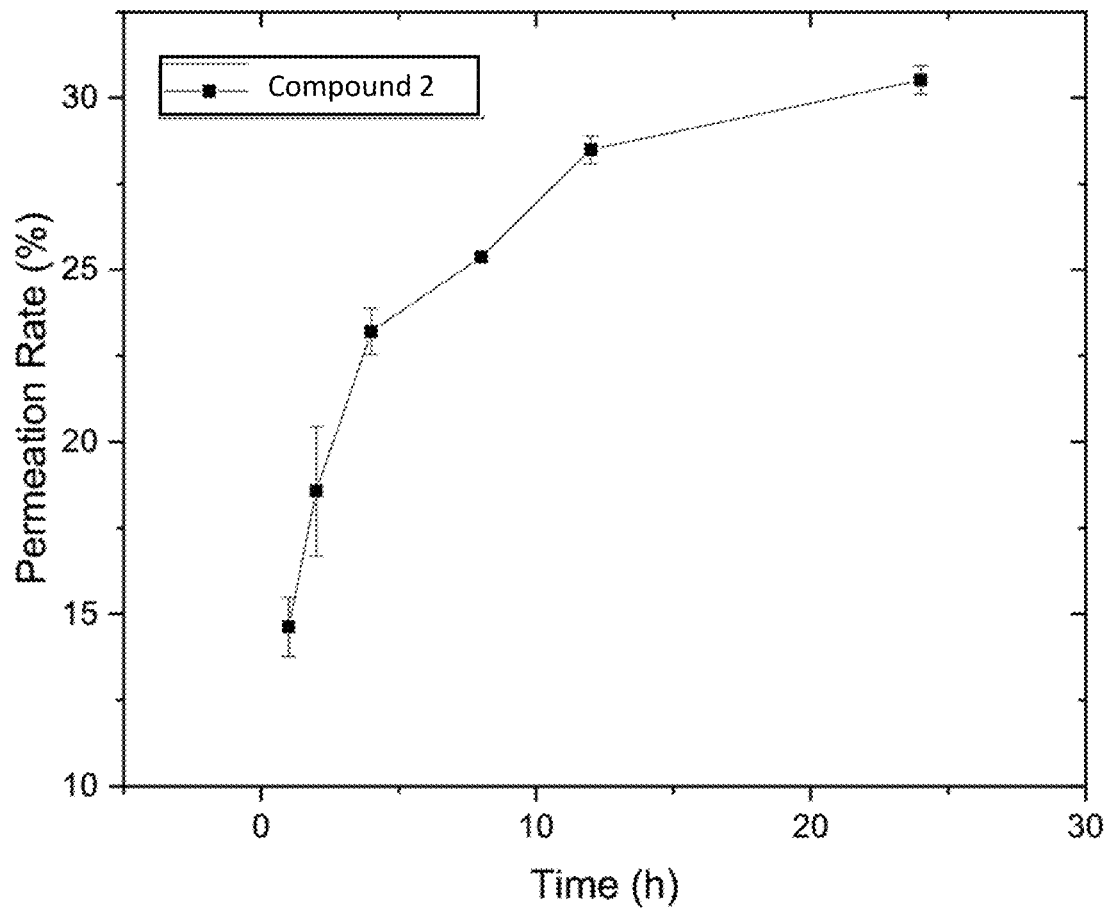
FIG. 3D illustrates skin permeation rate of Compound 2 for up to 24 hours.
Figure 4D:
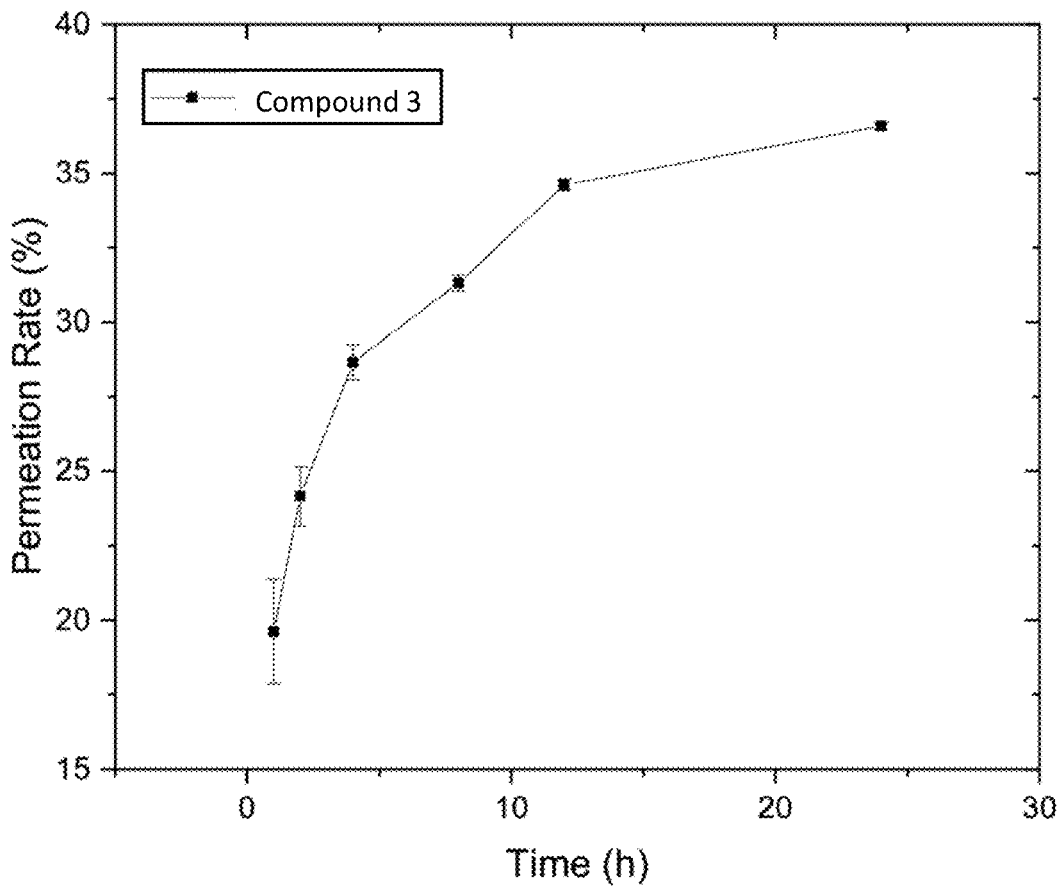
FIG. 4D illustrates skin permeation rate of Compound 3 for up to 24 hours.
Figure 5D:
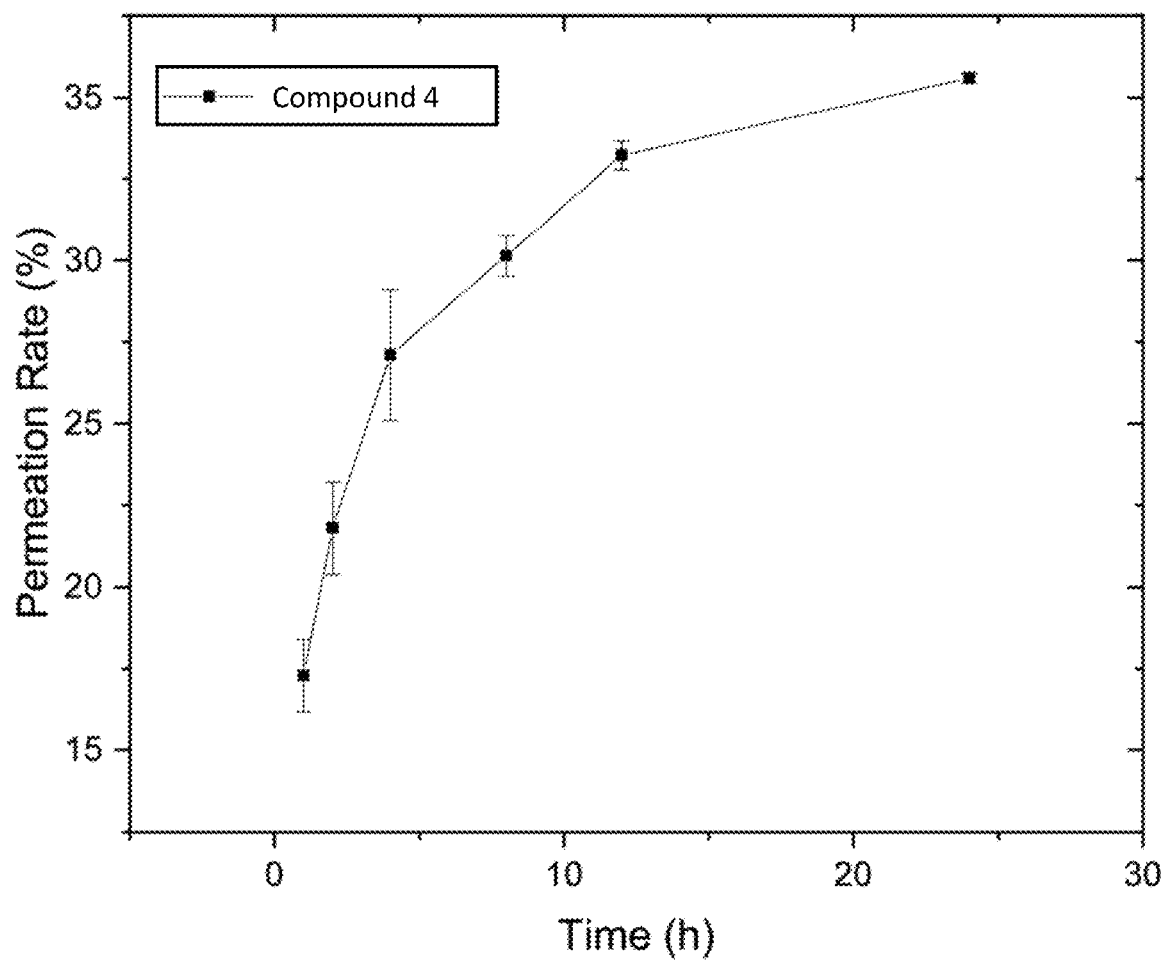
FIG. 5D illustrates skin permeation rate of Compound 4 for up to 24 hours.
Figure 6D:
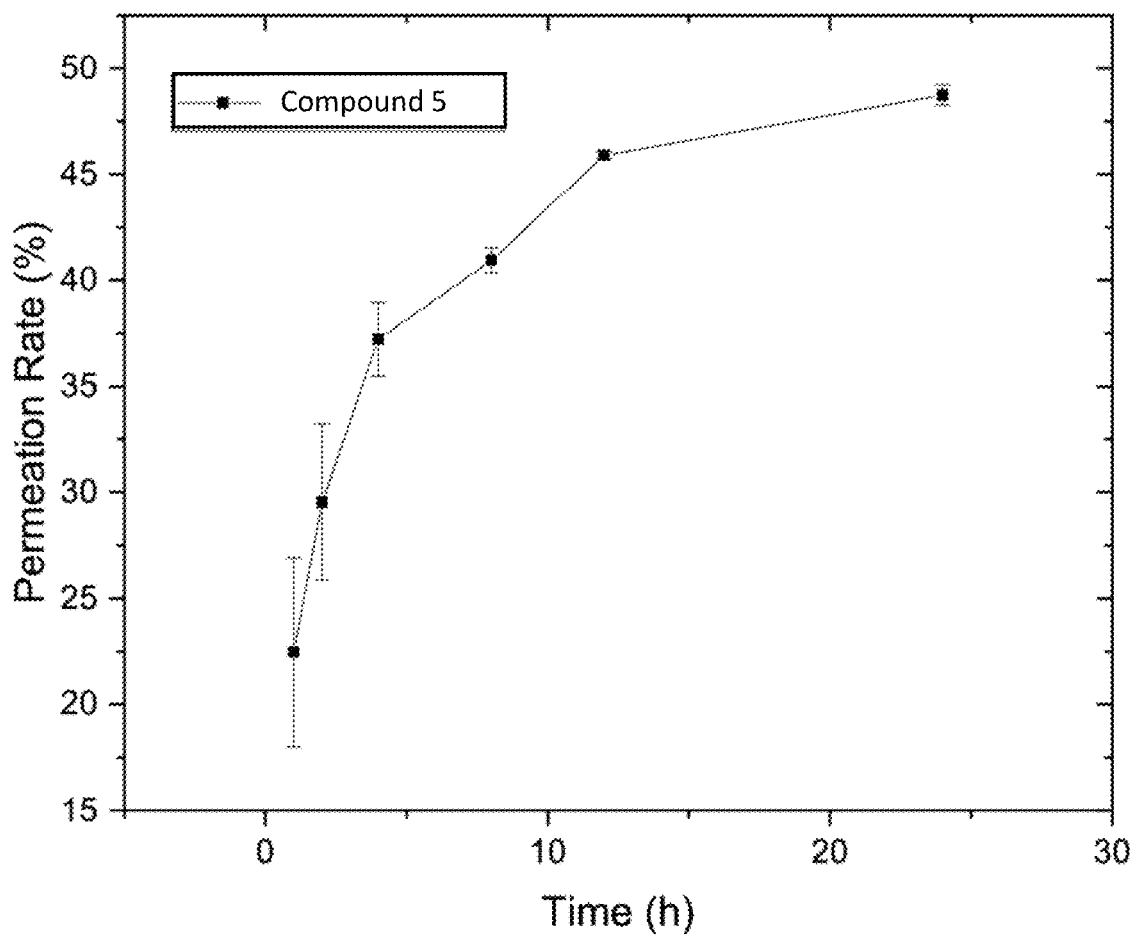
FIG. 6D illustrates skin permeation rate of Compound 5 for up to 24 hours.
Figure 7D:
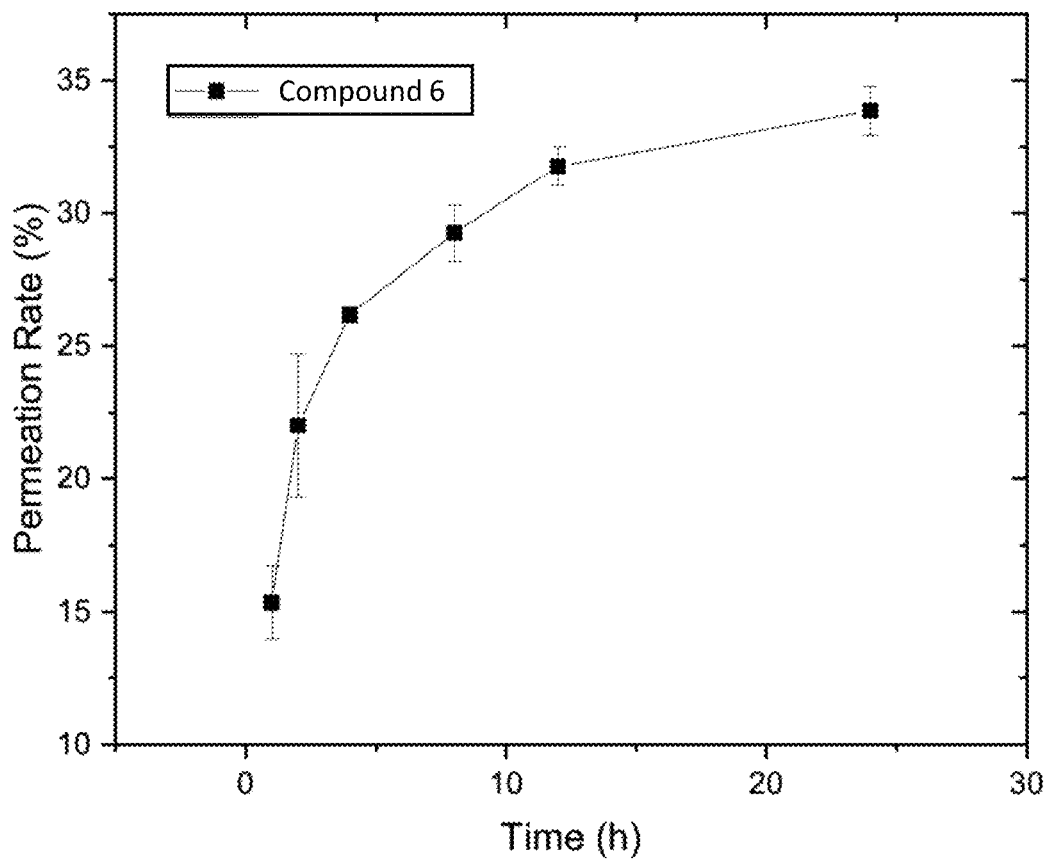
FIG. 7D illustrates skin permeation rate of Compound 6 for up to 24 hours.
Figure 8D:
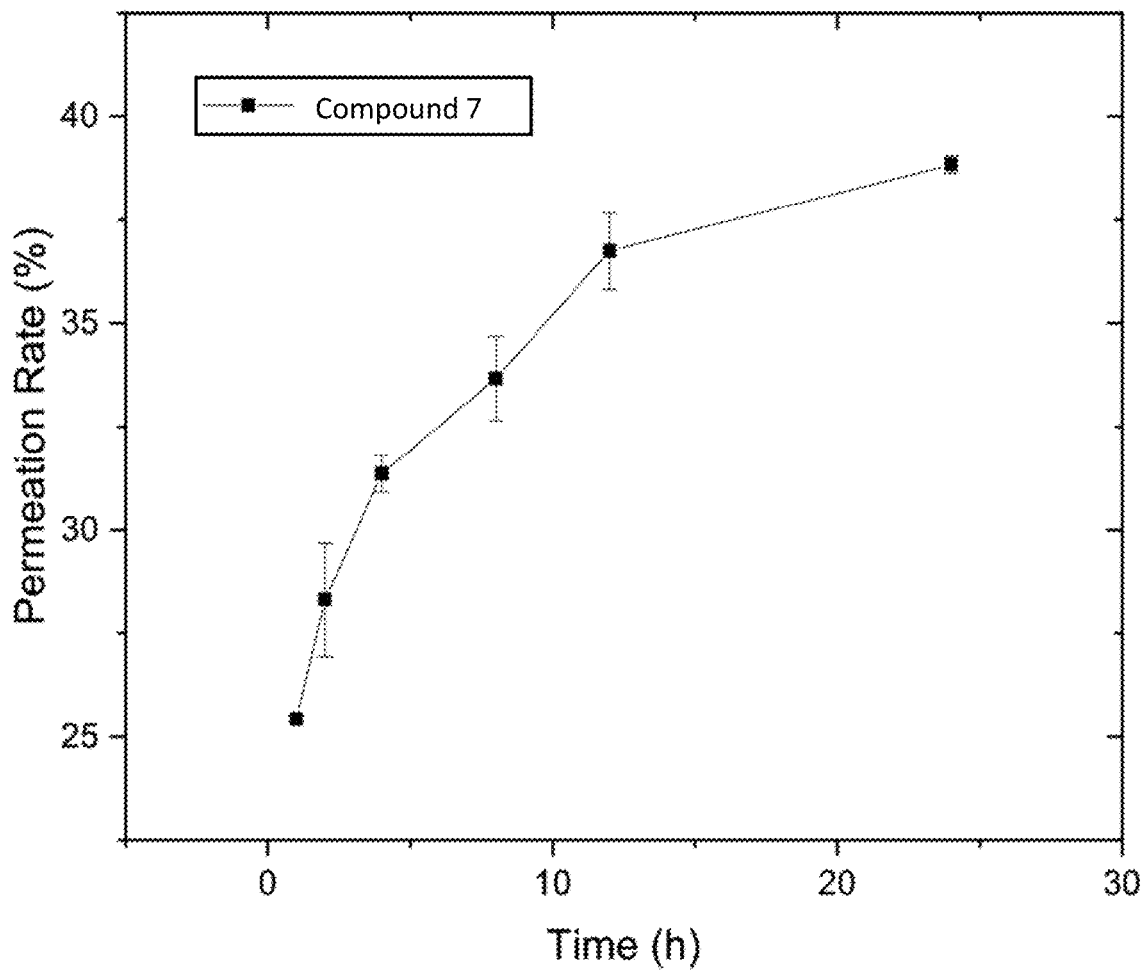
FIG. 8D illustrates skin permeation rate of Compound 7 for up to 24 hours.
Figure 9D:
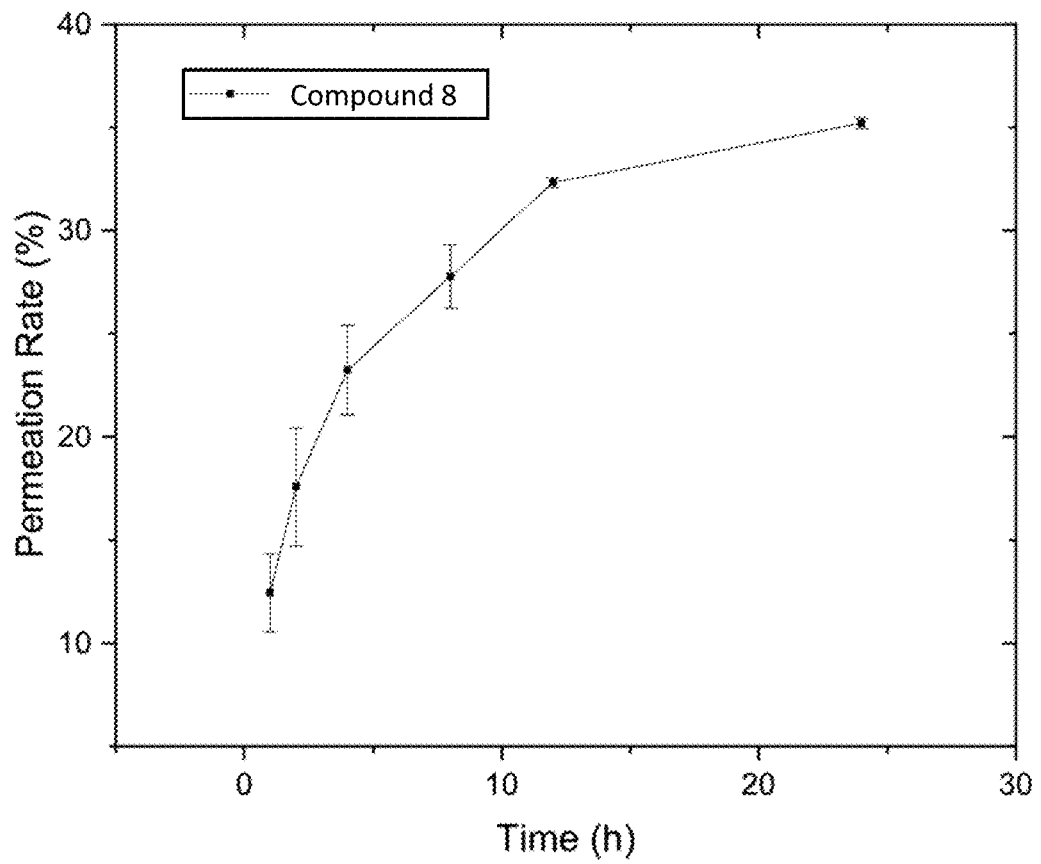
FIG. 9D illustrates skin permeation rate of Compound 8 for up to 24 hours.
Figure 10D:
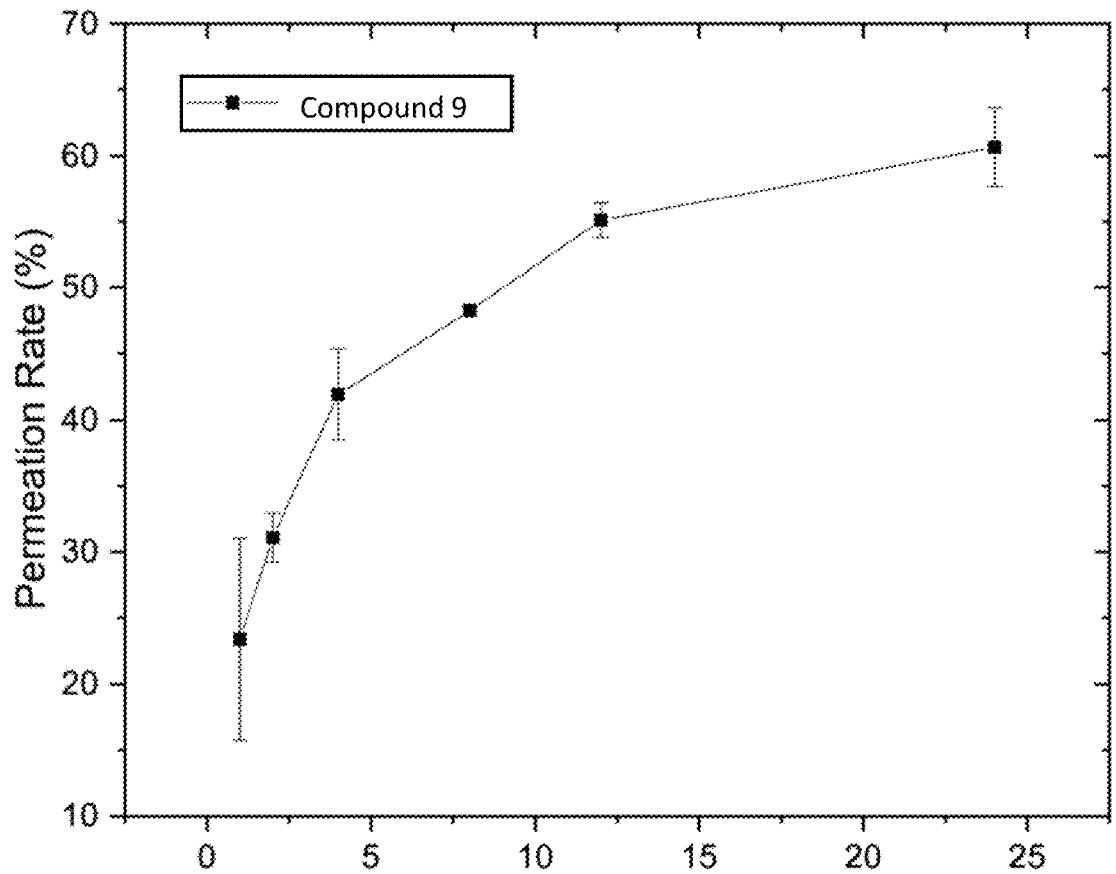
FIG. 10D illustrates skin permeation rate of Compound 9 for up to 24 hours.
Figure 11D:
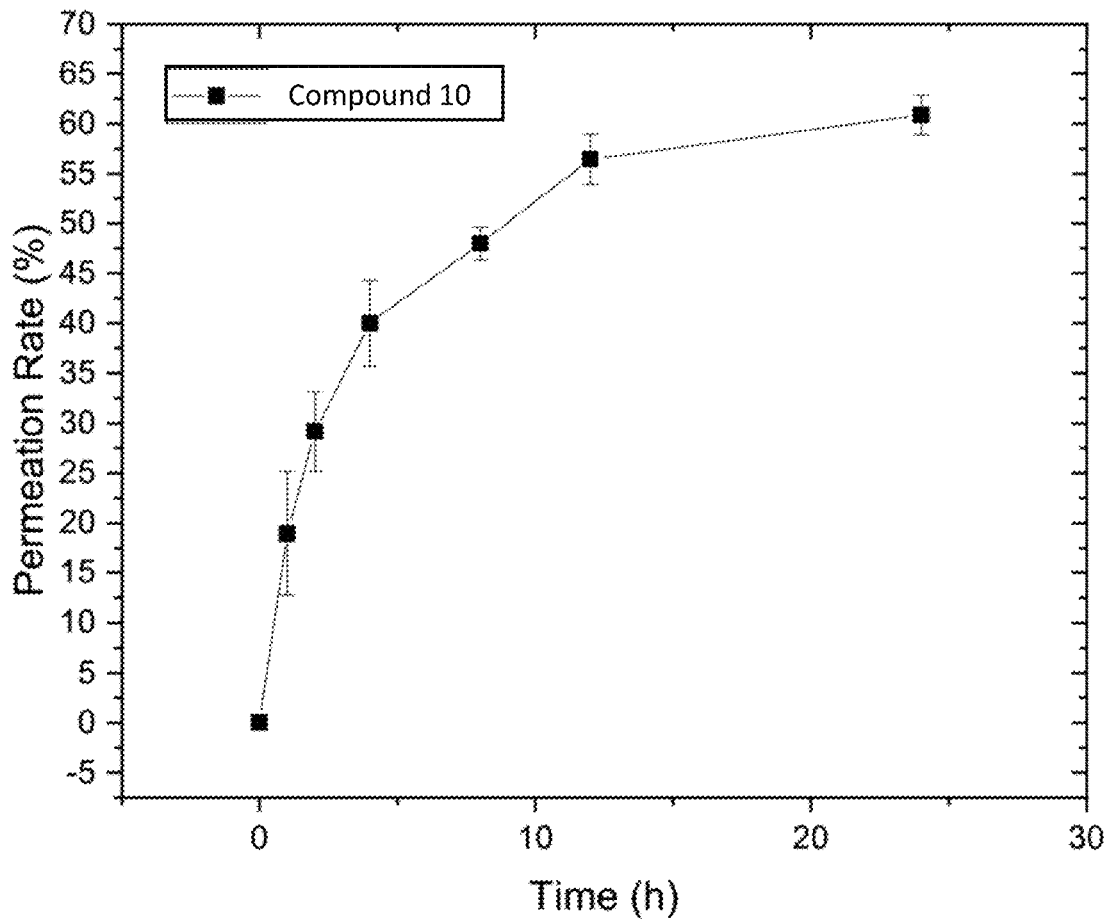
FIG. 11D illustrates skin permeation rate of Compound 10 for up to 24 hours.
Figure 12D:
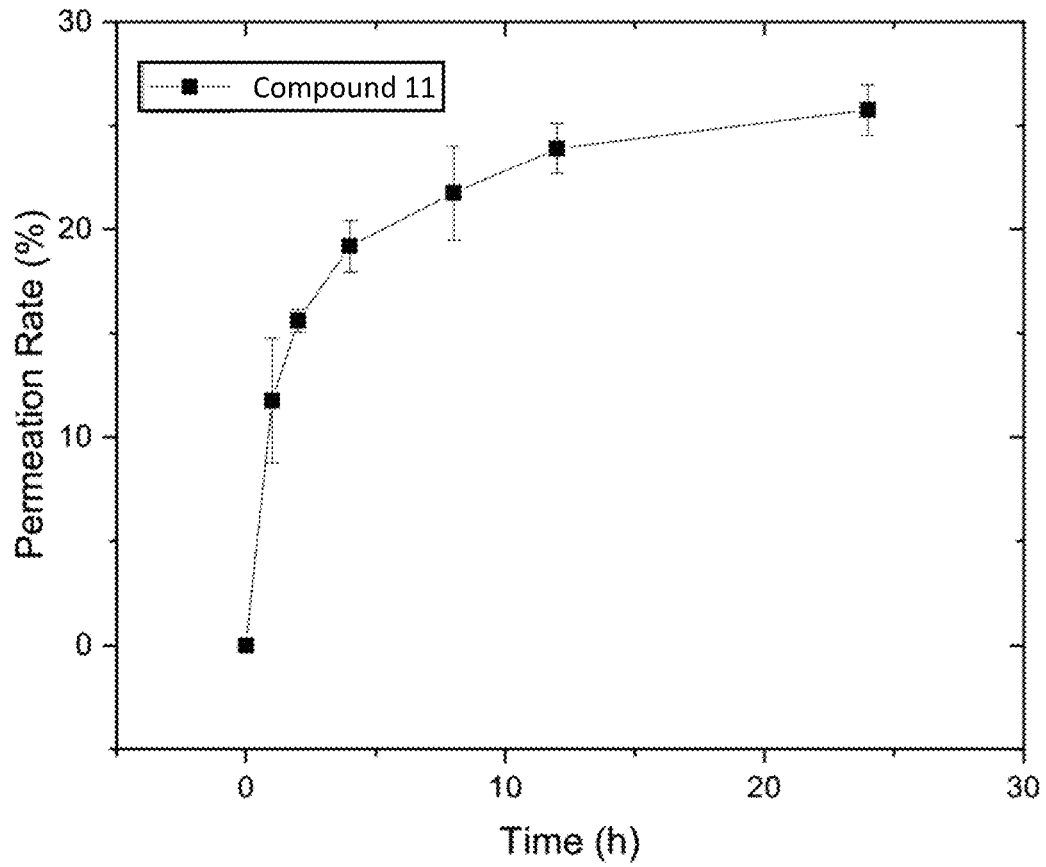
FIG. 12D illustrates skin permeation rate of Compound 11 for up to 24 hours.

10) The relationship between the permeation rate of each cyclic oligopeptide and time was calculated based on the average results of the triplicate experimental groups (illustrated by FIG. 2D, FIG. 3D, FIG. 4D, FIG. 5D, FIG. 6D, FIG. 7D, FIG. 8D, FIG. 9D, FIG. 10D, FIG. 11D and FIG. 12D).

All the cyclic oligopeptides had more than 25% average permeation rates after 24 hours. As shown in Table 3, Compound 9 and Compound 10 had more than 60% permeation rates after 24 hours. Compound 1 and Compound 5 had permeation rates between 40% and 50% after 24 hours. Compound 2, Compound 3, Compound 4, Compound 6, Compound 7, and Compound 8 had permeation rates between 30% and 40% after 24 hours. Compound 11 had permeation rate of about 26% after 24 hours. As shown in FIG. 2D, FIG. 3D, FIG. 4D, FIG. 5D, FIG. 6D, FIG. 7D, FIG. 8D, FIG. 9D, FIG. 10D, FIG. 11D and FIG. 12D, from 1 hour to 24 hours, the permeation rates of the oligopeptides increased steadily. These data demonstrated the relative high skin permeation efficiency of the cyclic oligopeptides of this disclosure throughout a relative long period of time.

In addition, as shown in Table 3 and FIG. 2D, FIG. 3D, FIG. 4D, FIG. 5D, FIG. 6D, FIG. 7D, FIG. 8D, FIG. 9D, FIG. 10D, FIG. 11D and FIG. 12D, all the cyclic oligopeptides had more than 10% average permeation rates after 1 hours. Compound 5, Compound 7 and Compound 9 had more than 20% permeation rates after 1 hour. Compound 1, Compound 3, Compound 4, Compound 6 and Compound 10 had permeation rates between 15% and 20% after 1 hour. Compound 2, Compound 8, and Compound 11 had permeation rates between 10% and 15% after 24 hours. These data demonstrated the fast-acting quality of the oligopeptides of this disclosure when applied topically, indicated by the relative high percentage of skin permeation rate within the first hour.

TABLE 3

Permeation rate of exemplary cyclic oligopeptides that bind to IL-13.

| Cyclic Oligopeptide | Average Permeation Rate After 1 Hour (%) | Average Permeation Rate After 24 Hours (%) |
|---|---|---|
| Compound 1 | 18.54 | 42.06 |
| Compound 2 | 14.62 | 30.51 |
| Compound 3 | 19.61 | 36.59 |
| Compound 4 | 17.28 | 35.59 |
| Compound 5 | 22.46 | 48.73 |
| Compound 6 | 15.34 | 33.86 |
| Compound 7 | 25.42 | 38.84 |
| Compound 8 | 12.44 | 35.20 |
| Compound 9 | 23.40 | 60.63 |
| Compound 10 | 18.96 | 60.88 |
| Compound 11 | 11.77 | 25.75 |

The skin permeability coefficient (Kp)(cm/hr) values for the cyclic oligopeptides were also calculated with the following equation:

$$\text{permeability coefficient } (Kp) = \frac{Q}{AT\Delta C};$$

wherein Q(mg) refers to the total amount of cyclic oligopeptide that pass through the artificial skin within a certain amount of time; A(cm$^2$) refers to the internal cross-section area of the artificial skin in a diffusion cell; T(hr) refers to the total amount of time of cyclic oligopeptide permeation; and AC(mg/mL) refers to the concentration difference of the cyclic oligopeptide between the two sides of the artificial skin.

Figure 2E:
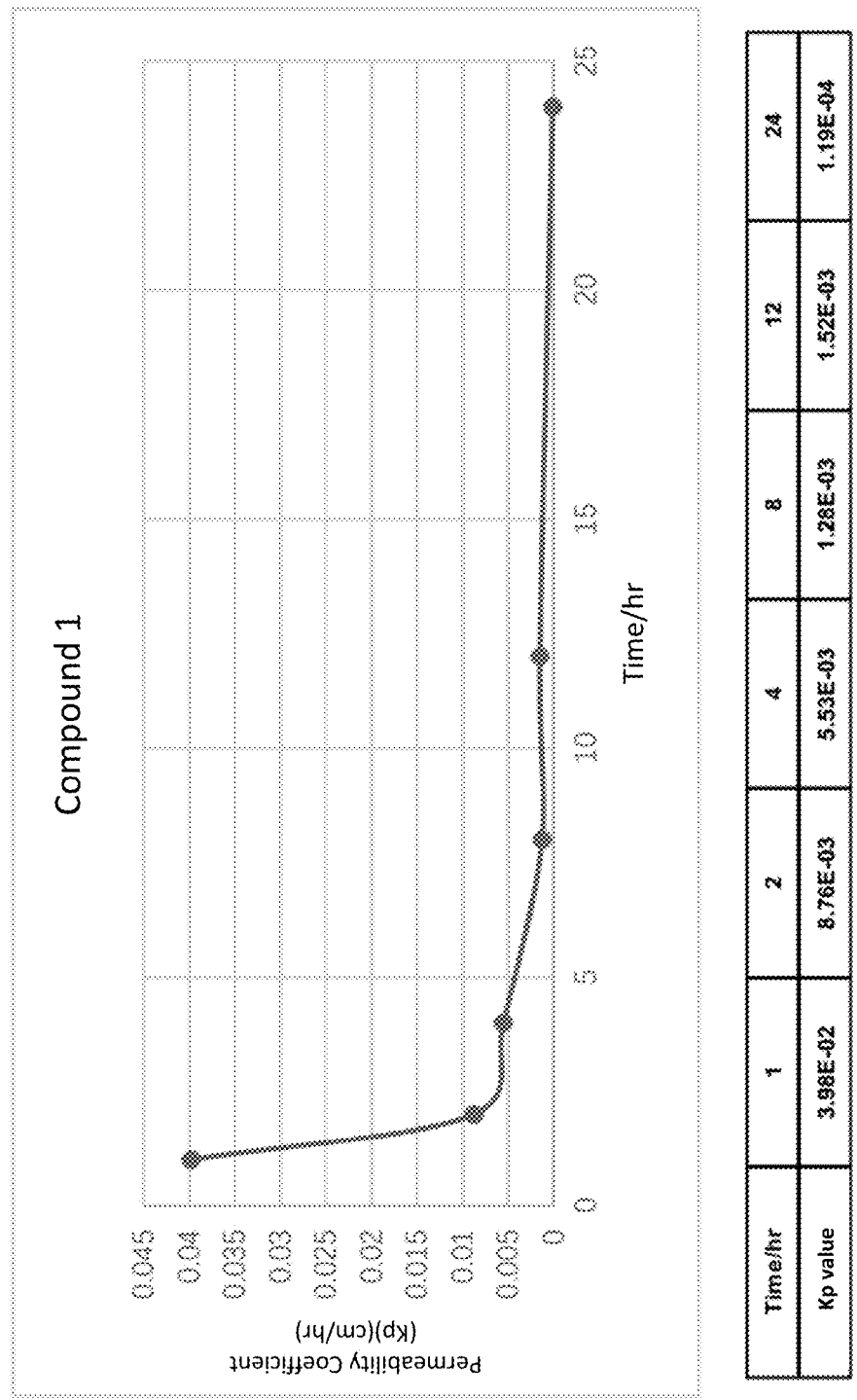
FIG. 2E illustrates average permeability coefficient (Kp) of Compound 1 for 1, 2, 4, 8, 12 and 24 hours.
Figure 3E:
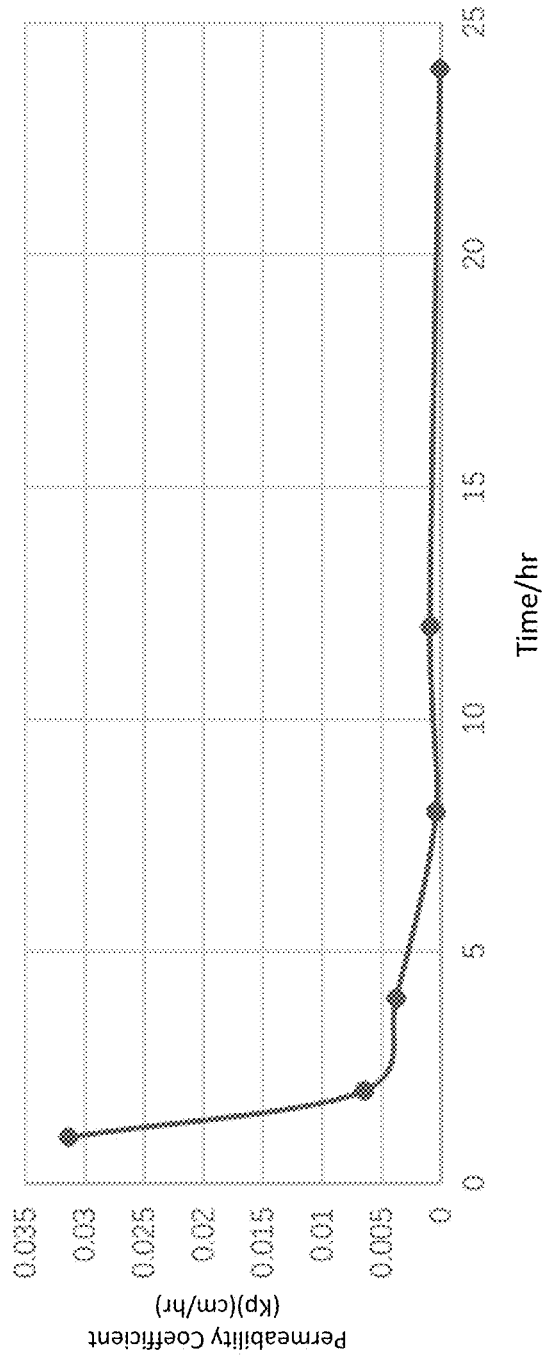
FIG. 3E illustrates average permeability coefficient (Kp) of Compound 2 for 1, 2, 4, 8, 12 and 24 hours.
Figure 4E:
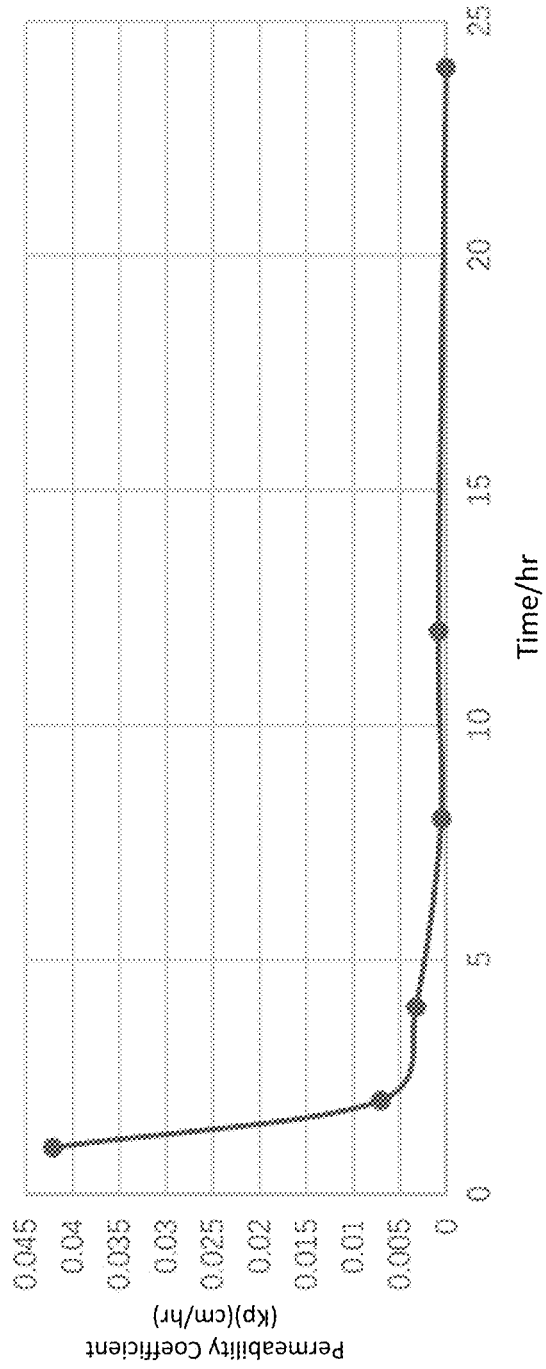
FIG. 4E illustrates average permeability coefficient (Kp) of Compound 3 for 1, 2, 4, 8, 12 and 24 hours.
Figure 5E:
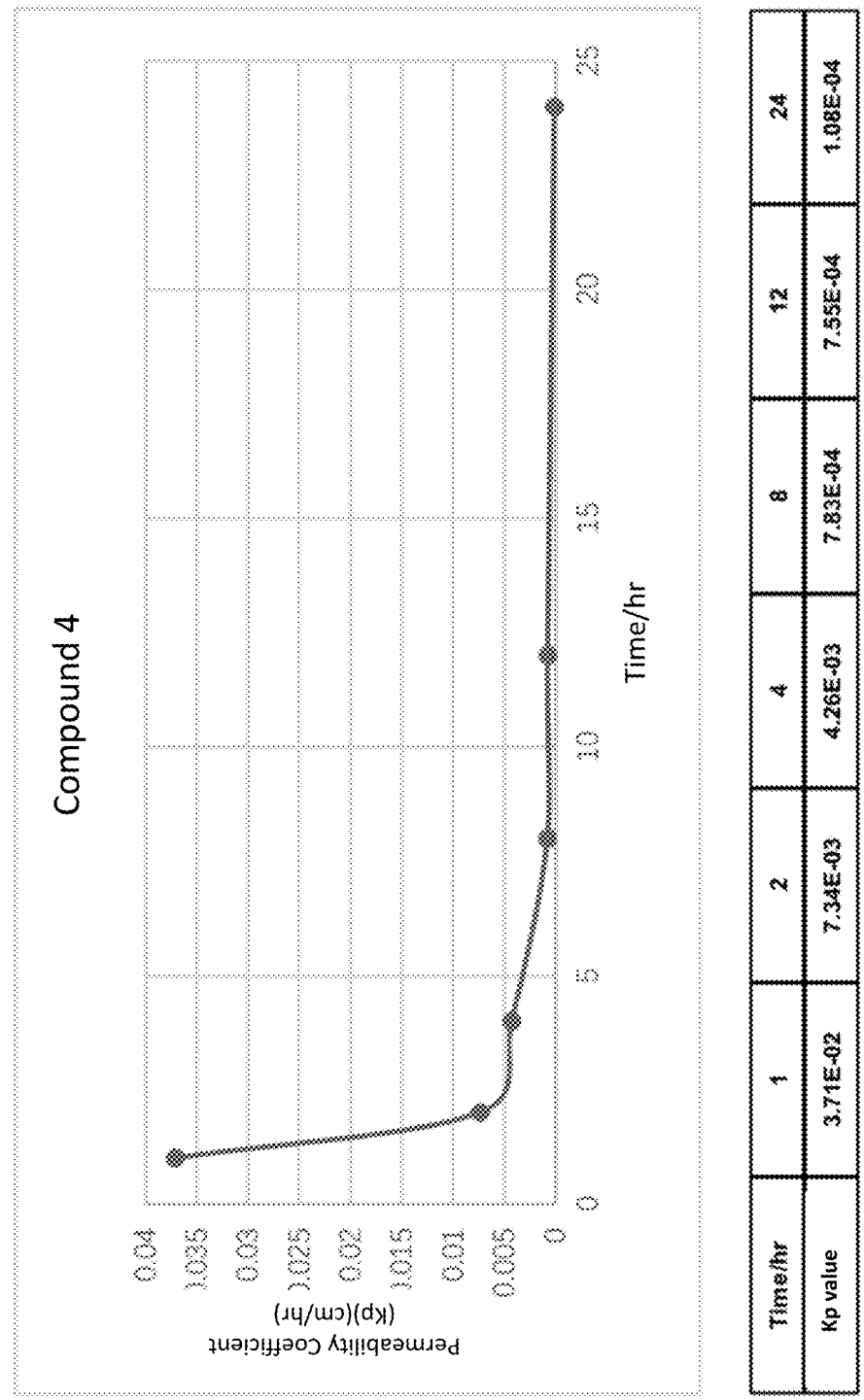
FIG. 5E illustrates average permeability coefficient (Kp) of Compound 4 for 1, 2, 4, 8, 12 and 24 hours.
Figure 6E:
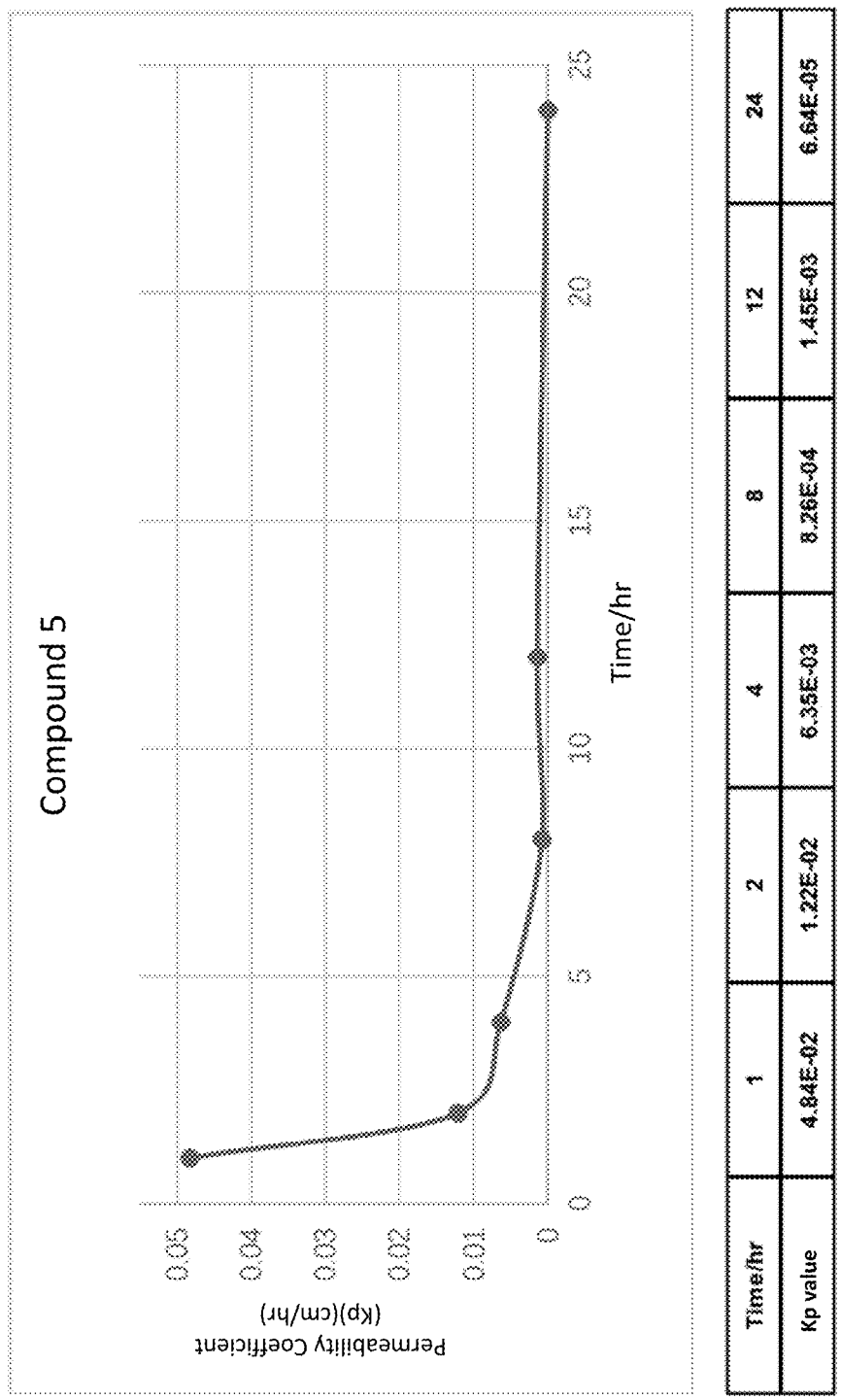
FIG. 6E illustrates average permeability coefficient (Kp) of Compound 5 for 1, 2, 4, 8, 12 and 24 hours.
Figure 7E:
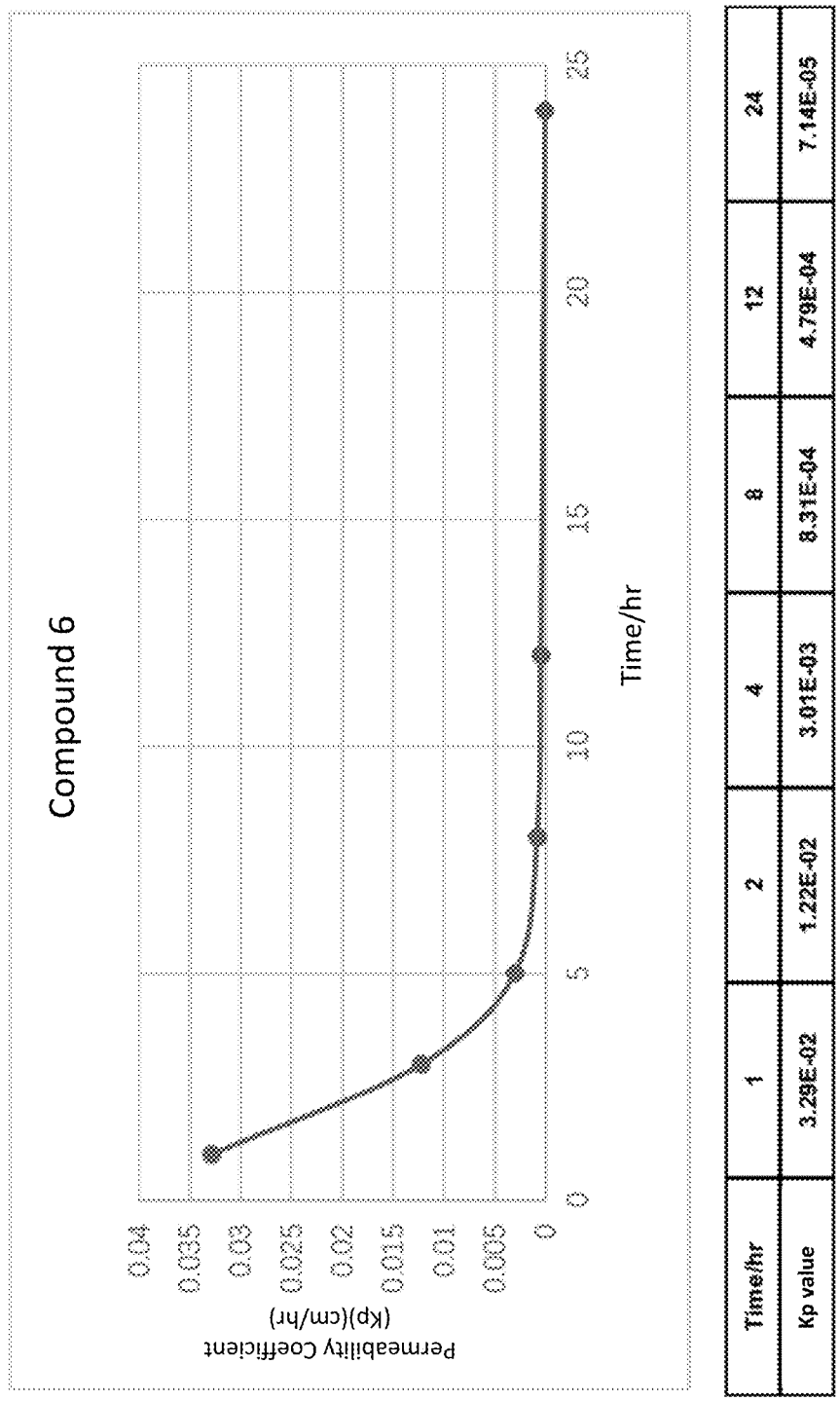
FIG. 7E illustrates average permeability coefficient (Kp) of Compound 6 for 1, 2, 4, 8, 12 and 24 hours.
Figure 8E:
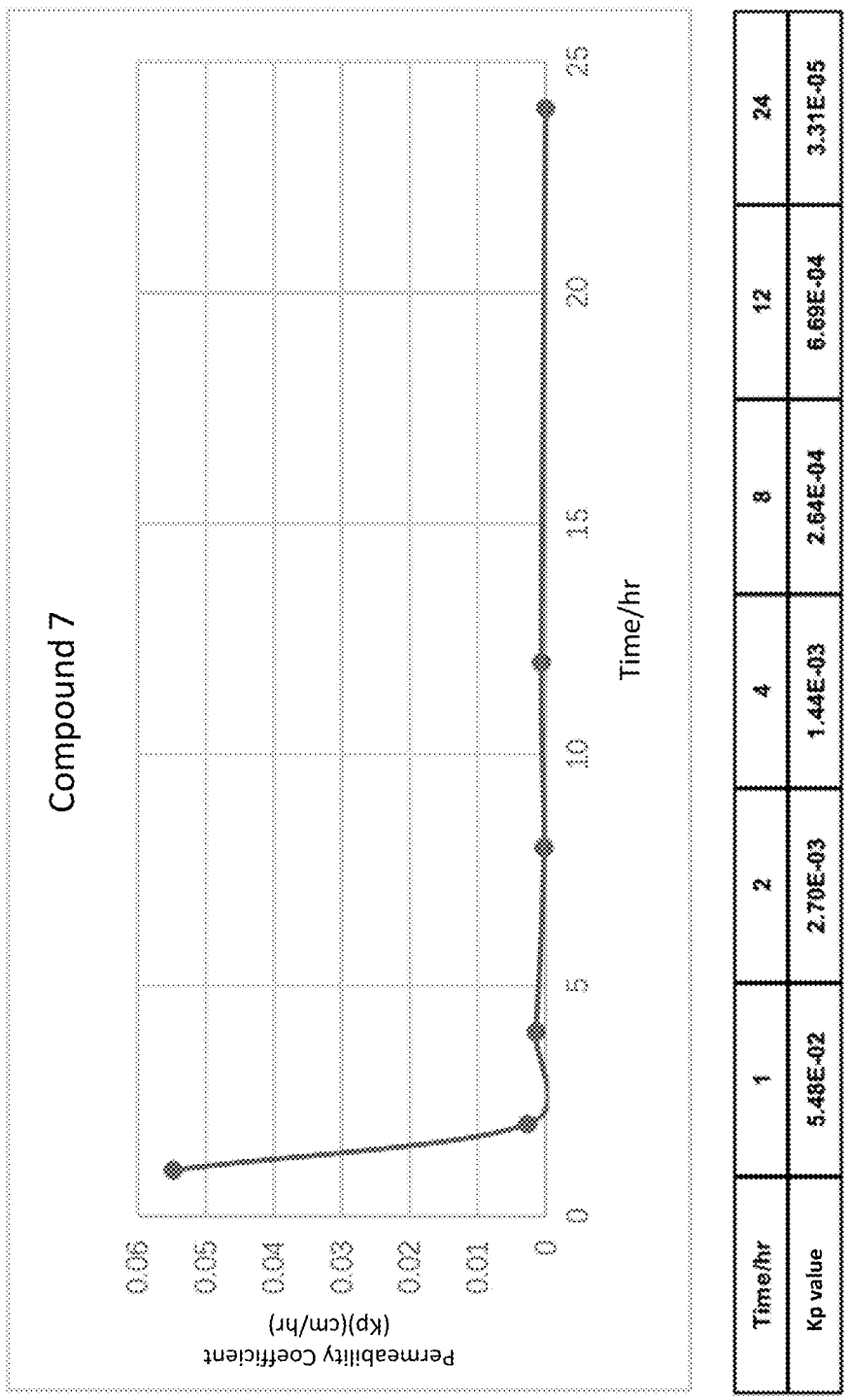
FIG. 8E illustrates average permeability coefficient (Kp) of Compound 7 for 1, 2, 4, 8, 12 and 24 hours.
Figure 9E:
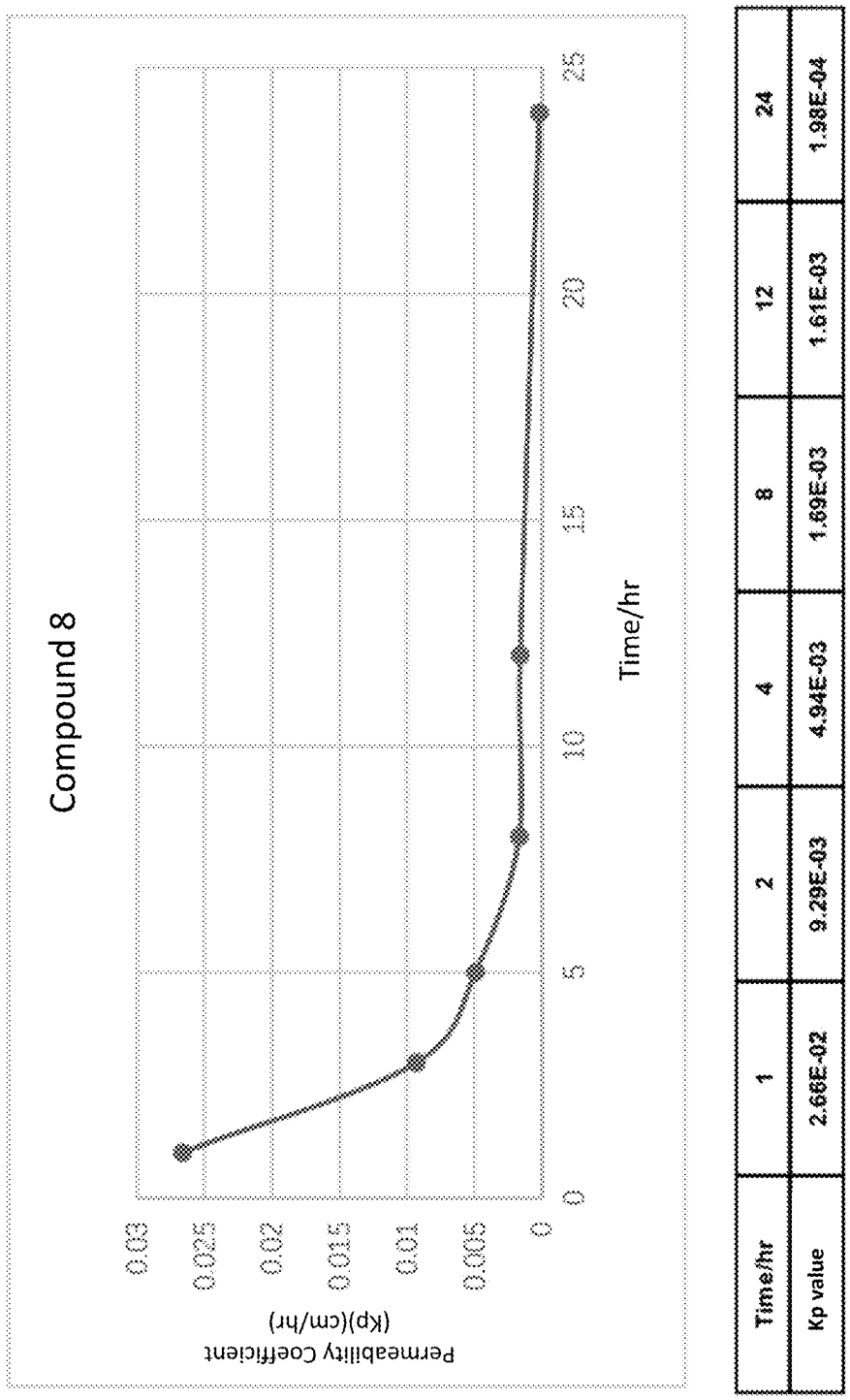
FIG. 9E illustrates average permeability coefficient (Kp) of Compound 8 for 1, 2, 4, 8, 12 and 24 hours.
Figure 11E:
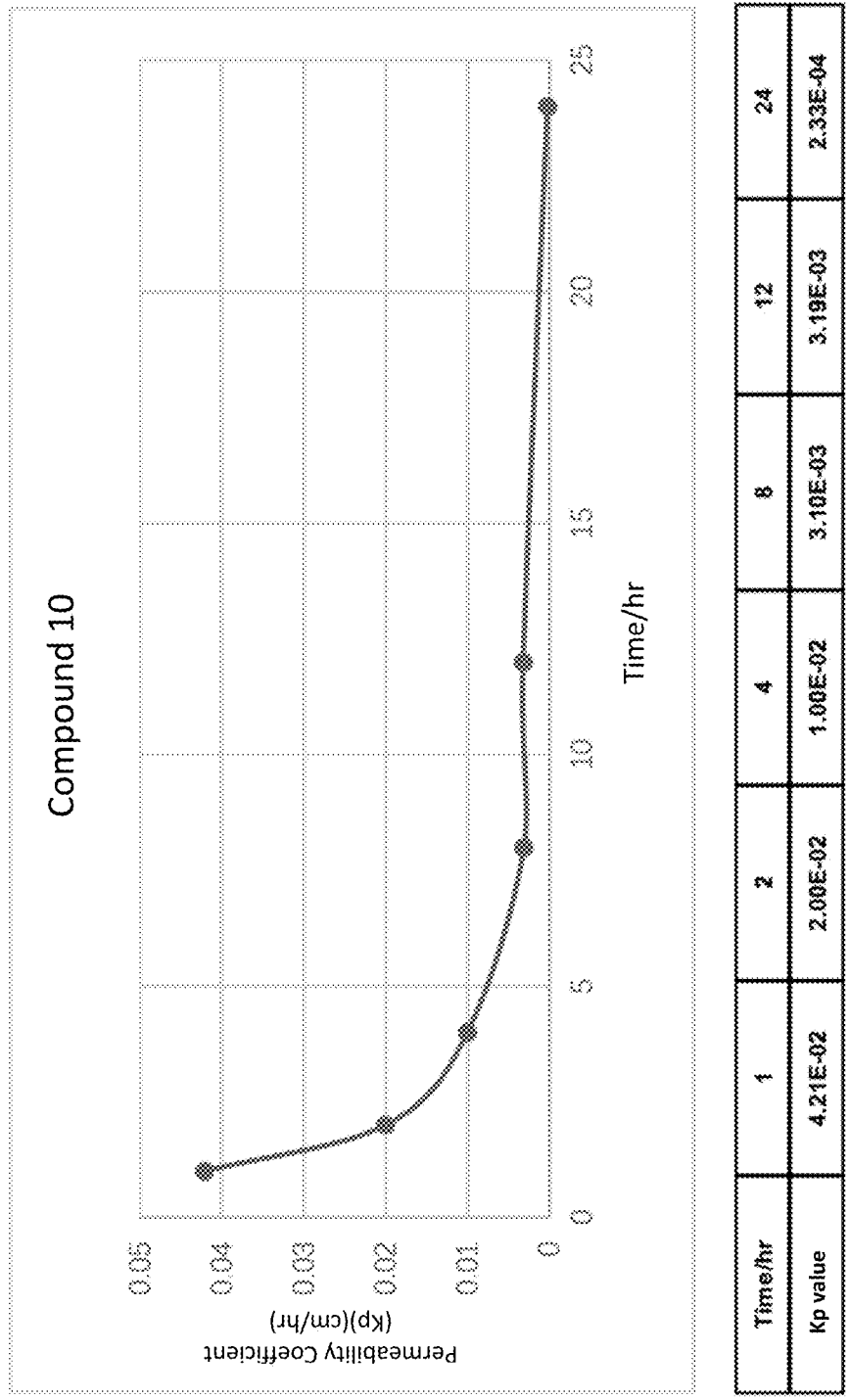
FIG. 11E illustrates average permeability coefficient (Kp) of Compound 10 for 1, 2, 4, 8, 12 and 24 hours.

As shown in Table 4 and illustrated by FIG. 2E, FIG. 3E, FIG. 4E, FIG. 5E, FIG. 6E, FIG. 7E, FIG. 8E, FIG. 9E, FIG. 10E, FIG. 11E and FIG. 12E, all the cyclic oligopeptides had more than 2×10$^{-5}$ average Kp values after 24 hours. Compound 1, Compound 4, Compound 8, Compound 9 and Compound 10 had average Kp values higher than 1×10$^{-4}$ cm/hr after 24 hours. Compound 2, Compound 3, Compound 5, Compound 6, Compound 7 and Compound 11 had average Kp values between 1×10$^{-5}$ cm/hr and 1×10$^{-4}$ cm/hr after 24 hours. These data also demonstrated that the cyclic oligopeptides of this disclosure were able to penetrate skin throughout a relative long period of time.

In addition, as also shown in Table 4 and illustrated by FIG. 2E, FIG. 3E, FIG. 4E, FIG. 5E, FIG. 6E, FIG. 7E, FIG. 8E, FIG. 9E, FIG. 10E, FIG. 11E and FIG. 12E, all the cyclic oligopeptides had more than 2×10$^{-2}$ cm/hr average Kp values within the first hour, indicating that the cyclic oligopeptides of this disclosure were fast-acting after being topically applied to skin.

TABLE 4

Average permeability coefficient (Kp) of exemplary cyclic oligopeptides that bind to IL-13.

| Cyclic Oligopeptide | Average Permeability Coefficient (Kp) After 1 hour (cm/hr) | Average Permeability Coefficient (Kp) After 24 hours (cm/hr) |
| --- | --- | --- |
| Compound 1  | 3.98 × 10$^{-2}$ | 1.19 × 10$^{-4}$ |
| Compound 2  | 3.13 × 10$^{-2}$ | 8.74 × 10$^{-5}$ |
| Compound 3  | 4.22 × 10$^{-2}$ | 2.55 × 10$^{-5}$ |
| Compound 4  | 3.71 × 10$^{-2}$ | 1.08 × 10$^{-4}$ |
| Compound 5  | 4.84 × 10$^{-2}$ | 6.64 × 10$^{-5}$ |
| Compound 6  | 3.29 × 10$^{-2}$ | 7.14 × 10$^{-5}$ |
| Compound 7  | 5.48 × 10$^{-2}$ | 3.31 × 10$^{-5}$ |
| Compound 8  | 2.66 × 10$^{-2}$ | 1.98 × 10$^{-4}$ |
| Compound 9  | 5.04 × 10$^{-2}$ | 4.63 × 10$^{-4}$ |
| Compound 10 | 4.21 × 10$^{-2}$ | 2.33 × 10$^{-4}$ |
| Compound 11 | 2.60 × 10$^{-2}$ | 9.89 × 10$^{-5}$ |

SEQUENCE LISTING

```
Sequence total quantity: 11
SEQ ID NO: 1            moltype = AA  length = 6
FEATURE                 Location/Qualifiers
source                  1..6
                        mol_type = protein
                        organism = synthetic construct
SITE                    1
                        note = D-arginine
SITE                    2
                        note = D-phenylalanine
SITE                    3
                        note = D-valine
REGION                  1..6
                        note = circular peptide
SEQUENCE: 1
RFVYEP                                                                  6

SEQ ID NO: 2            moltype = AA  length = 6
FEATURE                 Location/Qualifiers
source                  1..6
                        mol_type = protein
                        organism = synthetic construct
SITE                    3
                        note = D-valine
SITE                    5
                        note = D-phenylalanine
SITE                    6
                        note = D-proline
REGION                  1..6
                        note = circular peptide
SEQUENCE: 2
RTVEFP                                                                  6

SEQ ID NO: 3            moltype = AA  length = 6
FEATURE                 Location/Qualifiers
source                  1..6
                        mol_type = protein
                        organism = synthetic construct
SITE                    2
                        note = D-threonine
SITE                    3
                        note = D-valine
SITE                    5
                        note = D-proline
SITE                    6
                        note = D-proline
REGION                  1..6
                        note = circular peptide
```

```
SEQUENCE: 3
ETVWPP                                                                                  6

SEQ ID NO: 4           moltype = AA  length = 6
FEATURE                Location/Qualifiers
source                 1..6
                       mol_type = protein
                       organism = synthetic construct
SITE                   3
                       note = D-valine
SITE                   5
                       note = D-proline
SITE                   6
                       note = D-proline
REGION                 1..6
                       note = circular peptide
SEQUENCE: 4
REVWPP                                                                                  6

SEQ ID NO: 5           moltype = AA  length = 6
FEATURE                Location/Qualifiers
source                 1..6
                       mol_type = protein
                       organism = synthetic construct
SITE                   5
                       note = D-proline
SITE                   6
                       note = D-proline
REGION                 1..6
                       note = circular peptide
SEQUENCE: 5
WVREPP                                                                                  6

SEQ ID NO: 6           moltype = AA  length = 6
FEATURE                Location/Qualifiers
source                 1..6
                       mol_type = protein
                       organism = synthetic construct
SITE                   4
                       note = D-threonine
SITE                   5
                       note = D-valine
SITE                   6
                       note = D-proline
REGION                 1..6
                       note = circular peptide
SEQUENCE: 6
YRETVP                                                                                  6

SEQ ID NO: 7           moltype = AA  length = 6
FEATURE                Location/Qualifiers
source                 1..6
                       mol_type = protein
                       organism = synthetic construct
SITE                   3
                       note = D-phenylalanine
SITE                   5
                       note = D-leucine
SITE                   6
                       note = D-proline
REGION                 1..6
                       note = circular peptide
SEQUENCE: 7
TRFPLP                                                                                  6

SEQ ID NO: 8           moltype = AA  length = 7
FEATURE                Location/Qualifiers
source                 1..7
                       mol_type = protein
                       organism = synthetic construct
SITE                   1
                       note = D-leucine
REGION                 1..7
                       note = circular peptide
SEQUENCE: 8
LREPWMP                                                                                 7

SEQ ID NO: 9           moltype = AA  length = 7
FEATURE                Location/Qualifiers
```

| | | |
|---|---|---|
| source | 1..7 | |
| | mol_type = protein | |
| | organism = synthetic construct | |
| SITE | 1 | |
| | note = D-arginine | |
| SITE | 3 | |
| | note = D-tryptophan | |
| SITE | 5 | |
| | note = D-threonine | |
| REGION | 1..7 | |
| | note = circular peptide | |
| SEQUENCE: 9 | | |
| RLWWTEP | | 7 |
| | | |
| SEQ ID NO: 10 | moltype = AA  length = 7 | |
| FEATURE | Location/Qualifiers | |
| source | 1..7 | |
| | mol_type = protein | |
| | organism = synthetic construct | |
| SITE | 5 | |
| | note = D-proline | |
| SITE | 6 | |
| | note = D-tryptophan | |
| SITE | 7 | |
| | note = D-proline | |
| REGION | 1..7 | |
| | note = circular peptide | |
| SEQUENCE: 10 | | |
| RDYCPWP | | 7 |
| | | |
| SEQ ID NO: 11 | moltype = AA  length = 8 | |
| FEATURE | Location/Qualifiers | |
| source | 1..8 | |
| | mol_type = protein | |
| | organism = synthetic construct | |
| SITE | 3 | |
| | note = D-leucine | |
| SITE | 4 | |
| | note = D-tryptophan | |
| SITE | 5 | |
| | note = D-valine | |
| REGION | 1..8 | |
| | note = circular peptide | |
| SEQUENCE: 11 | | |
| VPLWVLRP | | 8 |

We claim:
1. A cyclic oligopeptide, wherein the cyclic oligopeptide is selected from the group consisting of any one of Compounds 1-11
(Compound 1)
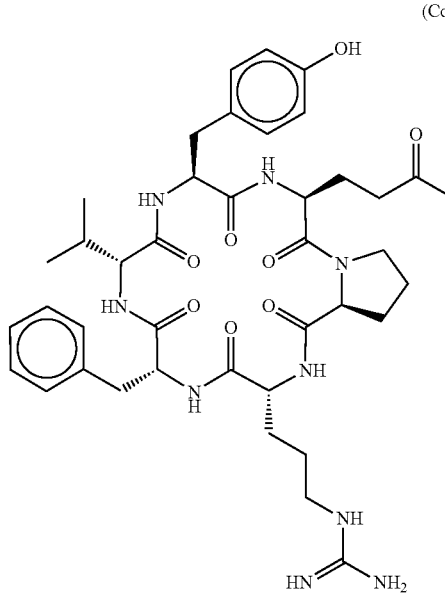
(Compound 2)
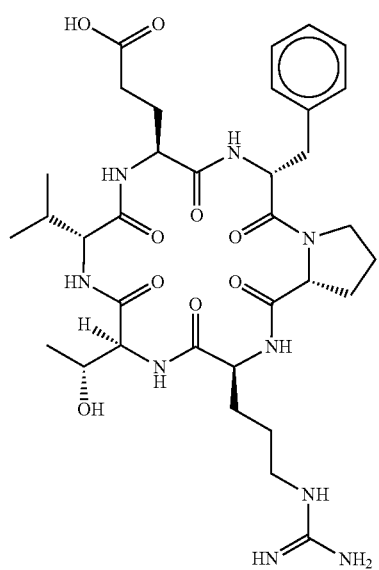
(Compound 3)
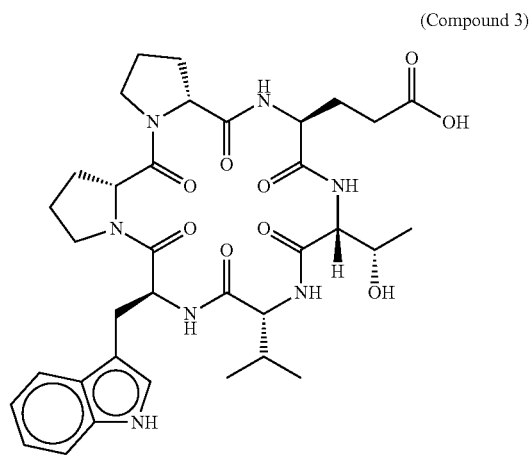
(Compound 4)
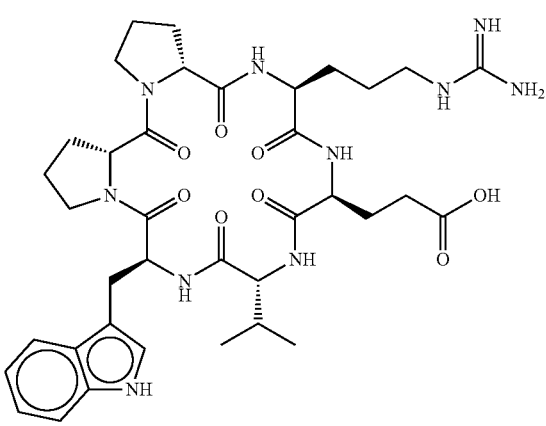
(Compound 5)
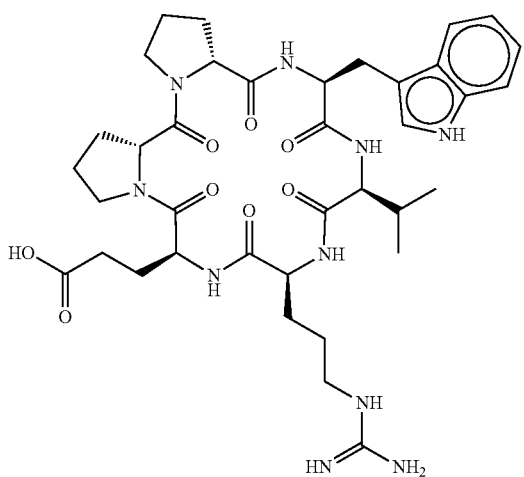

(Compound 6)
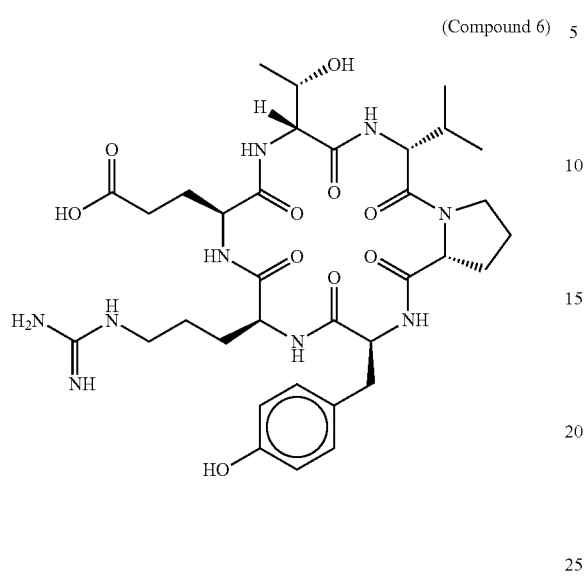
(Compound 8)
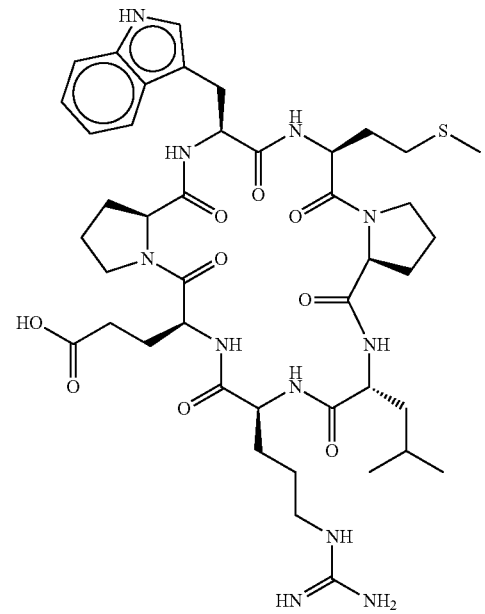
(Compound 7)
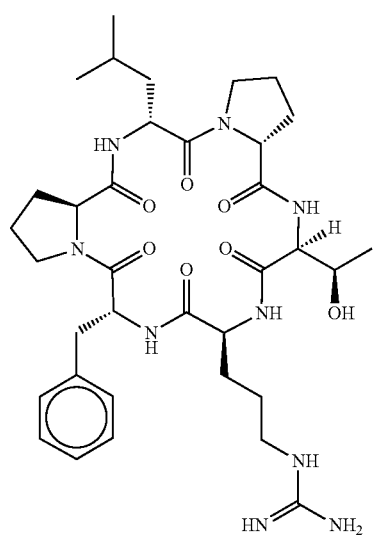
(Compound 9)
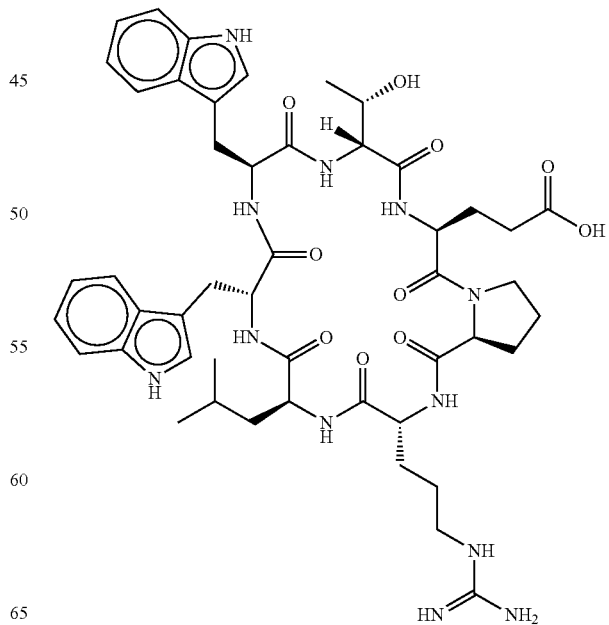

(Compound 10)
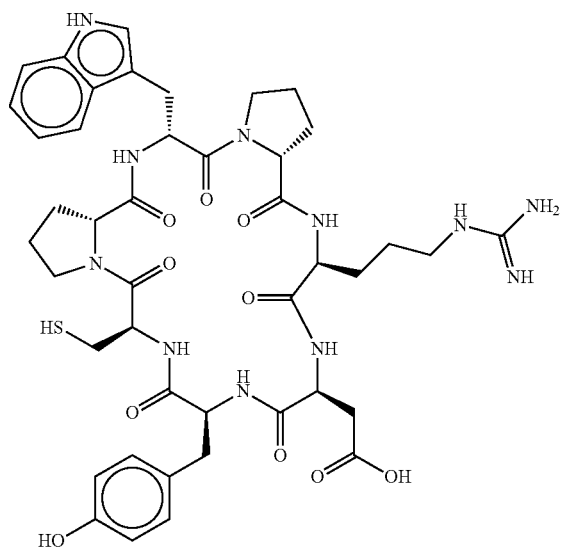
and
(Compound 11)
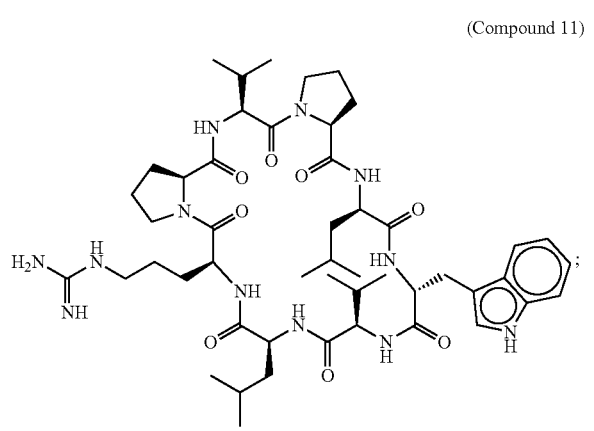
or a pharmaceutically acceptable salt of any of the foregoing.
2. The cyclic oligopeptide of claim 1, wherein the cyclic oligopeptide has is selected from the group consisting of any one of Compounds 1-11
(Compound 1)
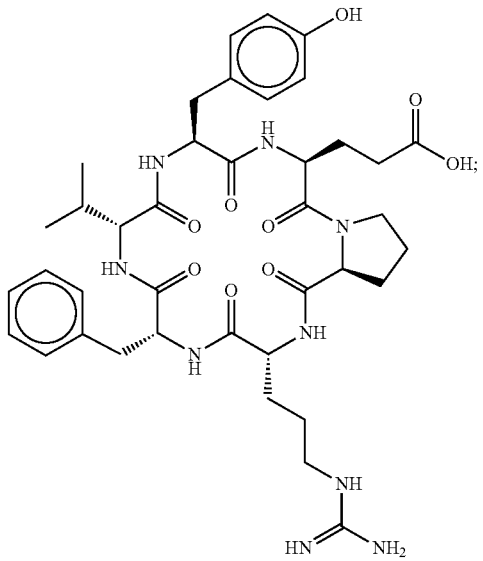
(Compound 2)
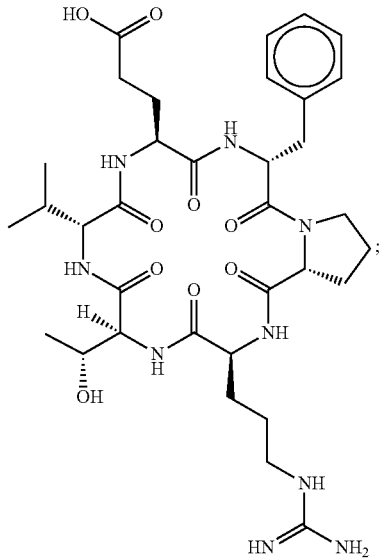

(Compound 3)
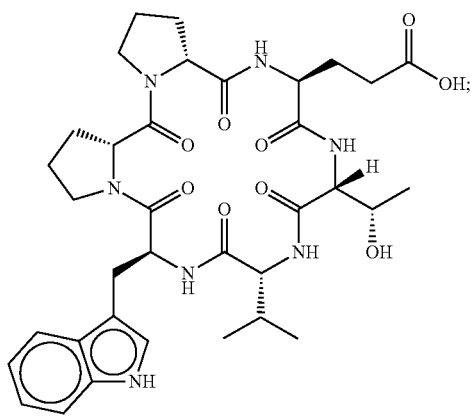
(Compound 4)
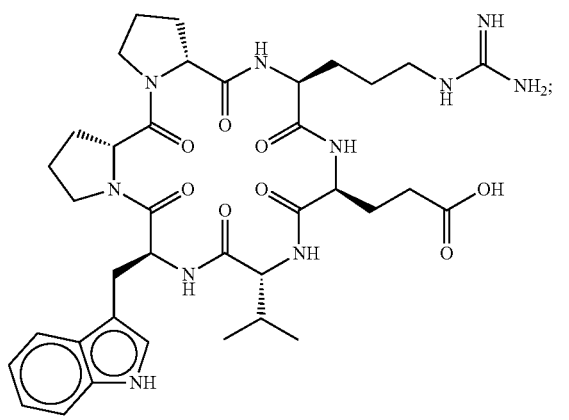
(Compound 5)
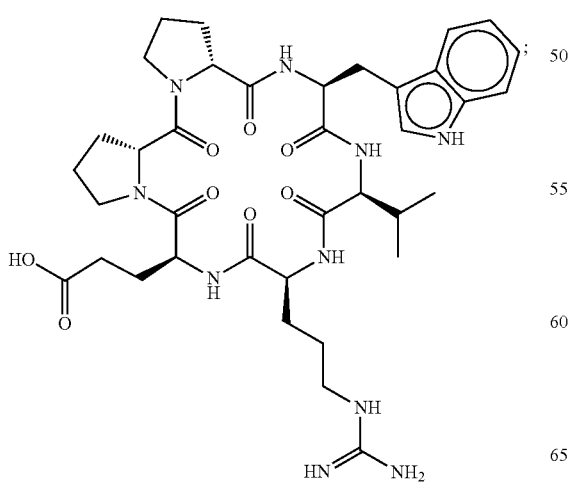
(Compound 6)
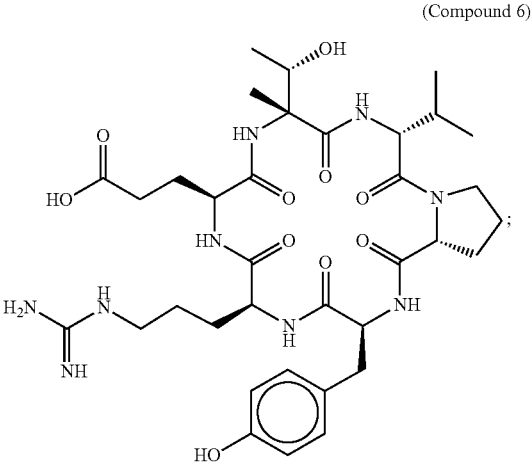
(Compound 7)
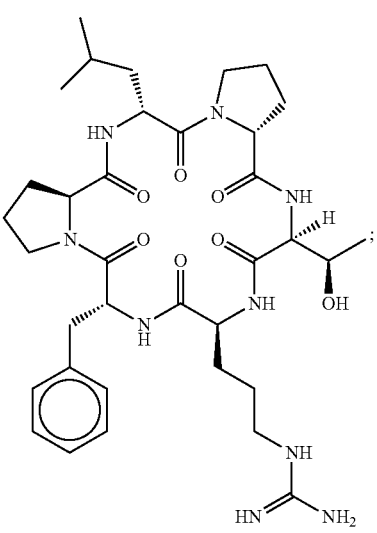

(Compound 8)
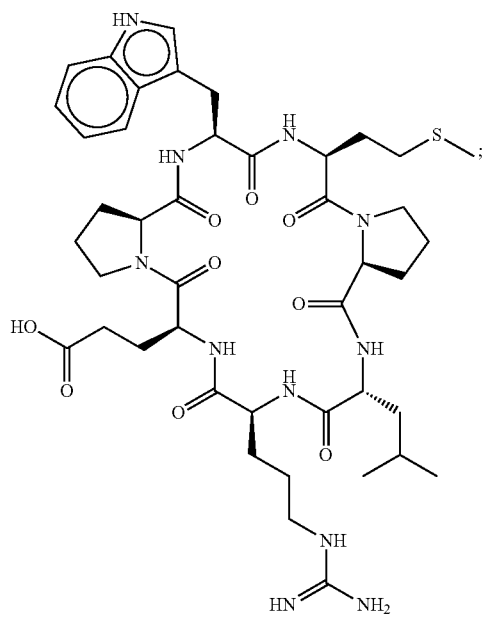
(Compound 10)
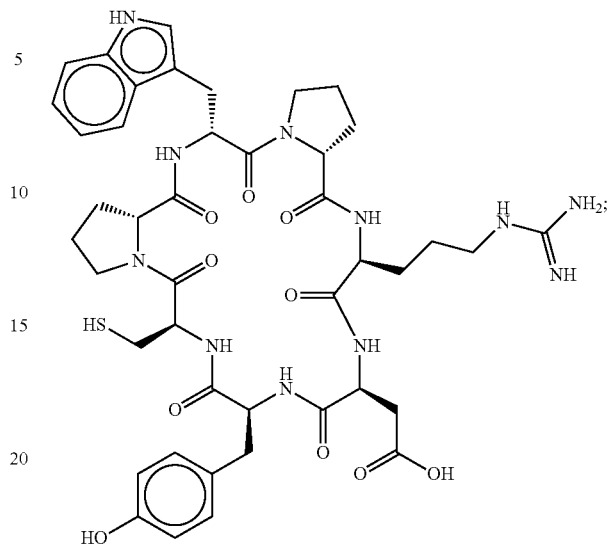
and
(Compound 9)
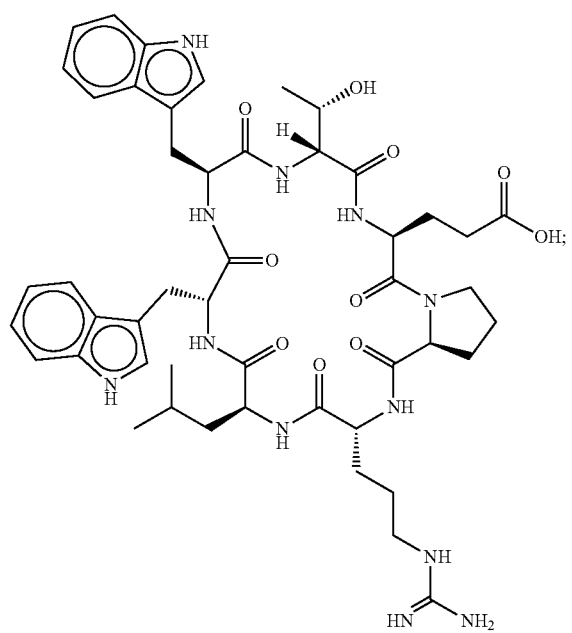
(Compound 11)
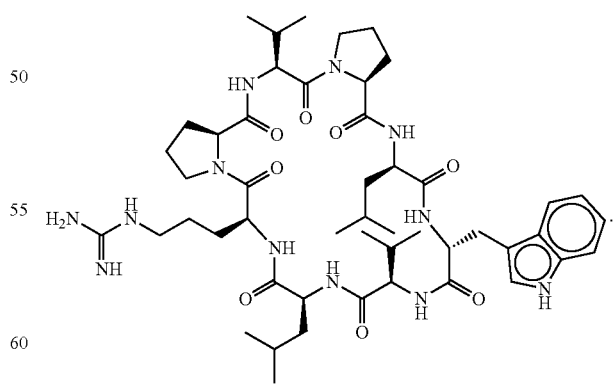
3. A pharmaceutical composition comprising a cyclic oligopeptide and a pharmaceutically acceptable carrier, wherein the cyclic oligopeptide is selected from the group consisting of any one of Compounds 1-11

(Compound 1)
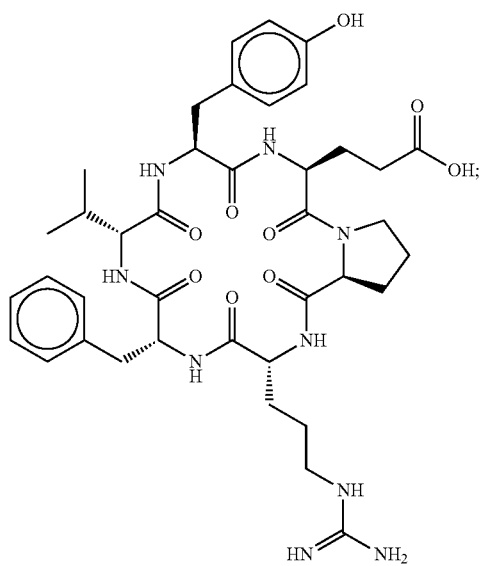
(Compound 4)
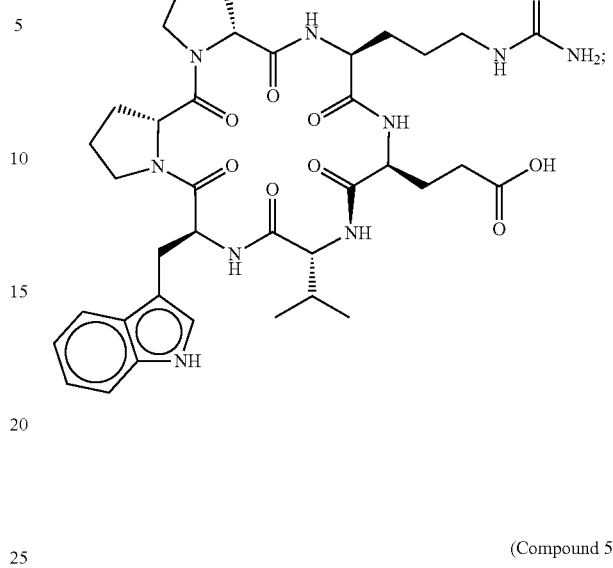
(Compound 2)
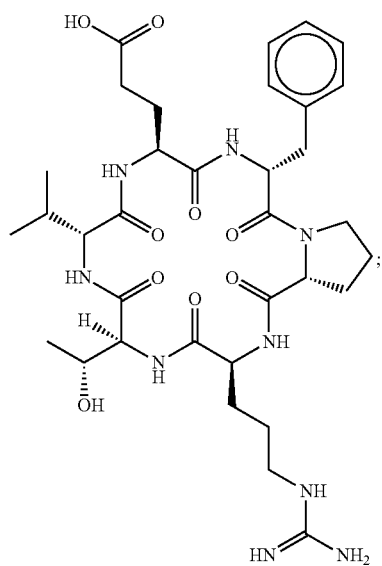
(Compound 5)
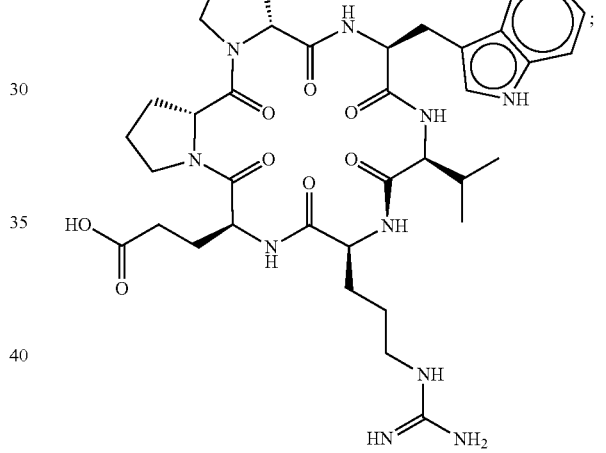
(Compound 3)
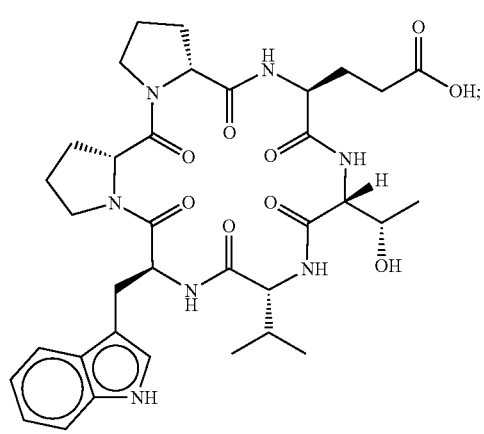
(Compound 6)
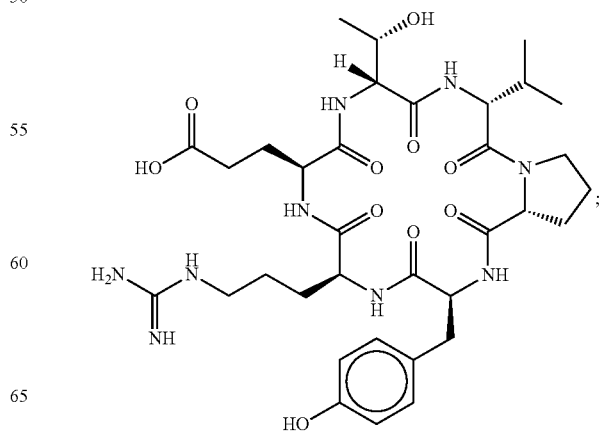

(Compound 7)
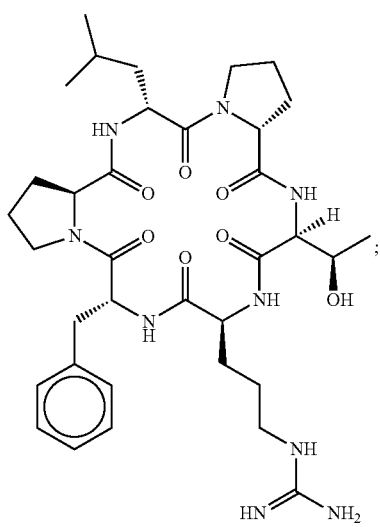
(Compound 8)
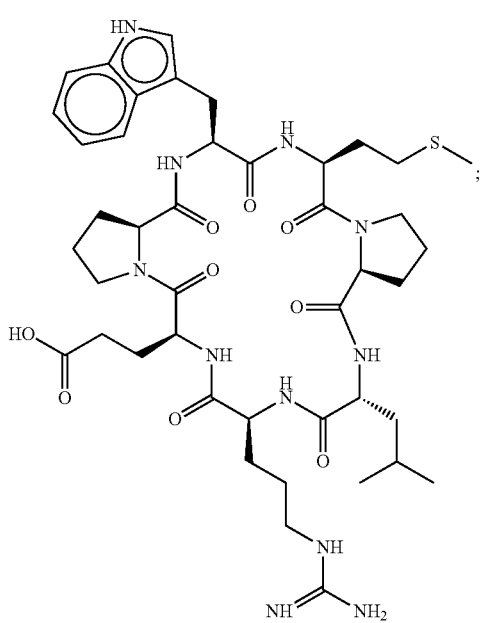
(Compound 9)
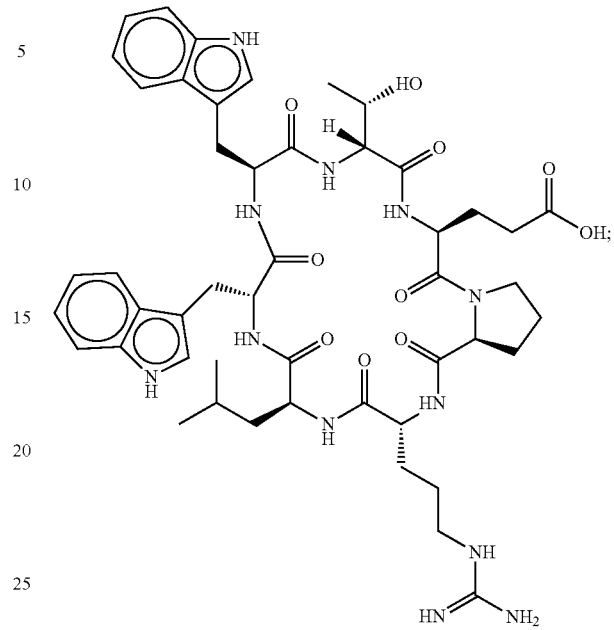
(Compound 10)
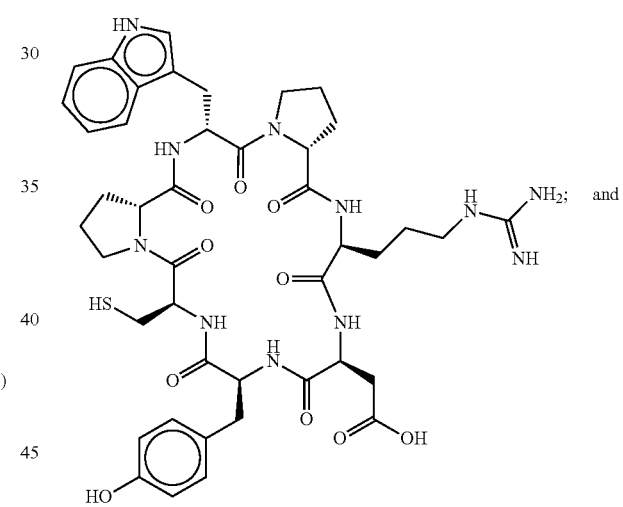
(Compound 11)
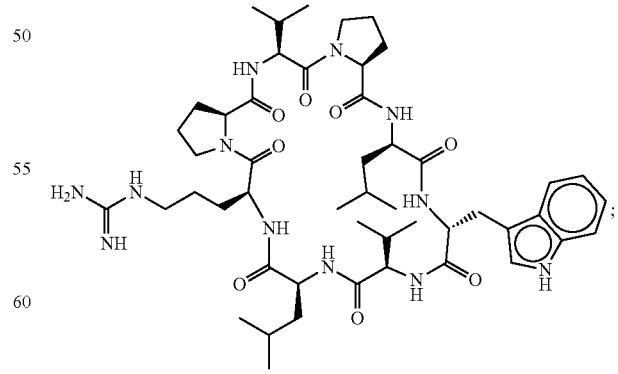
or a pharmaceutically acceptable salt of any of the foregoing.

4. The pharmaceutical composition according to claim 3, wherein the cyclic oligopeptide is selected from the group consisting of any one of Compounds 1-11
(Compound 1)
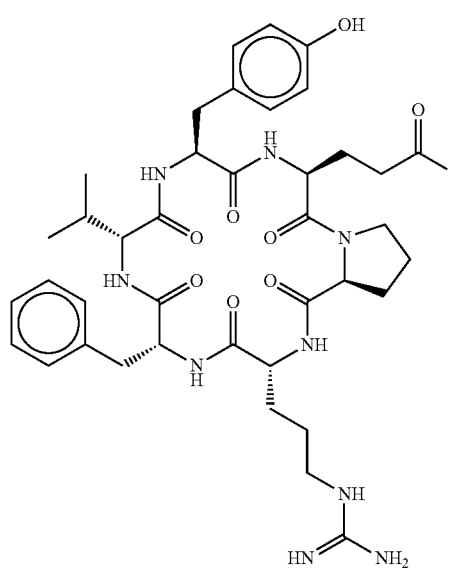
(Compound 2)
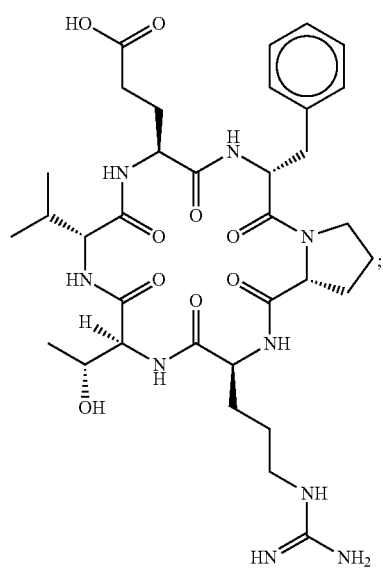
(Compound 3)
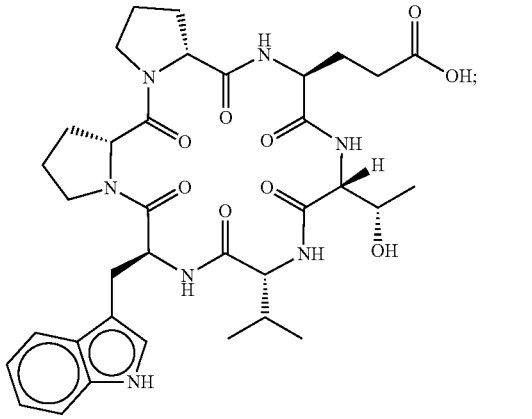
(Compound 4)
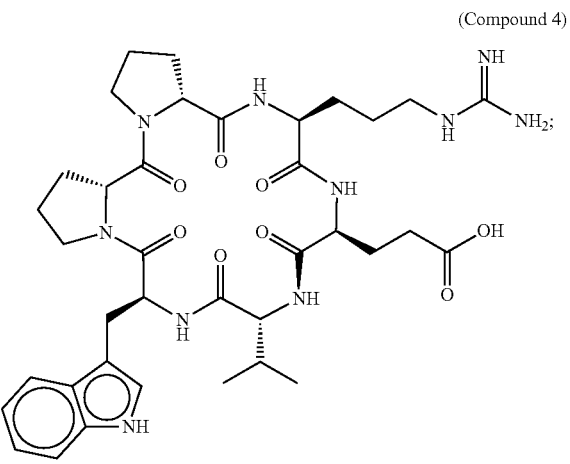
(Compound 5)
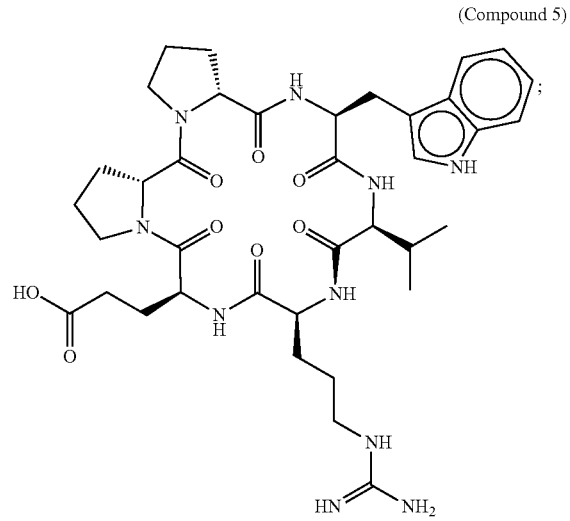

(Compound 6)
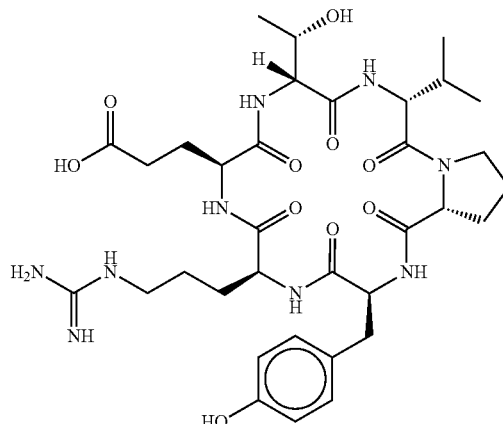
(Compound 7)
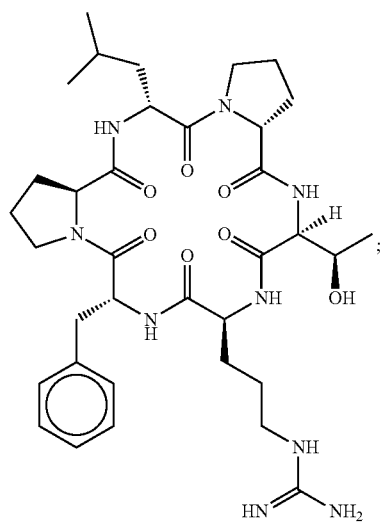
(Compound 8)
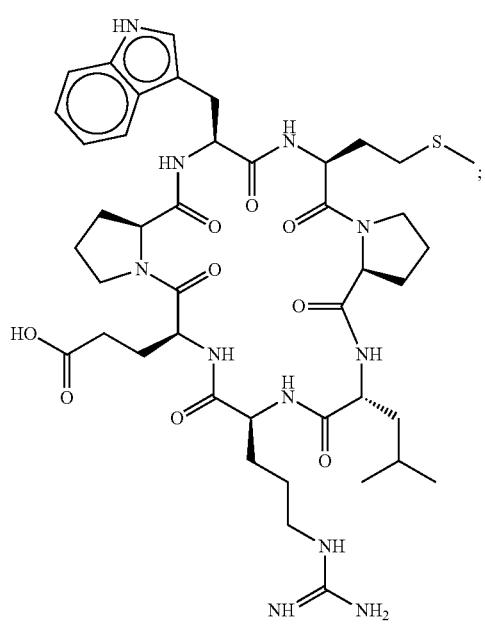
(Compound 9)
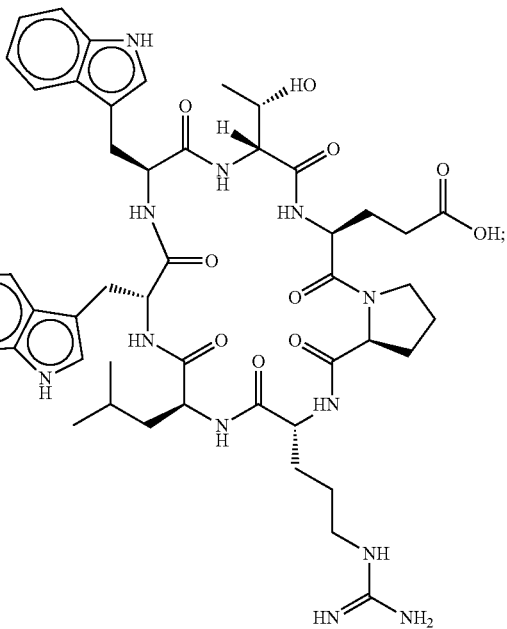
(Compound 10)
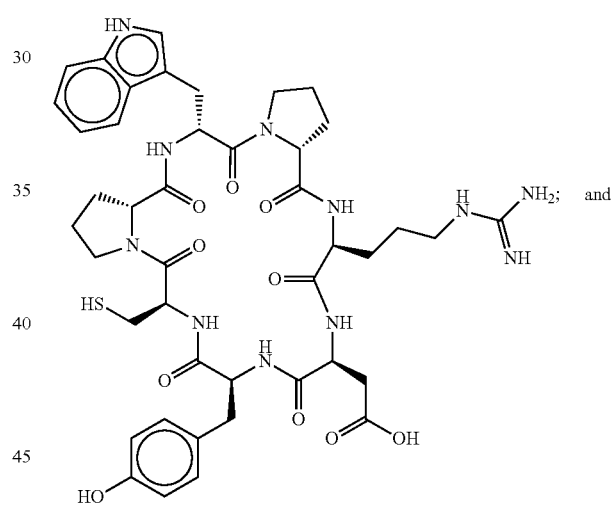
(Compound 11)
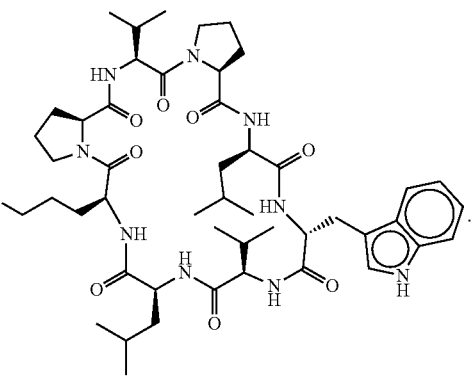
5. The pharmaceutical composition according to claim 3, wherein the composition is formulated for topical administration.

6. The pharmaceutical composition according to claim 4, wherein the composition is formulated for topical administration.

7. A method of treating atopic dermatitis in a subject in need thereof, comprising administering to the subject a therapeutically effective amount of a cyclic oligopeptide or a pharmaceutical composition comprising the cyclic oligopeptide and a pharmaceutically acceptable carrier, wherein the cyclic oligopeptide is selected from the group consisting of any one of Compounds 1-11

(Compound 1)

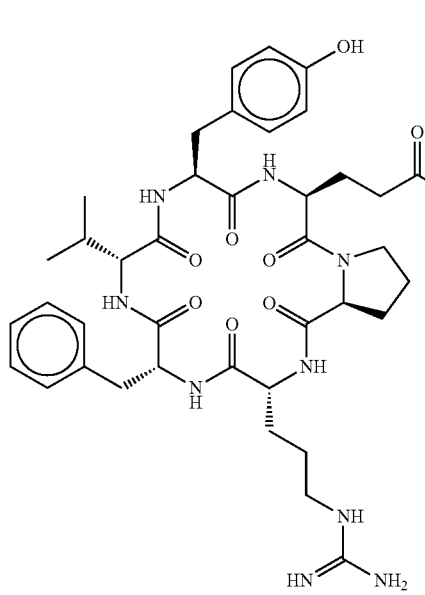

(Compound 2)

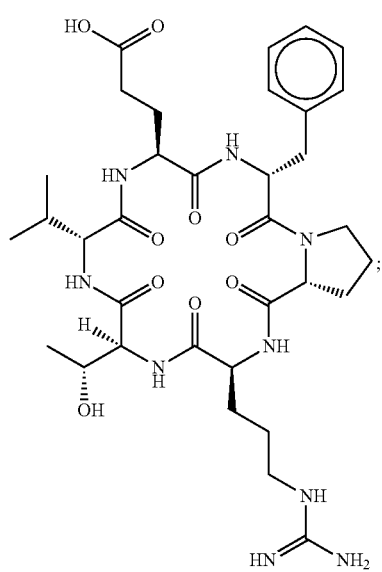

-continued

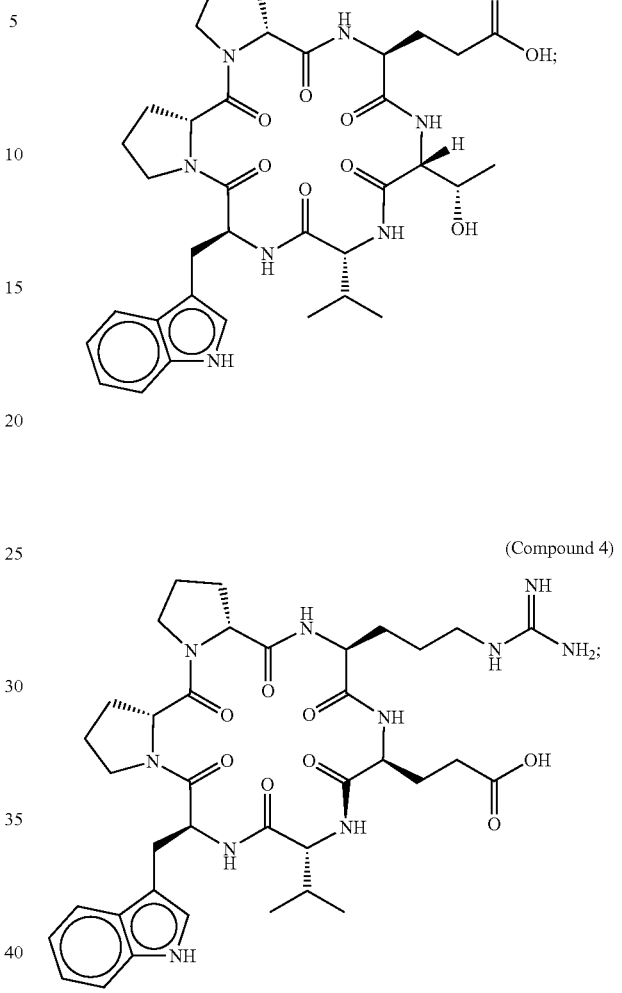

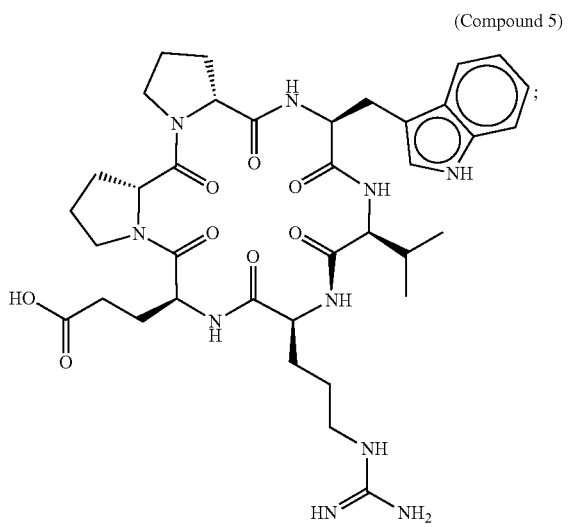

(Compound 6)
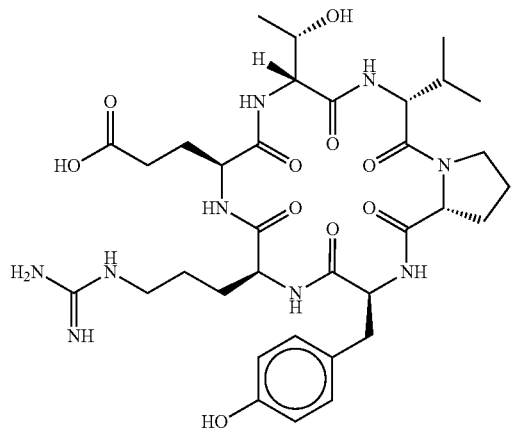
(Compound 7)
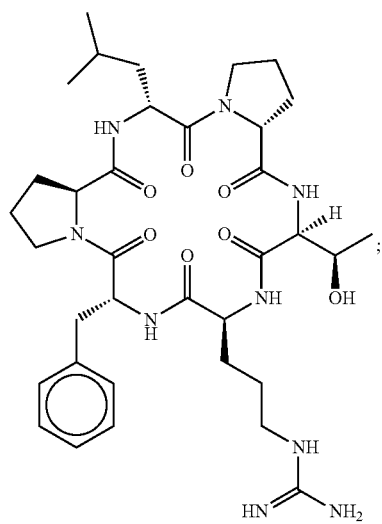
(Compound 8)
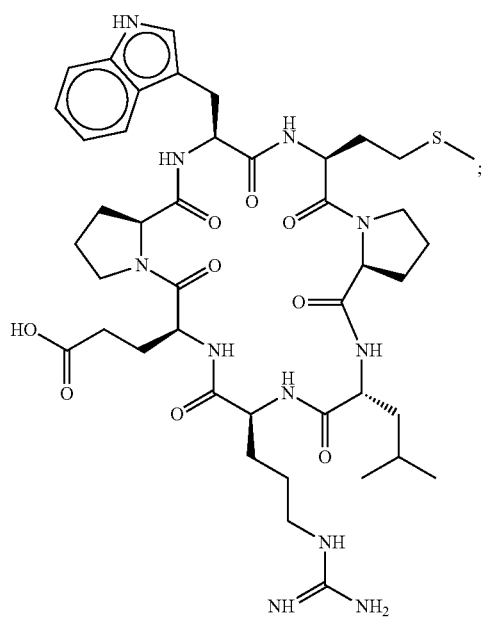
(Compound 9)
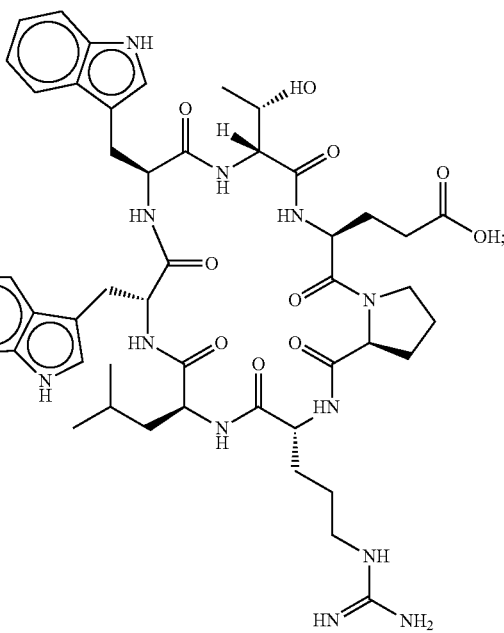
(Compound 10)
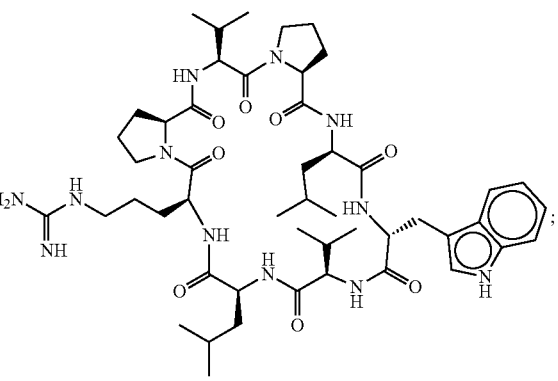
(Compound 11)
or a pharmaceutically acceptable salt of any of the foregoing.

8. The method of claim 7, wherein the cyclic oligopeptide is selected from the group consisting of any one of Compounds 1-11
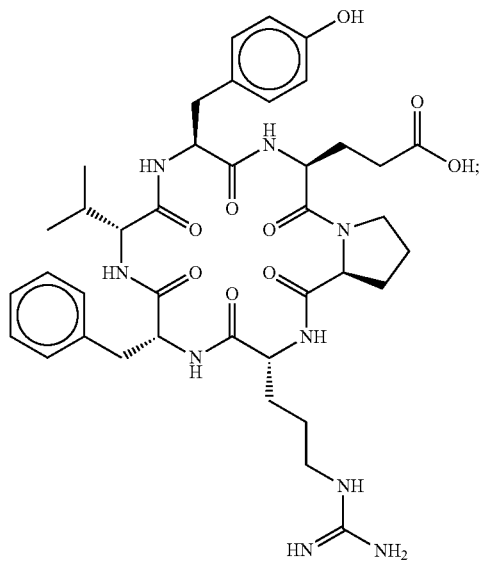
(Compound 1)
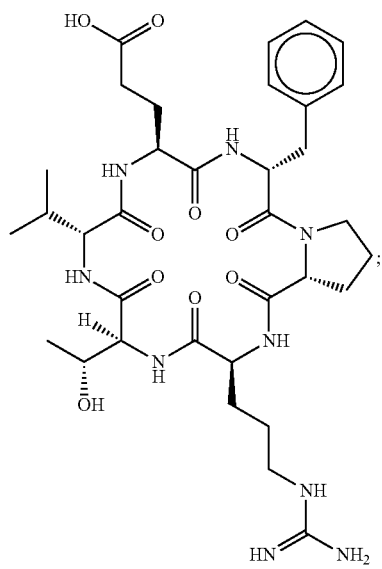
(Compound 2)
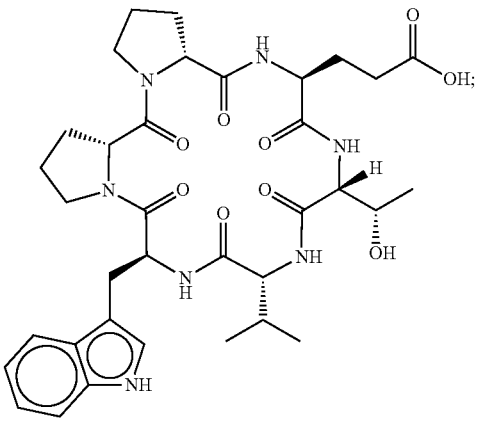
(Compound 3)
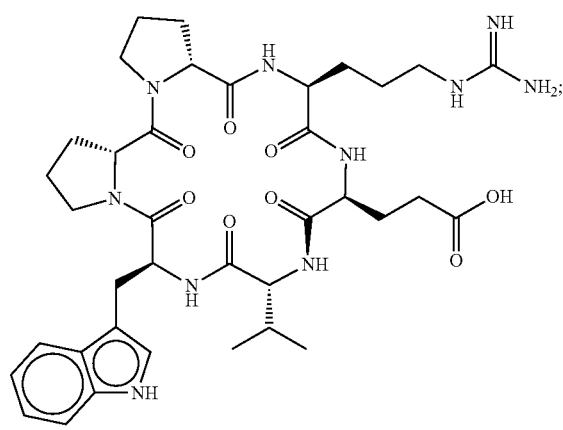
(Compound 4)
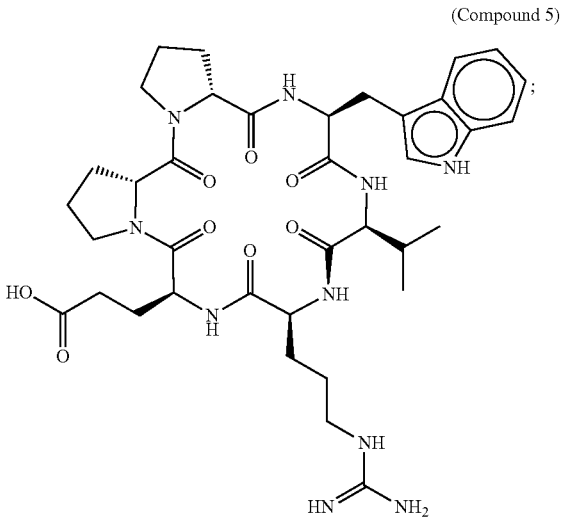
(Compound 5)

(Compound 6)
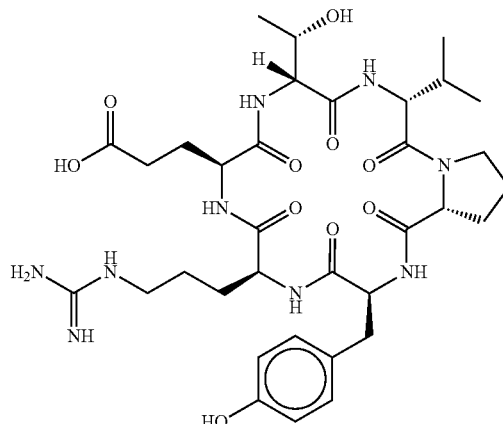
(Compound 9)
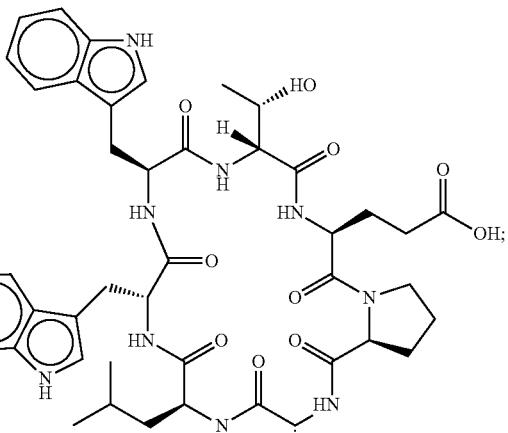
(Compound 7)
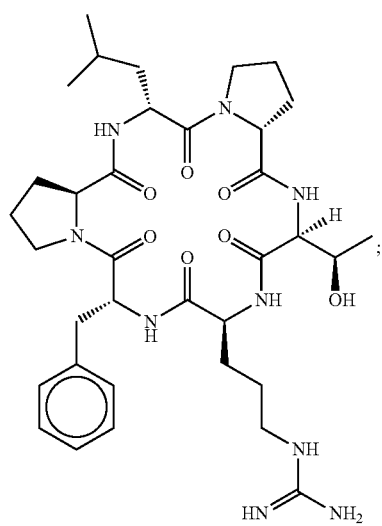
(Compound 10)
(Compound 8)
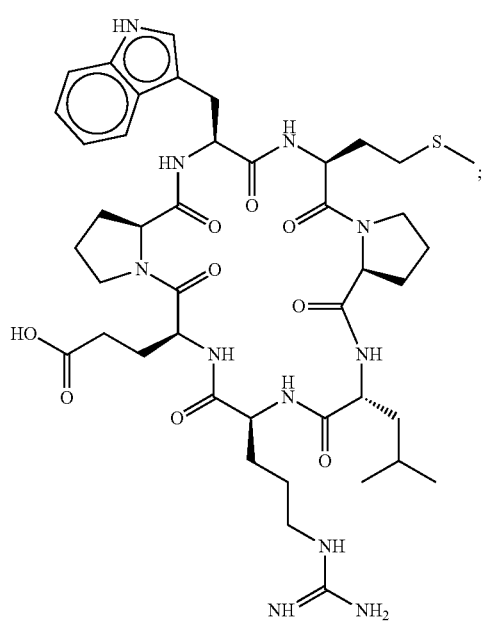
(Compound 11)
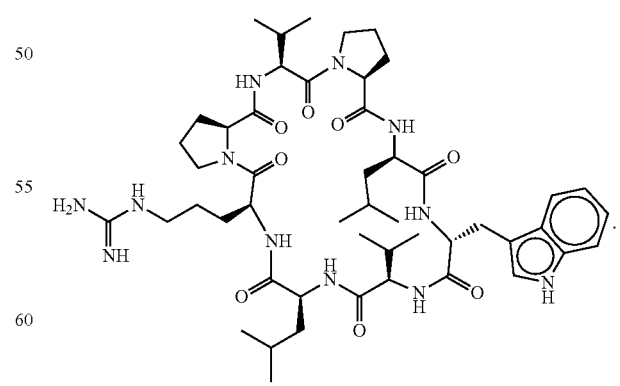
9. The method according to claim 7, wherein the cyclic oligopeptide or pharmaceutical composition is administered topically.

10. The method according to claim 8, wherein the cyclic oligopeptide or pharmaceutical composition is administered topically.

\* \* \* \* \*